United States Patent
Teufel et al.

(10) Patent No.: US 11,730,819 B2
(45) Date of Patent: *Aug. 22, 2023

(54) PEPTIDE DERIVATIVES HAVING NOVEL LINKAGE STRUCTURES

(71) Applicant: BicycleTx Limited, Cambridge (GB)

(72) Inventors: Daniel Teufel, Cambridge (GB);
Gemma Mudd, Cambridge (GB);
Silvia Pavan, Cambridge (GB)

(73) Assignee: BicycleTx Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/472,242

(22) PCT Filed: Dec. 20, 2017

(86) PCT No.: PCT/EP2017/083953
§ 371 (c)(1),
(2) Date: Jun. 21, 2019

(87) PCT Pub. No.: WO2018/115203
PCT Pub. Date: Jun. 28, 2018

(65) Prior Publication Data
US 2020/0316209 A1    Oct. 8, 2020

(30) Foreign Application Priority Data

Dec. 23, 2016  (GB) ...................................... 1622140
Aug. 23, 2017  (GB) ...................................... 1713561

(51) Int. Cl.
*A61K 47/64* (2017.01)
*A61K 47/65* (2017.01)
*C07K 7/54* (2006.01)

(52) U.S. Cl.
CPC .............. *A61K 47/64* (2017.08); *A61K 47/65* (2017.08); *C07K 7/54* (2013.01)

(58) Field of Classification Search
CPC ........ A61K 47/00; A61K 47/64; A61K 47/65; A61K 51/08; A61K 51/088; A61K 2123/00; A61K 2121/00; A61K 49/00; C07K 7/54
USPC ........... 424/1.11, 1.65, 1.69, 9.1, 9.2; 534/7, 534/10–16; 514/1, 1.1; 530/300
See application file for complete search history.

(56) References Cited

U.S. PATENT DOCUMENTS

| | | |
|---|---|---|
| 4,650,750 A | 3/1987 | Giese |
| 4,709,016 A | 11/1987 | Giese |
| 5,360,819 A | 11/1994 | Giese |
| 5,516,931 A | 5/1996 | Giese et al. |
| 5,602,273 A | 2/1997 | Giese et al. |
| 5,604,104 A | 2/1997 | Giese et al. |
| 5,610,020 A | 3/1997 | Giese et al. |
| 5,650,270 A | 7/1997 | Giese et al. |
| 6,552,065 B2 | 4/2003 | Remiszewski et al. |
| 8,138,347 B2 | 3/2012 | Knight et al. |
| 8,680,022 B2 | 3/2014 | Gregory et al. |
| 8,685,890 B2 * | 4/2014 | Winter ................... A61K 47/64 506/9 |
| 8,778,844 B2 | 7/2014 | Winter et al. |
| 9,518,081 B2 * | 12/2016 | Winter ..................... C07K 1/00 |
| 9,644,201 B2 | 5/2017 | Winter et al. |
| 9,657,288 B2 | 5/2017 | Winter et al. |
| 9,670,482 B2 | 6/2017 | Winter et al. |
| 9,670,484 B2 | 6/2017 | Winter et al. |
| 9,670,521 B2 | 6/2017 | Grabstein et al. |
| 9,932,367 B2 | 4/2018 | Stace et al. |
| 9,994,617 B2 | 6/2018 | Tite et al. |
| 10,118,947 B2 * | 11/2018 | Teufel ..................... C07K 7/06 |
| 10,294,274 B2 | 5/2019 | Teufel et al. |
| 10,441,663 B2 * | 10/2019 | Bennett .................. C07K 14/00 |

(Continued)

FOREIGN PATENT DOCUMENTS

| | | |
|---|---|---|
| CN | 101497878 A | 8/2009 |
| EP | 3192802 A1 | 7/2017 |

(Continued)

OTHER PUBLICATIONS

Chung et al, Med. Chem. Commun., vol. 4, pp. 1124-1128 (Year: 2013).*

(Continued)

*Primary Examiner* — D. L. Jones
(74) *Attorney, Agent, or Firm* — Dechert LLP; Andrea L. C. Reid; Gang Wang

(57) ABSTRACT

A compound comprising at least one looped peptide structure attached via at least one alkylamino linkage to a scaffold. Preferably the looped peptide structure is a Bicycle structure comprising two peptide loops attached to the scaffold via two alkylamino linkages and one thioether linkage, one of the linkages being common to both loops. Also provided is a method of making a compound comprising at least one looped peptide structure attached via at least one alkylamino linkages to a scaffold, the method comprising: providing a peptide having at least two residues selected from cysteine, diaminopropionic acid, D-N-Alkyldiaminopropionic acid and β-N-Alkyldiaminopropionic acid, provided that at least one of the residues is diaminopropionic acid, D-N-Alkyldiaminopropionic acid and β-N-Alkyldiaminopropionic acid; providing a scaffold molecule having at least two reactive sites for forming alkylamino or thioether linkages with the said at least two residues; and forming said linkages between the peptide and the scaffold molecule.

23 Claims, 17 Drawing Sheets

Specification includes a Sequence Listing.

(56) References Cited

U.S. PATENT DOCUMENTS

| | | | |
|---|---|---|---|
| 10,532,106 B2 | 1/2020 | Teufel et al. | |
| 10,624,968 B2* | 4/2020 | Bennett | C07K 7/64 |
| 10,792,368 B1* | 10/2020 | Teufel | C07K 7/02 |
| 10,857,196 B2* | 12/2020 | Beswick | C07K 7/64 |
| 10,870,679 B2* | 12/2020 | Teufel | A61P 27/16 |
| 10,894,808 B2* | 1/2021 | Teufel | A61P 37/00 |
| 10,899,798 B2* | 1/2021 | Bennett | A61K 49/0056 |
| 10,919,937 B2* | 2/2021 | Beswick | C07K 14/001 |
| 10,994,019 B2 | 5/2021 | Teufel et al. | |
| 11,103,591 B2 | 8/2021 | Teufel et al. | |
| 11,241,473 B2 | 2/2022 | Beswick et al. | |
| 11,396,530 B2 | 7/2022 | Beswick et al. | |
| 11,414,488 B2 | 8/2022 | Bennett et al. | |
| 2009/0222937 A1 | 9/2009 | Arnould et al. | |
| 2012/0172235 A1 | 7/2012 | Winter et al. | |
| 2014/0163201 A1 | 6/2014 | Winter et al. | |
| 2014/0256596 A1 | 9/2014 | Tite et al. | |
| 2014/0274759 A1 | 9/2014 | Walker et al. | |
| 2017/0067045 A1 | 3/2017 | Winter et al. | |
| 2018/0169254 A1 | 6/2018 | Bennett et al. | |
| 2018/0280525 A1 | 10/2018 | Teufel et al. | |
| 2018/0311300 A1 | 11/2018 | Beswick et al. | |
| 2018/0362585 A1 | 12/2018 | Teufel et al. | |
| 2018/0371020 A1 | 12/2018 | Bennett et al. | |
| 2019/0134213 A1 | 5/2019 | Teufel et al. | |
| 2019/0184025 A1 | 6/2019 | Chen et al. | |
| 2019/0263866 A1 | 8/2019 | Chen et al. | |
| 2019/0307836 A1 | 10/2019 | Keen et al. | |
| 2019/0389907 A1 | 12/2019 | Teufel et al. | |
| 2020/0129630 A1 | 4/2020 | Koehler et al. | |
| 2020/0131228 A1 | 4/2020 | Beswick et al. | |
| 2020/0171161 A1 | 6/2020 | Teufel et al. | |
| 2020/0215199 A1 | 7/2020 | Bennett et al. | |
| 2020/0283482 A1 | 9/2020 | Keen et al. | |
| 2020/0291096 A1 | 9/2020 | Keen et al. | |
| 2020/0316209 A1 | 10/2020 | Teufel et al. | |
| 2020/0354456 A1 | 11/2020 | Bennett et al. | |
| 2020/0407709 A1 | 12/2020 | Chen et al. | |
| 2021/0046145 A1 | 2/2021 | Beswick et al. | |
| 2021/0079045 A1 | 3/2021 | Bennet et al. | |
| 2021/0122785 A1 | 4/2021 | Teufel et al. | |
| 2021/0122804 A1 | 4/2021 | Teufel et al. | |
| 2021/0147484 A1 | 5/2021 | Beswick et al. | |
| 2021/0147485 A1 | 5/2021 | Teufel et al. | |
| 2021/0261620 A1 | 8/2021 | Teufel et al. | |
| 2022/0023432 A1 | 1/2022 | Teufel et al. | |
| 2022/0024982 A1 | 1/2022 | Chen et al. | |
| 2022/0031858 A1 | 2/2022 | Mcdonnell et al. | |
| 2022/0072140 A1 | 3/2022 | Stace et al. | |
| 2022/0135614 A1 | 5/2022 | Teufel | |
| 2022/0194983 A1 | 6/2022 | Teufel et al. | |
| 2022/0362390 A1 | 11/2022 | Stace et al. | |
| 2022/0387611 A1 | 12/2022 | Bennett et al. | |

FOREIGN PATENT DOCUMENTS

| | | |
|---|---|---|
| FR | 2932189 A1 | 12/2009 |
| WO | WO-2001042246 A2 | 6/2001 |
| WO | WO-2002088112 A1 | 11/2002 |
| WO | WO-2003063794 A2 | 8/2003 |
| WO | WO-2004005348 A1 | 1/2004 |
| WO | WO-2004019973 A1 | 3/2004 |
| WO | WO-2004077062 A2 | 9/2004 |
| WO | WO-2004089925 A1 | 10/2004 |
| WO | WO-2005007623 A2 | 1/2005 |
| WO | WO-2005113554 A2 | 12/2005 |
| WO | WO-2006078161 A1 | 7/2006 |
| WO | WO-2006078846 A1 | 7/2006 |
| WO | WO-2006122806 A2 | 11/2006 |
| WO | WO-2007016176 A2 | 2/2007 |
| WO | WO-2007044729 A2 | 4/2007 |
| WO | WO-2007053452 A1 | 5/2007 |
| WO | WO-2007070514 A1 | 6/2007 |
| WO | WO-2007084786 A1 | 7/2007 |
| WO | WO-2007129161 A2 | 11/2007 |
| WO | WO-2008039218 A2 | 4/2008 |
| WO | WO-2008109943 A1 | 9/2008 |
| WO | 2009098450 A2 | 8/2009 |
| WO | WO-2009114512 A1 | 9/2009 |
| WO | WO-2010089117 A1 | 8/2010 |
| WO | WO-2011018227 A2 | 2/2011 |
| WO | WO-2011090760 A1 | 7/2011 |
| WO | 2013/050616 A1 | 4/2013 |
| WO | WO-2013050615 A1 | 4/2013 |
| WO | WO-2013050616 A1 | 4/2013 |
| WO | 2014/044872 A1 | 3/2014 |
| WO | WO-2014044872 A1 | 3/2014 |
| WO | WO-2014167122 A1 | 10/2014 |
| WO | WO-2015116904 A1 | 8/2015 |
| WO | 2016067035 A1 | 5/2016 |
| WO | WO-2016067035 A1 | 5/2016 |
| WO | WO-2017191460 A1 | 11/2017 |
| WO | WO-2018096365 A1 | 5/2018 |
| WO | WO-2018115203 A1 | 6/2018 |
| WO | WO-2018115204 A1 | 6/2018 |
| WO | WO-18127699 A1 | 7/2018 |
| WO | WO-18197893 A1 | 11/2018 |
| WO | WO-2018197509 A1 | 11/2018 |
| WO | WO-2019002842 A1 | 1/2019 |
| WO | WO-2019034866 A1 | 2/2019 |
| WO | WO-2019034868 A1 | 2/2019 |
| WO | WO-20084305 A1 | 4/2020 |
| WO | WO-2008089627 A1 | 5/2020 |
| WO | WO-2020089627 A1 | 5/2020 |
| WO | WO-2020120981 A1 | 6/2020 |
| WO | WO-2020120983 A1 | 6/2020 |
| WO | WO-2020120984 A1 | 6/2020 |
| WO | WO-2020165600 A1 | 8/2020 |
| WO | WO-2020178574 A1 | 9/2020 |
| WO | WO-2020229803 A1 | 11/2020 |
| WO | WO-2021074647 A1 | 4/2021 |
| WO | WO-2022029420 A1 | 2/2022 |

OTHER PUBLICATIONS

Li et al, ACS Comb. Sci, vol. 14, pp. 673-679 (Year: 2012).*

Yu et al, Tetrahedron Letters, vol. 37, No. 11, pp. 1731-1734. (Year: 1996).*

International Search Report and Written Opinion issued by the European Patent Office as International Searching Authority for International Application No. PCT/EP2017/083953 dated May 9, 2018 (9 pages).

"Cholangiocarcinoma," Merck Manual. Accessed Mar. 12, 2017: http://surgery.usc.edu/divisions/tumor/pancreasdiseases/web%20pages/BILIARY%20SYSTEM/cholangiocarcinoma.

Adley et al., "Expression of membrane type 1 matrix metalloproteinase (MMP-14) in epithelial ovarian cancer: high level expression in clear cell carcinoma," Gynecol Oncol. Feb. 2009;112(2):319-24.

Akanuma et al., "MicroRNA-133a regulates the mRNAs of two invadopodia-related proteins, FSCN1 and MMP14, in esophageal cancer," Br J Cancer. Jan. 7, 2014;110(1):189-98.

Angelini et al., "Bicyclic peptide inhibitor reveals large contact interface with a protease target," ACS Chem Biol. May 18, 2012;7(5):817-21.

Askoxylakis et al., "A new peptide ligand for targeting human carbonic anhydrase IX, identified through the phage display technology," PLoS One. Dec. 31, 2010;5(12):e15962.

Augoff et al., "Upregulated expression and activation of membrane-associated proteases in esophageal squamous cell carcinoma," Oncol Rep. Jun. 2014;31(6):2820-6.

Baek et al. "Effects of Histidine and Sucrose on the Biophysical Properties of a Monoclonal Antibody," Pharm Res (2017) 34:629-639.

Banerji et al., "Preliminary pharmacokinetic assessment of BT1718: A phase I/IIa trial of BT1718 (a first in class Bicycle Toxin Conjugate) in patients with advanced solid tumours," Nov. 13, 2018;abstract 178.

Barbolina et al., "Microenvironmental regulation of membrane type 1 matrix metalloproteinase activity in ovarian carcinoma cells via collagen-induced EGR1 expression," J Biol Chem. Feb. 16, 2007;282(7):4924-4931.

(56) References Cited

OTHER PUBLICATIONS

Bardia et al., "Efficacy and Safety of Anti-Trop-2 Antibody Drug Conjugate Sacituzumab Govitecan (IMMU-132) in Heavily Pretreated Patients With Metastatic Triple-Negative Breast Cancer," J Clin Oncol. Jul. 1, 2017;35(19):2141-2148.
Bennett et al., "Development of BT1718, a Bicycle Drug Conjugate® (BDC) targeting MT1-MMP for treatment of solid tumours," Eur J Cancer. Dec. 2016;69(suppl 1):S21(42;P013).
Berenson, "Multiple Myeloma," Merck Manual. Revised Oct. 2021; Accessed Oct. 4, 2022: https://www.merckmanuals.com/home/blood-disorders/plasma-cell-disorders/multiple-myeloma?query=multiple%20myeloma.
Berge et al., "Pharmaceutical Salts," J Pharm Sci. 1977;66(1):1-19.
Bicycle Therapeutics, "Bicycle Therapeutics and Cancer Research UK Announce Inititation of First Clinical Study of a Bicyclic Peptide (Bicycle®)," Press Release. Feb. 13, 2018: https://investors.bicycletherapeutics.com/node/6651/pdf.
Bogaerts et al., "Individual patient data analysis to assess modifications to the RECIST criteria," Eur J Cancer. Jan. 2009;45(2):248-60.
Borghaei et al., "Nivolumab versus Docetaxel in Advanced Nonsquamous Non-Small-Cell Lung Cancer," N Engl J Med. Oct. 22, 2015;373(17):1627-39.
Bouchard et al., "Antibody-drug conjugates—a new wave of cancer drugs," Bioorg Med Chem Lett. Dec. 1, 2014;24(23):5357-63.
Brahmer et al., "Nivolumab versus Docetaxel in Advanced Squamous-Cell Non-Small-Cell Lung Cancer," N Engl J Med. Jul. 9, 2015;373(2):123-35.
Cabanillas et al., "Phase I study of maytansine using a 3-day schedule," Cancer Treat Rep. Mar. 1978;62(3):425-8.
Cancer Research UK, "Soft tissue sarcomas," Accessed Sep. 30, 2022: http://about-cancer.cancerresearchuk.org/about-cancer/soft-tissue-sarcoma.
Cancer Research UK, "Triple Negative Breast Cancer," Accessed Sep. 30, 2022: https://www.cancerresearchuk.org/about-cancer/breast-cancer/stages-types-grades/types/triple-negative-breast-cancer#.
Cancer Research UK, "Types of lung cancer," Accessed Sep. 30, 2022: https://www.cancerresearchuk.org/about-cancer/lung-cancer/stages-types-grades/types#.
Cancer Research UK, "Your mouth and cancer drugs," Accessed Sep. 30, 2022: https://www.cancerresearchuk.org/about-cancer/cancer-in-general/treatment/cancer-drugs/side-effects/your-mouth.
Center for Pancreatic and Biliary Diseases, "Bile Duct Cancer," University of Southern California, Department of Surgery. Retreived from https://web.archive.org/web/20171207023733/http://www.surgery.usc.edu:80/divisions/tumor/PancreasDiseases/web%20pages/BILIARY%20SYSTEM/cholangiocarcinoma.html.
Chabner et al., "Initial clinical trials of maytansine, an antitumor plant alkaloid," CancerTreat Rep. Mar. 1978;62(3):429-33.
Chahinian et al., "Phase I study of weekly maytansine given by iv bolus or 24-hour infusion," Cancer Treat Rep. Nov.-Dec. 1979;63(11-12):1953-60.
Chandrasekar, "Bladder Cancer," Merck Manual. Modified Sep. 2022; Accessed Sep. 30, 2022: http://www.merckmanuals.com/home/kidney_and_urinary_tract_disorders/cancers_of_the_kidney_and_genitourinary_tract/bladder_cancer.html.
Chandrasekar, "Prostate Cancer," Merck Manual. Modified Sep. 2022; Accessed Sep. 30, 2022: http://www.merckmanuals.com/home/kidney_and_urinary_tract_disorders/cancers_of_the_kidney_and_genitourinary_tract/prostate_cancer.html?qt=prostate cancer&alt=sh.
Chang et al., "Subtiligase: a tool for semisynthesis of proteins," Proc Natl Acad Sci USA. Dec. 20, 1994;91(26):12544-8.
Chen and Harrison, "Cell-penetrating peptides in drug development: enabling intracellular targets," Biochem Soc Trans. Aug. 2007;35(Pt 4):821-5.
Chen et al., "Structurally diverse cyclisation linkers impose different backbone conformations in bicyclic peptides," Chembiochem. May 7, 2012;13(7):1032-8.
Cherney et al., "Macrocyclic amino carboxylates as selective MMP-8 inhibitors," J Med Chem. May 21, 1998;41(11):1749-51.
Chiche et al., "Hypoxia-inducible carbonic anhydrase IX and XII promote tumor cell growth by counteracting acidosis through the regulation of the intracellular pH," Cancer Res. Jan. 1, 2009;69(1):358-68.
Committee for Medicinal Products for Human Use (CHMP), "Assessment Report: Kadcyla; International non-proprietary name: Trastuzumab emtansine; Procedure No. EMEA/H/C/002389/0000," European Medicines Agency. Sep. 19, 2013;EMA/749228/2013.
Cook et al., "Pharmacokinetic (PK) Assessment of BT1718: A phase I/II a study of BT1718, a first in class bicycle toxin conjugate (BTC), in patients (pts) with advanced solid tumours," Ann Oncol. Oct. 2019;30(suppl 5):464P.
Cortes et al., "Phase II study of the halichondrin B analog eribulin mesylate in patients with locally advanced or metastatic breast cancer previously treated with an anthracycline, a taxane, and capecitabine," J Clin Oncol. Sep. 1, 2010;28(25):3922-8.
Dawson et al., "Synthesis of proteins by native chemical ligation," Science. Nov. 4, 1994;266(5186):776-9.
De la Peña et al., "Expression of the matrix metalloproteases 2, 14, 24, and 25 and tissue inhibitor 3 as potential molecular markers in advanced human gastric cancer," Dis Markers. 2014;2014:285906.
Derossi et al., "The third helix of the Antennapedia homeodomain translocates through biological membranes," J Biol Chem. Apr. 8, 1994;269(14):10444-50.
Diamantis and Banerji, "Antibody-drug conjugates—an emerging class of cancer treatment," Br J Cancer. Feb. 16, 2016;114(4):362-7.
Driggers et al., "The exploration of macrocycles for drug discovery—an underexploited structural class," Nat Rev Drug Discov. Jul. 2008;7(7):608-24.
Dubois et al., "New ways to image and target tumour hypoxia and its molecular responses," Radiother Oncol. Sep. 2015;116(3):352-7.
Eagan et al., "Early clinical study of an intermittent schedule for maytansine (NSC-153858): brief communication," J Natl Cancer Inst. Jan. 1978;60(1):93-6.
Eisenhauer et al., "New response evaluation criteria in solid tumours: revised RECIST guideline (version 1.1)," Eur J Cancer. Jan. 2009;45(2):228-47.
Ellenrieder et al., "Role of MT-MMPs and MMP-2 in pancreatic cancer progression," Int J Cancer. Jan. 1, 2000;85(1):14-20.
Elson-Schwab et al., "Guanidinylated neomycin delivers large, bioactive cargo into cells through a heparan sulfate-dependent pathway," J Biol Chem. May 4, 2007;282(18):13585-91.
Fehrenbacher et al., "Atezolizumab versus docetaxel for patients with previously treated non-small-cell lung cancer (POPLAR): a multicentre, open-label, phase 2 randomised controlled trial," Lancet. Apr. 30, 2016;387(10030):1837-46.
Francis et al., "Bone and Soft Tissue Sarcomas: UK Incidence and Survival: 1996-2010," National Cancer Intelligence Network. Nov. 2013;v2.0.
Gaisky et al., "Phase I trial of the prostate-specific membrane antigen-directed immunoconjugate MLN2704 in patients with progressive metastatic castration-resistant prostate cancer," J Clin Oncol. May 1, 2008;26(13):2147-54.
Gandhi et al., "MP69-11 Carbonic Anhydrase IX Assay: A Paradigm Shift in Diagnosis of Malignant Cystic Renal Lesions," J Urol. May 18, 2015;193(4S):e870-e871.
Gelb et al., "Abstract A047: MT1-MMP Immunohistochemistry (IHC) analysis of tumor microarrays (TMAs) using a novel scoring system guides patient selection for BT1718 expansion cohorts," Mol Cancer Ther. 2019;18(12 suppl):A047.
Gentilucci et al., "Chemical modifications designed to improve peptide stability: incorporation of non-natural amino acids, pseudo-peptide bonds, and cyclization." Curr Pharm Des. 2010;16(28):3185-203.
Gradishar et al., "Significantly longer progression-free survival with nab-paclitaxel compared with docetaxel as first-line therapy for metastatic breast cancer," J Clin Oncol. Aug. 1, 2009;27(22):3611-9.
Gresh, "Neuroblastoma," Merck Manual. Modified Sep. 2022; Accessed Oct. 3, 2022: https://www.merckmanuals.com/professional/pediatrics/pediatric-cancers/neuroblastoma#.

(56) References Cited

OTHER PUBLICATIONS

Grisold et al., "Peripheral neuropathies from chemotherapeutics and targeted agents: diagnosis, treatment, and prevention," Neuro Oncol. Sep. 2012;14 Suppl 4(Suppl 4):iv45-54.
Gu et al., "The influence of the penetrating peptide iRGD on the effect of paclitaxel-loaded MT1-AF7p-conjugated nanoparticles on glioma cells," Biomaterials. Jul. 2013;34(21):5138-48.
Gupta et al., "Intracellular delivery of large molecules and small particles by cell-penetrating proteins and peptides," Adv Drug Deliv Rev. Feb. 28, 2005;57(4):637-51.
Hanna et al., "Randomized phase III trial of pemetrexed versus docetaxel in patients with non-small-cell lung cancer previously treated with chemotherapy," J Clin Oncol. May 1, 2004;22(9):1589-97.
Harrison et al., "Abstract 5144: BT1718, a novel bicyclic peptide-maytansinoid conjugate targeting MT1-MMP for the treatment of solid tumors: Design of bicyclic peptide and linker selection," Cancer Res. 2017;77(13 suppl):5144.
He et al., "Matrix metalloproteinase-14 is a negative prognostic marker for patients with gastric cancer," Dig Dis Sci. May 2013;58(5):1264-70.
Heinis et al., "Phage-encoded combinatorial chemical libraries based on bicyclic peptides," Nat. Chem. Biol. 2009;5(7):502-7.
Helft et al., "A phase 1 study of cantuzumab mertansine administered as a single intravenous infusion once weekly in patients with advanced solid tumors," Clin Cancer Res. Jul. 1, 2004;10(13):4363-8.
Herbst et al., "Pembrolizumab versus docetaxel for previously treated, PD-L1-positive, advanced non-small-cell lung cancer (KEYNOTE-010): a randomised controlled trial," Lancet. Apr. 9, 2016;387(10027):1540-1550.
Hershman, "Thyroid Cancers," Merck Manual. Revised Sep. 2020; Accessed Sep. 30, 2021: http://www.merckmanuals.com/professional/endocrine-and-metabolic-disorders/thyroid-disorders/thyroid-cancers.
Hu-Lieskovan et al. "New combination strategies using PD-1/L1 checkpoint inhibitors as a backbone," Cancer J. 2017; 23(1):10-22.
Ip et al., "Atypical localization of membrane type 1-matrix metalloproteinase in the nucleus is associated with aggressive features of hepatocellular carcinoma," Mol Carcinog. Mar. 2007;46(3):225-30.
Jackson and Stover, "Using the Lessons Learned From the Clinic to Improve the Preclinical Development of Antibody Drug Conjugates," Pharm Res. Nov. 2015;32(11):3458-69.
Jones et al., "Randomized phase III study of docetaxel compared with paclitaxel in metastatic breast cancer," J Clin Oncol. Aug. 20, 2005;23(24):5542-51.
Kamat et al., "The clinical relevance of stromal matrix metalloproteinase expression in ovarian cancer," Clin Cancer Res. Mar. 15, 2006;12(6):1707-14.
Kang et al., "A randomized, open-label, multicenter, adaptive phase 2/3 study of trastuzumab emtansine (T-DM1) versus a taxane (TAX) in patients (pts) with previously treated HER2-positive locally advanced or metastatic gastric/gastroesophageal junction adenocarcinoma (LA/MGC/GEJC)," J Clin Oncol. Feb. 1, 2016;34(4 suppl).
Keith, "Lung Carcinoma," Merck Manual. Accessed Revised Jul. 2020; Accessed Sep. 30, 2021: http://merckmanuals.com/professional/pulmonary-disorders/tumors-of-the-lungs/lung-carcinoma.
Kellog et al., "Disulfide-linked antibody-maytansinoid conjugates: optimization of in vivo activity by varying the steric hindrance at carbon atoms adjacent to the disulfide linkage," Bioconjug Chem. Apr. 20, 2011;22(4):717-27.
Kemp and McNamara, "Conformationally restricted cyclic nonapeptides derived from L-cysteine and LL-3-amino-2-piperidone-6-carboxylic acid (LL-Acp), a potent .beta.-turn-inducing dipeptide analog," J Org Chem. 1985;50(26):5834-8.
Kerkelä et al., "Differential patterns of stromelysin-2 (MMP-10) and MT1-MMP (MMP-14) expression in epithelial skin cancers," Br J Cancer. Mar. 2, 2001;84(5):659-69.
Kessenbrock et al., "Matrix metalloproteinases: regulators of the tumor microenvironment," Cell. Apr. 2, 2010;141(1):52-67.
Kikuchi et al., "Immunohistochemical detection of membrane-type-1-matrix metalloproteinase in colorectal carcinoma," Br J Cancer. Jul. 2000;83(2):215-8.
Kreidieh et al., "Overview, prevention and management of chemotherapy extravasation," World J Clin Oncol. Feb. 10, 2016;7(1):87-97.
Krop et al., "Trastuzumab emtansine versus treatment of physician's choice for pretreated HER2-positive advanced breast cancer (TH3RESA): a randomised, open-label, phase 3 trial," Lancet Oncol. Jun. 2014;15(7):689-99.
Landolt et al., "Clear Cell Renal Cell Carcinoma is linked to Epithelial-to-Mesenchymal Transition and to Fibrosis," Physiol Rep. Jun. 2017;5(11):e13305.
Laudanski et al., "Increased serum level of membrane type 1-matrix metalloproteinase (MT1-MMP/MMP-14) in patients with breast cancer," Folia Histochem Cytobiol. Jan. 1, 2010;48(1):101-3.
Leighton, "Pharmacology Review: Kadcyla (ado-trastuzumab emtansine)," Center for Drug Evaluation and Research Application No. 125427Orig1s000. Feb. 1, 2013.
Li et al., "The overexpression membrane type 1 matrix metalloproteinase is associated with the progression and prognosis in breast cancer," Am J Transl Res. Jan. 15, 2015;7(1):120-7.
Lovering et al., "Escape from flatland: increasing saturation as an approach to improving clinical success," J Med Chem. Nov. 12, 2009;52(21):6752-6.
Mark, "Renal Cell Carcinoma," Merck Manual. Revised Sep. 2019; Accessed Sep. 30, 2021: http://www.merckmanuals.com/professional/genitourinary-disorders/genitourinary-cancer/renal-cell-carcinoma.
Milowsky et al., "Phase 1/2 multiple ascending dose trial of the prostate-specific membrane antigen-targeted antibody drug conjugate MLN2704 in metastatic castration-resistant prostate cancer," Urol Oncol. Dec. 2016;34(12):530.e15-530.e21.
Mohammad et al., "Prognostic value of membrane type 1 and 2 matrix metalloproteinase expression and gelatinase A activity in bladder cancer," Int J Biol Markers. Apr.-Jun. 2010;25(2):69-74.
Moraes et al., "Immune checkpoint inhibitors (anti PD-1 or anti PD-L1) versus chemotherapy for second- or third-line treatment of metastatic non-small cell lung cancer," Cochrane Database Syst Rev. 2017; 2017(4):CD012644.
Mugera and Ward, "Acute toxicity of maytansine in F344 rats," Cancer Treat Rep. Oct. 1977;61(7):1333-8.
National Cancer Institute, "Understanding Cancer," Accessed Dec. 30, 2022: https://www.cancer.gov/about-cancer/understanding.
National Cancer Institute, "What is Cancer?" Updated Oct. 11, 2021: https://www.cancer.gov/about-cancer/understanding/what-is-cancer.
Neri and Supuran, "Interfering with pH regulation in tumours as a therapeutic strategy," Nat Rev Drug Discov. Sep. 16, 2011;10(10):767-77.
Nestor, "The medicinal chemistry of peptides," Curr Med Chem. 2009;16(33):4399-418.
Nguyen, "Colorectal Cancer," Merck Manual. Revised Mar. 2021; Modified Sep. 2022: https://www.merckmanuals.com/home/digestive-disorders/tumors-of-the-digestive-system/colorectal-cancer#.
Nguyen, "Pancreatic Cancer," Merck Manual. Revised Mar. 2021; Accessed Oct. 4, 2022: https://www.merckmanuals.com/home/digestive-disorders/tumors-of-the-digestive-system/pancreatic-cancer?query=pancreatic%20cancer.
NIH National Human Genome Research Institute, "Animal Model," Genome.gov. Jan. 4, 2022.
Oehlke et al., "Cellular uptake of an alpha-helical amphipathic model peptide with the potential to deliver polar compounds into the cell interior non-endocytically," Biochim Biophys Acta. Nov. 11, 1998;1414(1-2):127-39.
Okuyama et al., "Small-molecule mimics of an alpha-helix for efficient transport of proteins into cells," Nat Methods. Feb. 2007;4(2):153-9.
Pahwa et al., "Monitoring and Inhibiting MT1-MMP during Cancer Initiation and Progression," Cancers (Basel). Feb. 17, 2014;6(1):416-35.
PCT Application PCT/GB2020/050505, filed Mar. 3, 2020.

(56) References Cited

OTHER PUBLICATIONS

PCT International Search Report and Written Opinion for PCT/GB2020/051140, dated Aug. 20, 2020.
PCT International Search Report and Written Opinion from PCT/EP2017/083954, dated Apr. 18, 2018.
PCT International Search Report and Written Opinion from PCT/GB2015/053247, dated Jan. 18, 2016.
PCT International Search Report and Written Opinion from PCT/GB2017/051250, dated Jul. 28, 2017.
PCT International Search Report and Written Opinion from PCT/GB2017/053560, dated Jan. 29, 2018.
PCT International Search Report and Written Opinion from PCT/GB2018/051118, dated Jun. 4, 2018.
PCT International Search Report and Written Opinion from PCT/GB2019/053080, dated Jan. 30, 2020.
PCT International Search Report and Written Opinion from PCT/GB2020/051140, dated Aug. 12, 2020.
PCT International Search Report from PCT/GB2019/053020, dated Apr. 6, 2020.
Peng et al., "Combined features based on MT1-MMP expression, CD11b + immunocytes density and LNR predict clinical outcomes of gastric cancer," J Transl Med. Jun. 2013;11(1):153.
Pietraszek et al., "Lumican: a new inhibitor of matrix metalloproteinase-14 activity," FEBS Lett. Nov. 28, 2014;588(23):4319-24.
Pivot et al., "Pooled analyses of eribulin in metastatic breast cancer patients with at least one prior chemotherapy," Ann Oncol. Aug. 2016;27(8):1525-31.
Poon et al., "Preclinical safety profile of trastuzumab emtansine (T-DM1): mechanism of action of its cytotoxic component retained with improved tolerability," Toxicol Appl Pharmacol. Dec. 1, 2013;273(2):298-313.
Purdie and Benoiton, "Piperazinedione formation from esters of dipeptides containing glycine, alanine, and sarcosine: the kinetics in aqueous solution," J Chem Soc Perkin 2. 1973;14:1845-52.
Qi et al., "Serial determination of glomerular filtration rate in conscious mice using FITC-inulin clearance," Am J Physiol Renal Physiol. Mar. 2004;286(3):F590-6.
Ramirez et al., "Defining causative factors contributing in the activation of hedgehog signaling in diffuse large B-cell lymphoma," Leuk Res. Oct. 2012;36(10):1267-73.
Reagan-Shaw et al., "Dose translation from animal to human studies revisited," FASEB J. Mar. 2008;22(3):659-61.
Remacle et al., "Membrane type I-matrix metalloproteinase (MT1-MMP) is internalised by two different pathways and is recycled to the cell surface," J Cell Sci. Oct. 1, 2003;116(Pt 19):3905-16.
Remacle et al., "Novel MT1-MMP small-molecule inhibitors based on insights into hemopexin domain function in tumor growth," Cancer Res. May 1, 2012;72(9):2339-49.
Rodon et al., "Cantuzumab mertansine in a three-times a week schedule: a phase I and pharmacokinetic study," Cancer Chemother Pharmacol. Oct. 2008;62(5):911-9.
Rostovtsev et al., "A stepwise huisgen cycloaddition process: copper(I)-catalyzed regioselective "ligation" of azides and terminal alkynes," Angew Chem Int Ed Engl. Jul. 15, 2002;41(14):2596-9.
Scagliotti et al., "Phase III study comparing cisplatin plus gemcitabine with cisplatin plus pemetrexed in chemotherapy-naive patients with advanced-stage non-small-cell lung cancer," J Clin Oncol. Jul. 20, 2008;26(21):3543-51.
Schiller et al., "Comparison of four chemotherapy regimens for advanced non-small-cell lung cancer," N Engl J Med. Jan. 10, 2002;346(2):92-8.
Schreiber and Fersht, "Rapid, electrostatically assisted association of proteins," Nat Struct Biol. May 1996;3(5):427-31.
Seely and Frazier, "Regulatory Forum Opinion Piece*: Dispelling Confusing Pathology Terminology: Recognition and Interpretation of Selected Rodent Renal Tubule Lesions," Toxicol Pathol. Jun. 2015;43(4):457-63.

Sepiashvili et al., "Potentially novel candidate biomarkers for head and neck squamous cell carcinoma identified using an integrated cell line-based discovery strategy," Mol Cell Proteomics. Nov. 2012;11(11):1404-15.
Shah et al., "Phase I study of IMGN901, a CD56-targeting antibody-drug conjugate, in patients with CD56-positive solid tumors," Invest New Drugs. Jun. 2016;34(3):290-9.
Shah, "Update on metastatic gastric and esophageal cancers," J Clin Oncol. Jun. 1, 2015;33(16):1760-9.
Shen et al., "Non-Clinical Disposition and Metabolism of DM1, a Component of Trastuzumab Emtansine (T-DM1), in Sprague Dawley Rats," Drug Metab Lett. 2015;9(2):119-31.
Sibaud et al., "Pigmentary disorders induced by anticancer agents, part I: chemotherapy," Ann Dermatol Venereol. Mar. 2013;140(3):183-96.
Sounni et al., "MT1-MMP expression promotes tumor growth and angiogenesis through an upregulation of vascular endothelial growth factor expression," FASEB J. Apr. 2002;16(6):555-64.
Stathis et al., "A Phase I Study of IMGN529, an Antibody-Drug Conjugate (ADC) Targeting CD37, in Adult Patients with Relapsed or Refractory B-Cell Non-Hodgkin's Lymphoma (NHL)," Blood. 2014;124(21):1760.
Sun et al., "Carbohydrate and protein immobilization onto solid surfaces by sequential Diels-Alder and azide-alkyne cycloadditions," Bioconjug Chem. Jan.-Feb. 2006;17(1):52-7.
Suojanen et al., "A novel and selective membrane type-1 matrix metalloproteinase (MT1-MMP) inhibitor reduces cancer cell motility and tumor growth," Cancer Biol Ther. Dec. 2009;8(24):2362-70.
Supuran, "Carbonic anhydrases: novel therapeutic applications for inhibitors and activators," Nat Rev Drug Discov. Feb. 2008;7(2):168-81.
Thake et al., "Toxicity of Maytansine (NSC 153858) in Dogs and Monkeys," PB—U.S. National Technical Information Service. Feb. 1975;244628.
Thevenard et al., "The YSNSG cyclopeptide derived from tumstatin inhibits tumor angiogenesis by down-regulating endothelial cell migration," Int J Cancer. Mar. 1, 2010;126(5):1055-66.
Timmerman et al., "Rapid and quantitative cyclization of multiple peptide loops onto synthetic scaffolds for structural mimicry of protein surfaces," Chembiochem. May 2005;6(5):821-4.
Tolcher et al., "Cantuzumab mertansine, a maytansinoid immunoconjugate directed to the CanAg antigen: a phase I, pharmacokinetic, and biologic correlative study," J Clin Oncol. Jan. 15, 2003;21(2):211-22.
Trouche et al., "Small multivalent architectures mimicking homotrimers of the TNF superfamily member CD40L: delineating the relationship between structure and effector function," J Am Chem Soc. Nov. 7, 2007;129(44):13480-92.
Trudel et al., "Membrane-type-1 matrix metalloproteinase, matrix metalloproteinase 2, and tissue inhibitor of matrix proteinase 2 in prostate cancer: identification of patients with poor prognosis by immunohistochemistry," Hum Pathol. May 2008;39(5):731-9.
Tugyi et al., "Partial D-amino acid substitution: Improved enzymatic stability and preserved Ab recognition of a MUC2 epitope peptide," Proc Natl Acad Sci U S A. Jan. 11, 2005;102(2):413-8.
Tutt et al., "Abstract S3-01: The TNT trial: A randomized phase III trial of carboplatin (C) compared with docetaxel (D) for patients with metastatic or recurrent locally advanced triple negative or BRCA1/2 breast cancer (CRUK/07/012)," Cancer Res. 2015;75(9 suppl):S3-01.
Têtu et al., "The influence of MMP-14, TIMP-2 and MMP-2 expression on breast cancer prognosis," Breast Cancer Res. 2006;8(3):R28.
Ulasov et al., "Inhibition of MMP14 potentiates the therapeutic effect of temozolomide and radiation in gliomas," Cancer Med. Aug. 2013;2(4):457-67.
U.S. Appl. No. 15/523,266, filed Apr. 28, 2017.
U.S. Appl. No. 16/838,367, filed Apr. 2, 2020.
U.S. Appl. No. 16/871,305, filed May 11, 2020.
Van Glabbeke et all., "Progression-free rate as the principal endpoint for phase II trials in soft-tissue sarcomas," Eur J Cancer. Mar. 2002;38(4):543-9.

(56) References Cited

OTHER PUBLICATIONS

Vandenbroucke and Libert, "Is there new hope for therapeutic matrix metalloproteinase inhibition?" Nat Rev Drug Discov. Dec. 2014;13(12):904-27.

Wang et al., "Co-expression of MMP-14 and MMP-19 predicts poor survival in human glioma," Clin Transl Oncol. Feb. 2013;15(2):139-45.

Wang et al., "MMP-14 overexpression correlates with poor prognosis in non-small cell lung cancer," Tumour Biol. Oct. 2014;35(10):9815-21.

Wang, "An exact mathematical expression fordescribing competitive binding of two different ligands to a protein molecule," FEBS Lett. Feb. 27, 1995;360(2):111-4.

Wind et al., "Measuring carbonic anhydrase IX as a hypoxia biomarker: differences in concentrations in serum and plasma using a commercial enzyme-linked immunosorbent assay due to influences of metal ions," Ann Clin Biochem. Mar. 2011;48(Pt 2):112-20.

Wu et al., "Structures of the CXCR4 chemokine GPCR with small-molecule and cyclic peptide antagonists," Science. Nov. 19, 2010;330(6007):1066-71.

Xiong et al., "Crystal structure of the extracellular segment of integrin alpha Vbeta3 in complex with an Arg-Gly-Asp ligand," Science. Apr. 5, 2002;296(5565):151-5.

Yardley et al., "EMERGE: A Randomized Phase II Study of the Antibody-Drug Conjugate Glembatumumab Vedotin in Advanced Glycoprotein NMB-Expressing Breast Cancer," J Clin Oncol. May 10, 2015;33(14):1609-19.

Yoshihara et al., "Tags for labeling protein N-termini with subtiligase for proteomics," Bioorg Med Chem Lett. Nov. 15, 2008;18(22):6000-3.

Zarrabi et al., "Inhibition of matrix metalloproteinase 14 (MMP-14)-mediated cancer cell migration," J Biol Chem. Sep. 23, 2011;286(38):33167-77.

Zhao et al., "Structural basis of specificity of a peptidyl urokinase inhibitor, upain-1," J Struct Biol. Oct. 2007;160(1):1-10.

Zhou et al., "Significance of semaphorin-3A and MMP-14 protein expression in non-small cell lung cancer," Oncol Lett. May 2014;7(5):1395-1400.

Zhu et al., "High-affinity peptide against MT1-MMP for in vivo tumor imaging," J Control Release. Mar. 30, 2011;150(3):248-55.

\* cited by examiner 17-69-N474

17-69-07-N470

17-69-07-N428

17-69-07-N473

17-69-07-N438

17-69-07-N443

17-69-07-N452

17-69-07-N479

17-69-07-N461

17-69-07-N474

17-69-07-N455

17-69-07-N471

17-69-07-N472

17-69-07-N454

17-69-07-N450

17-69-07-N451

PEPTIDE DERIVATIVES HAVING NOVEL LINKAGE STRUCTURES

SEQUENCE LISTING

The instant application contains a Sequence Listing which has been submitted electronically in ASCII format and is hereby incorporated by reference in its entirety. Said ASCII copy, created on Feb. 8, 2022, is named 168029_SL2.txt and is 28,840 bytes in size.

TECHNICAL FIELD

The present invention relates to peptides whose structure is constrained by covalently linking to a scaffold moiety which provides a more structured backbone, imparting a conformation to the peptide. In particular, the invention relates to novel chemistries for forming two or more bonds between a peptide and a scaffold molecule.

BACKGROUND OF THE INVENTION

Different research teams have previously tethered peptides to scaffold moieties by forming two or more thioether bonds between cysteine residues of the peptide and suitable functional groups of a scaffold molecule. For example, methods for the generation of candidate drug compounds by linking cysteine-containing peptides to a molecular scaffold as for example tris(bromomethyl)benzene are disclosed in WO 2004/077062 and WO 2006/078161.

The advantage of utilising cysteine thiols for generating covalent thioether linkages in order to achieve cyclisation resides is their selective and biorthogonal reactivity. Thiol-containing linear peptides may be cyclised with a thiol-reactive scaffold compound such as 1, 3, 5 tris-bromomethylbenzene (TBMB) to form Bicyclic Peptides, and the resultant product contains three thioethers at the benzylic locations. The overall reaction of the linear peptide with TBMB to form a looped bicyclic peptide with thioether linkages is shown in FIG. 1.

A need exists for alternative chemistries for coupling peptides to scaffold moieties to form looped peptide structures employing suitable replacements of the thioether moiety, thereby achieving compatibility with different peptides, changes in physiochemical properties such as improved solubility, alternative biodistribution and other advantages.

WO2011/018227 describes a method for altering the conformation of a first peptide derivative or group of peptide derivatives, each peptide derivative comprising at least two reactive groups separated by a loop sequence covalently linked to a molecular scaffold which forms covalent bonds with said reactive groups, to produce a second peptide derivative or group of peptide derivatives, comprising assembling said second derivative or group of derivatives from the peptide(s) and scaffold of said first derivative or group of derivatives, incorporating one of: (a) altering at least one reactive group; or (b) altering the nature of the molecular scaffold; or (c) altering the bond between at least one reactive group and the molecular scaffold; or any combination of (a), (b) or (c).

SUMMARY OF THE INVENTION

The present inventors have found that replacement of one or more of the cysteine residues in a looped peptide by peptides having side-chain amino groups offers an opportunity to generate looped peptide derivatives having alkylamino linkages replacing the thioether linkages of the prior art. The replacement of thioether linkages by alkylamino linkages is expected to result in improved solubility and/or improved oxidation stability of the looped peptide derivatives according to the present invention. The present inventors have found, surprisingly, that affinity of the derivatives to target molecules of interest can be conserved after replacement of thioether linkages by alkylamino linkages.

Accordingly, in a first aspect the present invention provides a compound comprising at least one looped peptide structure attached via at least one N-alkylamino linkage to a scaffold.

The term "alkylamino linkage" suitably refers to a linkage of general formula

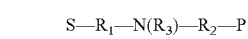

Wherein:
S represents the scaffold core, e.g. a (hetero)aromatic or (hetero)alicyclic ring as explained further below;
$R_1$ and $R_2$ are independently C1 to C3 alkylene groups, optionally substituted for example with 0-2 C1-C3 alkyl groups; suitably $R_1$ and $R_2$ are independently methylene or ethylene groups, and most suitably $R_1$ and $R_2$ are both methylene ($CH_2$);
$R_3$ is C1-4 alkyl including branched alkyl and cycloalkyl, for example methyl, or H, optionally substituted with one or more halogen atoms; and
P represents the peptide backbone, i.e. the $R_2$ moiety of the above linkage is linked to the carbon atom adjacent to a carboxylic carbon of the peptide backbone.

In embodiments, the looped peptide structure is further attached to the scaffold via at least one thioether linkage. The thioether linkage provides an anchor during formation of the cyclic peptides as explained further below. In these embodiments, there is preferably only one such thioether linkage. In these embodiments, there is suitably one such thioether linkage and two alkylamino linkages. Suitably, the thioether linkage is a central linkage of the bicyclic or polycyclic peptide derivative, i.e. in the peptide sequence two residues (e.g. diaminopropionic acid residues) forming the alkylamino linkages in the peptide are spaced from and located on either side of the amino acid residue (e.g. cysteine) forming the thioether linkage. Suitably, the looped peptide structure is therefore a Bicycle peptide compound having a central thioether linkage and two peripheral alkylamino linkages. In other embodiments comprising a thioether linkage, placement of the thioether bond can be at the N-terminus or at the C-terminus with two adjacent N-alkylamino linkages.

In other suitable embodiments, the looped peptide structure does not comprise any thioether linkage between the peptide and the scaffold. Suitably, in these embodiments, the peptide is attached to the scaffold only by the alkylamino linkages. Suitably, there are three alkylamino linkages spaced along the peptide chain, whereby the looped peptide structure is a Bicycle peptide compound having a central alkylamino linkage and two peripheral alkylamino linkages. In these embodiments, the alkylamino linkages are suitably formed with $R_3$=alkyl or haloalkyl in the formula above, since these linkages are formed with better reaction kinetics than the linkages with $R_3$=H.

Suitably, the scaffold comprises a (hetero)aromatic or (hetero)alicyclic moiety. Suitably, the scaffold comprises a tris-substituted (hetero)aromatic or (hetero)alicyclic moiety, for example a tris-methylene substituted (hetero)aromatic or (hetero)alicyclic moiety. The (hetero)aromatic or (hetero)alicyclic moiety is suitably a six-membered ring structure, preferably tris-substituted such that the scaffold has a 3-fold symmetry axis. Thus, in certain preferred embodiments, the scaffold is 1,3,5-tris-methylbenzene. In other preferred embodiments, the scaffold molecule is 1,3,5-tris-(acetamido)benzene, for exampled derived by reaction of the peptide with (bromoacetamido)benzene (TBAB).

Suitably, the alkylamino linkages are made through amino acid residues of the peptide having at least one —NH$_2$ or —NHR$_3$ group in a side chain thereof. These amino acid residues may be naturally occurring amino acids, or non-natural amino acids. In particular, the non-natural amino acids may be selected from 2,3-diaminopropionic acid (Dap) or β-N-alkyl-2,3-diaminopropionic acid (N-AlkDap) or β-N-haloalkyl-2,3-diaminopropionic acid (N-AlkDap). In this context, "alkyl" refers to C1-C4 alkyl, and is suitably methyl.

In a second aspect, the present invention provides a method of making a compound comprising at least one looped peptide structure attached via at least one alkylamino linkage to a scaffold, the method comprising: providing a peptide having at least one amino acid residues selected from diaminopropionic acid or β-N-(halo)alkyldiaminopropionic acid; providing a scaffold molecule having at least two reactive sites for forming alkylamino linkages with the side chain amino groups of the said diaminopropionic acid or β-N-(halo)alkyldiaminopropionic acid residues; and forming said alkylamino linkages between the peptide and the scaffold molecule.

In embodiments, the peptide further comprises at least one cysteine residue for forming a thioether linkage to the scaffold. In these embodiments, the peptide suitably has only one such cysteine residue. Suitably, the cysteine residue is located intermediate two diaminopropionic acid or β-N-Alkyldiaminopropionic acid residues on the peptide, whereby it forms a central linkage between two peptide loops of the derivative. The —SH group of cysteine is highly nucleophilic, and is expected to react first with the electrophilic centres of the scaffold molecule to anchor the peptide to the scaffold molecule, whereafter the amino groups react with the remaining electrophilic centres of the scaffold molecule to form the looped peptide derivative. In other embodiments, the central linkage is formed by a diaminopropionic acid or β-N-(halo)alkyldiaminopropionic acid residue and the peripheral linkages are formed by a cysteine and a diaminopropionic acid or β-N-(halo)alkyldiaminopropionic acid residue, respectively.

In other embodiments, the starting peptide does not include a cysteine residue. In these embodiments, the peptide suitably has three amino acid residues selected from diaminopropionic acid or β-N-(halo)alkyldiaminopropionic acid spaced along the chain for forming a Bicycle structure by reaction with the scaffold molecule. In these embodiments, the three amino acid residues are suitably selected from -(halo)alkyldiaminopropionic acid residues, for the reasons given above.

In embodiments, the starting peptide has protecting groups on nucleophilic groups other than the amino groups intended for forming the alkylamino linkages.

Suitably, the method of the invention comprises reacting, in a nucleophilic substitution reaction, the peptide having diaminopropionic acid or β-N-(halo)alkyldiaminopropionic acid residues with a scaffold molecule having two or more leaving groups.

The nucleophilic substitution reactions may be performed in the presence of a base, for example where the leaving group is a conventional anionic leaving group. The present inventors have found that the yields of cyclised peptide derivatives according to the invention can be greatly increased by suitable choice of solvent and base for the nucleophilic substitution reaction, and furthermore that the preferred solvent and base are different from the prior art solvent and base combinations that involve only the formation of thioether linkages. In particular, the present inventors have found that improved yields are achieved when using a trialkylamine base, i.e. a base of formula NR$_1$R$_2$R$_3$, wherein R$_1$, R$_2$ and R$_3$ are independently C1-C5 alkyl groups, suitably C2-C4 alkyl groups, in particular C2-C3 alkyl groups. Especially suitable bases are triethylamine and diisopropylethylamine (DIPEA). These bases have the property of being only weakly nucleophilic, and it is thought that this property accounts for the fewer side reactions and higher yields observed with these bases. The present inventors have further found that the preferred solvents for the nucleophilic substitution reaction are polar and protic solvents, in particular MeCN/H$_2$O (50:50).

In embodiments, the compound of the present invention is a drug conjugate comprising the looped peptide structure conjugated to one or more effector and/or functional groups such as a cytotoxic agent or a metal chelator.

Suitably, the conjugate has the cytotoxic agent linked to the looped peptide structure by a cleavable bond, such as a disulphide bond. Suitably, the cytotoxic agent is selected from DM1 or MMAE.

In embodiments, the drug conjugate has the following structure:

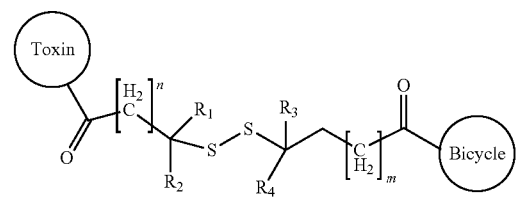

wherein: R$_1$, R$_2$, R$_3$ and R$_4$ represent hydrogen or C1-C6 alkyl groups;
Toxin refers to any suitable cytotoxic agent;
Bicycle represents the looped peptide structure;
n represents an integer selected from 1 to 10; and
m represents an integer selected from 0 to 10.

Suitably, either: R$_1$, R$_2$, R$_3$ and R$_4$ are all H; or R$_1$, R$_2$, R$_3$ are all H and R$_4$=methyl; or R$_1$, R$_2$=methyl and R$_3$, R$_4$=H; or R$_1$, R$_3$=methyl and R$_2$, R$_4$=H; or R$_1$, R$_2$=H and R$_3$, R$_4$=C1-C6 alkyl.

The linker between the toxin and the bicycle peptide may comprise a triazole group formed by click-reaction between an azide-functionalized toxin and an alkyne-functionalized bicycle peptide structure (or vice-versa). In other embodiments, the bicycle peptide may contain an amide linkage formed by reaction between a carboxylate-functionalized toxin and the N-terminal amino group of the bicycle peptide.

The linker between the toxin and the bicycle peptide may comprise a cathepsin-cleavable group to provide selective release of the toxin within the target cells. A suitable cathepsin-cleavable group is valine-citrulline.

The linker between the toxin and the bicycle peptide may comprise one or more spacer groups to provide the desired functionality, e.g. binding affinity or cathepsin cleavability, to the conjugate. A suitable spacer group is para-amino benzyl carbamate (PABC) which may be located intermediate the valine-citrulline group and the toxin moiety.

Thus, in embodiments, the bicycle peptide-drug conjugate may have the following structure made up of Toxin-PABC-cit-val-triazole-Bicycle:

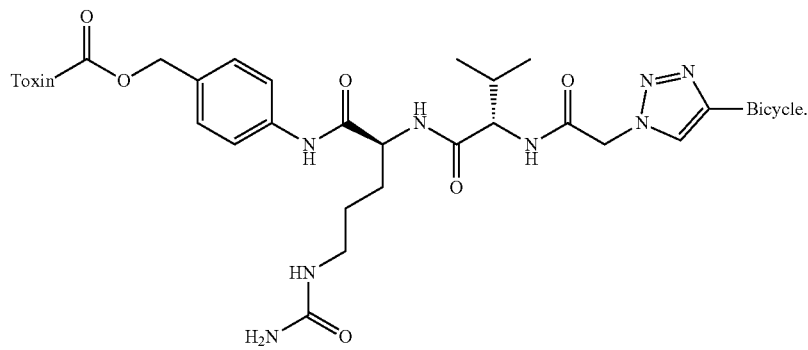

In further embodiments, the bicycle peptide-drug conjugate may have the following structure made up of Toxin-PABC-cit-val-dicarboxylate-Bicycle:

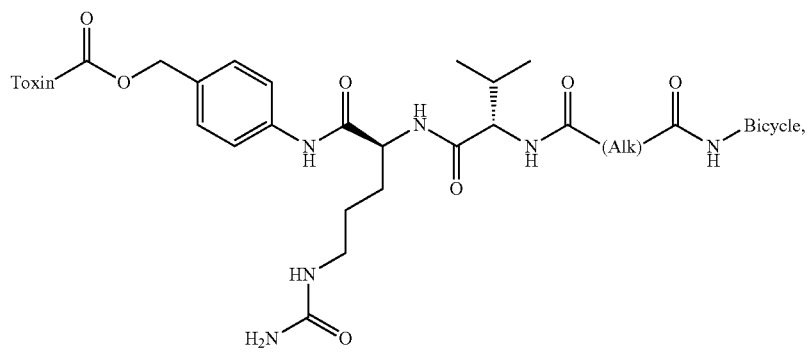

Wherein (alk) is an alkylene group of formula $C_nH_{2n}$ wherein n is from 1 to 10 and may be linear or branched, suitably (alk) is n-propylene or n-butylene.

In a further aspect, the present invention provides a library comprising a plurality of different compounds according to the invention. The different compounds may comprise different peptide sequences and/or different scaffolds. The library can be screened to identify compounds having a desired biological activity.

In a further aspect, the present invention provides a method for selecting a candidate drug compound, comprising: providing a library of compounds according to the first aspect of the invention, determining the binding of a target molecule to said compounds, and identifying a compound which maximally binds to said target molecule.

Screening may be carried out by analysis of individual molecules. Such methods are provided in WO 2004/077062, WO 2006/078161 and WO2011/018227.

In another aspect, the invention further provides a kit comprising at least a peptide derivative according to the present invention.

In a still further aspect, the present invention provides a composition comprising a peptide derivative of the present invention, and a pharmaceutically acceptable carrier, diluent or excipient.

Moreover, the present invention provides a method for the treatment of disease using a peptide derivative or a composition according to the present invention.

In a further aspect, the present invention provides a method for diagnosis, including diagnosis of disease, using a peptide derivative, or a composition according to the present invention. Thus in general the binding of an analyte to a peptide derivative may be exploited to displace an agent, which leads to the generation of a signal on displacement.

For example, binding of analyte (second target) can displace an enzyme (first target) bound to the peptide derivative providing the basis for a binding assay, especially if the enzyme is held to the peptide derivative through its active site.

DETAILED DESCRIPTION OF THE INVENTION

Figure 1:
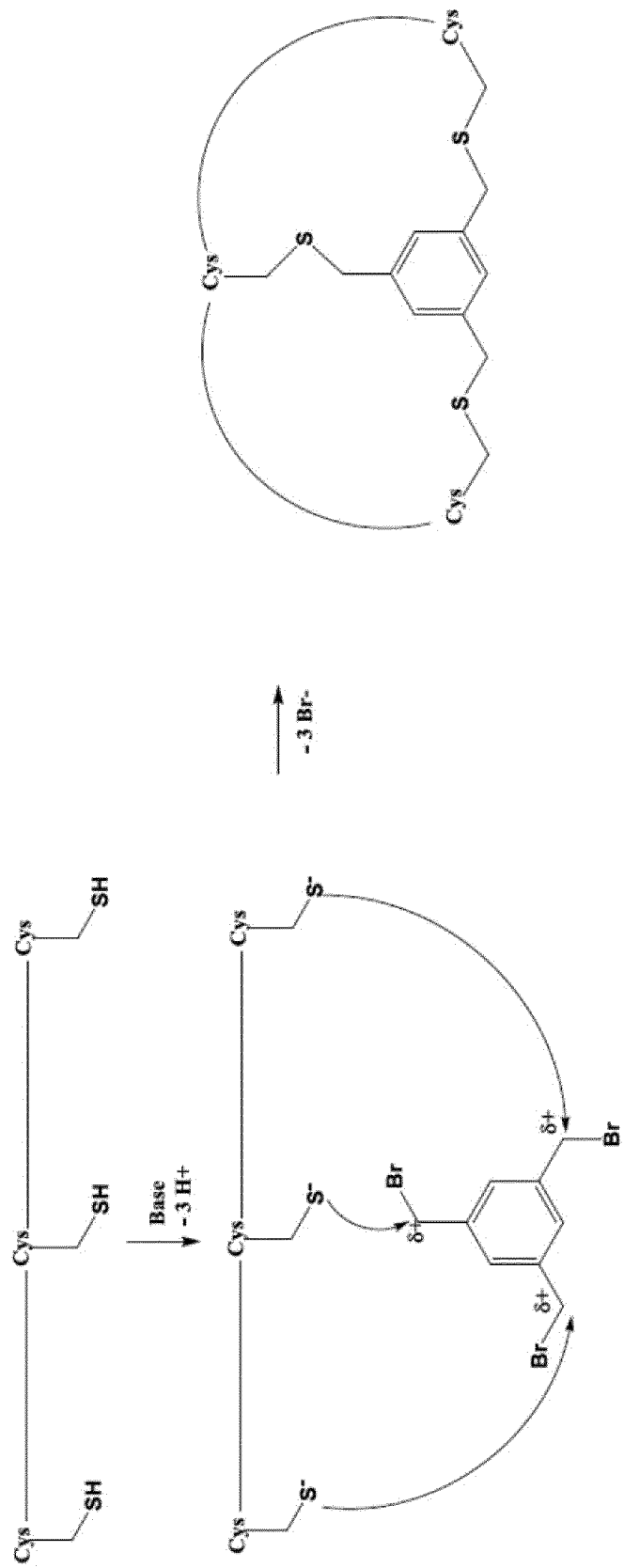
FIG. 1 shows a reaction scheme for preparation of thioether-linked bicyclic peptide ligands according to the prior art.

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4$^{th}$ ed., John Wiley & Sons, Inc.), which are incorporated herein by reference.

The present invention provides a compound comprising at least one looped peptide structure attached via at least one, preferably at least two, alkylamino linkages to a scaffold.

The looped peptide structure comprises at least one peptide loop subtended between two linkages on a molecular scaffold. Suitably, the looped peptide structure is a Bicycle structure, i.e. it comprises or consists of two peptide loops subtended between three linkages on the molecular scaffold, the central linkage being common to the two loops.

In embodiments, the looped peptide structure is further attached to the scaffold via a thioether linkage. Suitably, there is no more than one such thioether linkage. Suitably, the looped peptide structure is said Bicycle structure that forms two loops, subtended between the three linkages of which the central, common linkage is suitably the thioether linkage and the outer linkages are alkylamino linkages. However, it is envisaged that in other embodiments the thioether linkage may be one of the outer linkages.

In other embodiments, the looped peptide structure may be free of thioether linkages between the peptide and the scaffold structure. In these embodiments, the peptide may be linked to the scaffold only by alkylamino linkages. In these embodiments, the looped peptide structure is suitably said Bicycle structure that forms two loops, subtended between three linkages, each of which is an alkylamino linkage. In these embodiments, the alkylamino linkages are suitably formed from (halo)alkylDap.

The compounds of the invention thus comprise, consist essentially of, or consist of, a peptide covalently bound to a molecular scaffold. The term "scaffold" or "molecular scaffold" herein refers to a chemical moiety that is bonded to the peptide at the two or more alkylamino linkages in the compounds of the invention. The term "scaffold molecule" or "molecular scaffold molecule" herein refers to a molecule that is capable of being reacted with a peptide or peptide derivative to form the conjugate having alkylamino bonds. Thus, the scaffold molecule has the same structure as the scaffold moiety except that respective reactive groups (such as leaving groups) of the molecule are replaced by alkylamino bonds and optionally also a thioether bond to the peptide in the scaffold moiety.

The molecular scaffold molecule is any molecule which is able to connect the peptide at multiple points to form two or more alkylamino bonds to the peptide. It is not a cross-linker, in that it does not normally link two peptides; instead, it provides two or more attachment points for a single peptide. Preferably, the molecular scaffold molecule comprises at least three attachment points for the peptide, referred to as scaffold reactive groups. These groups are capable of reacting with amino groups on the peptide to form alkylamino linkages. Thus, the molecular scaffold represents the scaffold moiety up to but not including the alkylamino linkages in the conjugates of the invention. The scaffold molecule has the structure of the scaffold, but with reactive groups at the locations of the alkylamino bonds in the conjugate of the invention. The scaffold and/or the scaffold molecule suitably has a molecular weight of less than about 1000 daltons, in some cases less than about 500 daltons, for example less than about 300 daltons.

Suitably, the scaffold comprises, consists essentially of, or consists of a (hetero)aromatic or (hetero)alicyclic moiety.

As used herein, "(hetero)aryl" is meant to include aromatic rings, for example, aromatic rings having from 4 to 12 members, such as phenyl rings. These aromatic rings can optionally contain one or more heteroatoms (e.g., one or more of N, O, S, and P), such as thienyl rings, pyridyl rings, and furanyl rings. The aromatic rings can be optionally substituted. "(hetero)aryl" is also meant to include aromatic rings to which are fused one or more other aryl rings or non-aryl rings. For example, naphthyl groups, indole groups, thienothienyl groups, dithienothienyl, and 5,6,7,8-tetrahydro-2-naphthyl groups (each of which can be optionally substituted) are aryl groups for the purposes of the present application. As indicated above, the aryl rings can be optionally substituted. Suitable substituents include alkyl groups (which can optionally be substituted), other aryl groups (which may themselves be substituted), heterocyclic rings (saturated or unsaturated), alkoxy groups (which is meant to include aryloxy groups (e.g., phenoxy groups)), hydroxy groups, aldehyde groups, nitro groups, amine groups (e.g., unsubstituted, or mono- or di-substituted with aryl or alkyl groups), carboxylic acid groups, carboxylic acid derivatives (e.g., carboxylic acid esters, amides, etc.), halogen atoms (e.g., Cl, Br, and I), and the like.

As used herein, "(hetero)alicyclic" refers to a homocyclic or heterocyclic saturated ring. The ring can be unsubstituted, or it can be substituted with one or more substituents. The substituents can be saturated or unsaturated, aromatic or nonaromatic, and examples of suitable substituents include those recited above in the discussion relating to substituents on alkyl and aryl groups. Furthermore, two or more ring substituents can combine to form another ring, so that "ring", as used herein, is meant to include fused ring systems.

Suitably, the scaffold comprises a tris-substituted (hetero) aromatic or (hetero)alicyclic moiety, for example a tris-methylene substituted (hetero)aromatic or (hetero)alicyclic moiety. The (hetero)aromatic or (hetero)alicyclic moiety is suitably a six-membered ring structure, preferably tris-substituted such that the scaffold has a 3-fold symmetry axis.

In embodiments, the scaffold is a tris-methylene (hetero) aryl moiety, for example a 1,3,5-tris methylene benzene moiety. In these embodiments, the corresponding scaffold molecule suitably has a leaving group on the methylene carbons. The methylene group then forms the $R_1$ moiety of the alkylamino linkage as defined herein. In these methylene-substituted (hetero)aromatic compounds, the electrons of the aromatic ring can stabilize the transition state during nucleophilic substitution. Thus, for example, benzyl halides are 100-1000 times more reactive towards nucleophilic substitution than alkyl halides that are not connected to a (hetero)aromatic group.

In these embodiments the scaffold and scaffold molecule have the general formula:

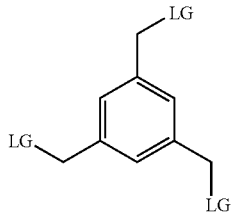

Where LG represents a leaving group as described further below for the scaffold molecule, or LG (including the adjacent methylene group forming the $R_1$ moiety of the alkylamino group) represents the alkylamino linkage to the peptide in the conjugates of the invention.

In embodiments, the group LG above may be a halogen such as, but not limited to, a bromine atom, in which case the scaffold molecule is 1,3,5-Tris(bromomethyl)benzene (TBMB). Another suitable molecular scaffold molecule is 2,4,6-tris(bromomethyl) mesitylene. It is similar to 1,3,5-tris(bromomethyl) benzene but contains additionally three methyl groups attached to the benzene ring. In the case of this scaffold, the additional methyl groups may form further contacts with the peptide and hence add additional structural constraint. Thus, a different diversity range is achieved than with 1,3,5-Tris(bromomethyl)benzene.

Another preferred molecule for forming the scaffold for reaction with the peptide by nucleophilic substitution is 1,3,5-tris(bromoacetamido)benzene (TBAB):

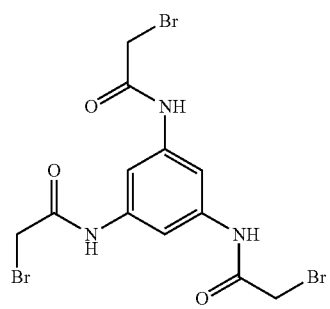 [SMILES: O=C(CBr)Nc1cc(NC(=O)CBr)cc(NC(=O)CBr)c1]

In yet other embodiments the molecular scaffold may have a tetrahedral geometry such that reaction of four functional groups of the encoded peptide with the molecular scaffold generates not more than two product isomers. Other geometries are also possible; indeed, an almost infinite number of scaffold geometries is possible, leading to greater possibilities for peptide derivative diversification.

Typically, the groups forming alkylamino bonds are present on amino acid side chains on the peptide. The groups are suitably primary or secondary amine groups. Preferred are the primary —$CH_2NH_2$ groups of suitable artificial amino acids such as diaminopropionic acid (DAP) or secondary —$CH_2NHR_3$ amino groups such as β-N-Alkyldiaminopropionic acid (N-AlkDap) or β-N-haloalkyldiaminopropionic acid (N-HAlkDap). The structure of diaminopropionic acid is analogous to that of cysteine that has been used to form thioether bonds to the scaffold in the prior art, with replacement of the terminal —SH group of cysteine by —$NH_2$:

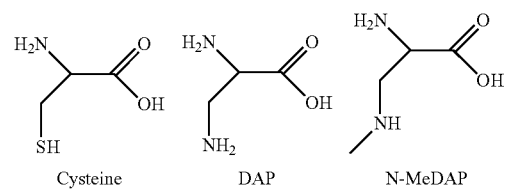

The term "alkylamino" is used herein in its normal chemical sense to denote a linkage consisting of NH or N($R_3$) bonded to two carbon atoms, wherein the carbon atoms are independently selected from alkyl, alkylene, or aryl carbon atoms and $R_3$ is an alkyl or haloalkyl group, suitably containing from 1 to 4 carbon atoms. Suitably, the alkylamino linkages of the invention comprise an NH moiety bonded to two saturated carbon atoms, most suitably methylene (—$CH_2$—) carbon atoms. In embodiments, the alkylamino linkages of the invention have general formula:

Wherein:
S represents the scaffold core, e.g. a (hetero)aromatic or (hetero)alicyclic ring as explained further below;
$R_1$ and $R_2$ are independently C1 to C3 alkylene groups, optionally substituted for example with 0-2 C1-C3 alkyl groups; suitably $R_1$ and $R_2$ are independently methylene or ethylene groups, and most suitably $R_1$ and $R_2$ are both methylene ($CH_2$);
$R_3$ is H or C1-4 alkyl including branched alkyl and cycloalkyl, for example methyl, optionally substituted with one or more halogen atoms; and P represents the peptide backbone, i.e. the $R_2$ moiety of the above linkage is linked to the carbon atom in the peptide backbone adjacent to a carboxylic carbon of the peptide backbone.

The peptide element of the peptide conjugate of the invention comprises the two or more reactive groups, preferably three or more reactive groups, which are responsible for binding to the scaffold; and loop amino acid sequences between the reactive groups. Diversity can be obtained, as in the prior art, by varying the sequence of the loops.

A particular advantage of the peptide derivatives of the invention is that they are smaller than e.g. immunological binding agents of the prior art. Typically, a compound of the present invention has a molecular weight of less than about 5000 Dalton; preferably less than about 4000 Dalton; and preferably less than about 3000 Dalton. It will be understood that a derivative constructed with further peptide sequences extending from either or both ends of the loops may have a higher molecular weight outside these ranges. Moreover, peptide derivatives bound to molecules such as cytotoxic or therapeutic agents, HSA or polyethyleneglycol (PEG) polymers will have a much higher molecular weight.

The small size of the compounds of the invention results from the use of small molecular scaffolds, typically up to about 500 Dalton in mass. The peptide itself is preferably less than about 27 amino acids in length, as measured between the N-terminal and C-terminal attachment points which attach it to the molecular scaffold. Further peptides may, of course, be present or be attached outside of the attachment points, lengthening the peptide structure. Each loop of the peptide is preferably between 0 and 9 amino acids in length, measured between adjacent attachment points. Advantageously, the loops in any peptide derivative are independently 3, 4, 5, 6, 7, 8 or 9 amino acids in length.

Several looped peptides may be incorporated together into the same molecule according to the present invention. For example, two such looped peptides of the same specificity can be linked together via the molecular scaffold, increasing the avidity of the derivative for its targets. Alternatively, in another embodiment a plurality of looped peptides are combined to form a multimer. For example, two different looped peptides are combined to create a multispecific molecule. Alternatively, three or more looped peptides, which may be the same or different, can be combined to form multispecific derivatives. In one embodiment multivalent complexes may be constructed by linking together the molecular scaffolds, which may be the same or different.

The peptide comprises a molecular scaffold binding segment. This is the region to which the molecular scaffold is attached. Suitably the commentary regarding reactive groups on the peptide is applied to this binding segment. Suitably the molecular scaffold binding segment of the target peptide comprises 1 to 27 amino acid residues, suitably 5 to 20 amino acid residues. Suitably the molecular scaffold binding segment of the target peptide comprises fewer than 15 amino acids. This has the advantage of imposing further conformational constraint onto the peptide segment when it is attached to the molecular scaffold.

The target peptide suitably comprises the sequence $(X)_i A_1 (X)_m A_2 (X)_n A_3 (X)_o$, wherein: $A_1$, $A_2$ and $A_3$ are selected from cysteine, Dap, N-AlkDap or N-HAlkDap, provided that at least one of $A_1$, $A_2$ and $A_3$ is Dap, N-AlkDap or N-HAlkDap; X represents a random amino acid; m and n are numbers between 1 and 20, preferably between 4 and 10, defining the length of intervening peptide segments; and 1 and o are numbers between 0 and 20 defining the length of the flanking peptide segments. In certain embodiment, the peptide can suitably comprise the sequence $(X)_i A_1 (X)_m A_2 (X)_n A_3 (X)_o$ or $(X)_i A_1 (X)_m A_2 (X)_n A_3 (X)_o$. As previously discussed, suitably at least two of $A_1$, $A_2$ and $A_3$ is Dap, N-AlkDap or N-HAlkDap. In embodiments, one of $A_1$, $A_2$ and $A_3$ is cysteine and the others are Dap, N-AlkDap or N-HAlkDap.

In certain embodiments wherein the looped bicycle ligands bind with high affinity to the cell surface metalloprotease MT1-MMP, the peptide comprises an amino acid sequence of formula (II):

(II)
(SEQ ID NO: 1)
$-A_1-X_1-U/O_2-X_3-X_4-G_5-A_2-E_6-D_7-F_8-Y_9-X_{10}-X_{11}-A_2-$ or a pharmaceutically acceptable salt thereof;
wherein:
$A_1$, $A_2$ and $A_3$ are as defined above; X represents any amino acid residue;
U represents a polar, uncharged amino acid residue selected from N, C, Q, M, S and T; and
O represents a non-polar aliphatic amino acid residue selected from G, A, I, L, P and V.

It can be seen that these derivatives of the invention comprise a peptide loop coupled to a scaffold by two alkylamino linkages to Dap or N-AlkDap or N-HAlkDap residues and a third linkage selected from a thioether linkage to cysteine or an alkylamino linkages to Dap or N-AlkDap. The thioether linkage, where present, may provide an anchor during formation of the cyclic peptides as explained further below. The thioether linkage, where present, may be a central linkage of the bicyclic peptide conjugate, i.e. in the peptide sequence the two residues forming the alkylamino linkages in the peptide are spaced from and located on either side of the cysteine residue forming the thioether linkage. The looped peptide structure is therefore a Bicycle peptide conjugate having a central thioether or alkylamino linkage and peripheral alkylamino or thioether linkages as illustrated in the examples of the present application.

Suitably, $X_1$ is selected from any one of the following amino acids: Y, M, F or V, such as Y, M or F, in particular, Y or M, more particularly Y.

Suitably, $U/O_2$ is selected from a U, such as an N, or an O, such as a G.

Suitably, $X_3$ is selected from U or Z, wherein U represents a polar, uncharged amino acid residue selected from N, C, Q, M, S and T and Z represents a polar, negatively charged amino acid residue selected from D or E, in particular the U at position 3 is selected from Q or the Z at position 3 is selected from E.

Suitably, $X_4$ is selected from J, wherein J represents a non-polar aromatic amino acid residue selected from F, W and Y.

Suitably, $X_{10}$ is selected from Z, wherein Z represents a polar, negatively charged amino acid residue selected from D or E, such as D.

Suitably, $X_{11}$ is selected from 0, wherein 0 represents a non-polar aliphatic amino acid residue selected from G, A, I, L, P and V, such as I.

Suitably, the Bicycle of formula (II) is a compound of formula (IIa):

(IIa)
(SEQ ID NO: 6)
$-A_1-Y/M/F/V-U/O-U/Z-J-G-A_2-E-D-F-Y-Z-O-A_3-$ wherein U, O, J and Z are as defined hereinbefore; or
a compound of formula (IIb):

(IIb)
(SEQ ID NO: 7)
-A$_1$-Y/M/F/V-N/G-E/Q-F-G-A$_2$-E-D-F-Y-D-I-A$_3$-;

or
a compound of formula (IIc):

(IIc)
(SEQ ID NO: 8)
-A$_1$-Y/M/F-N/G-E/Q-F-G-A$_2$-E-D-F-Y-D-I-A$_3$-;

or
a compound of formula (IId):

(IId)
(SEQ ID NO: 9)
-A$_1$-Y/M-N-E/Q-F-G-A$_2$-E-D-F-Y-D-I-A$_3$-;

or
a compound of formula (IIe):

(IIe)
(SEQ ID NO: 2)
-A$_1$-Y-N-E-F-G-A$_2$-E-D-F-Y-D-I-A$_3$-
(17-69-07).

Suitably, the Bicycle of formula (II) comprises a sequence selected from:

(SEQ ID NO: 2)
-A$_1$-Y-N-E-F-G-A$_2$-E-D-F-Y-D-I-A$_3$-
(17-69-07);

(SEQ ID NO: 10)
-A$_1$-M-N-Q-F-G-A$_2$-E-D-F-Y-D-I-A$_3$-
(17-69-12);

(SEQ ID NO: 11)
-A$_1$-F-G-E-F-G-A$_2$-E-D-F-Y-D-I-A$_3$-
(17-69-02);

(SEQ ID NO: 12)
-A$_1$-V-N-E-F-G-A$_2$-E-D-F-Y-D-I-A$_3$-
(17-69-03);

(SEQ ID NO: 13)
-A$_1$-F-N-E-F-G-A$_2$-E-D-F-Y-D-I-A$_3$-
(17-69-04);

(SEQ ID NO: 14)
-A$_1$-Y-N-E-Y-G-A$_2$-E-D-F-Y-D-I-A$_3$-
(17-69-07-N057);
and (SEQ ID NO: 15)
-A$_1$-Y-N-E-W-G-A$_2$-E-D-F-Y-D-I-A$_3$-
(17-69-44-N002), such as:

(SEQ ID NO: 2)
-A$_1$-Y-N-E-F-G-A$_2$-E-D-F-Y-D-I-A$_3$-
(17-69-07);
and (SEQ ID NO: 10)
-A$_1$-M-N-Q-F-G-A$_2$-E-D-F-Y-D-I-A$_3$-
(17-69-12), in particular:

(SEQ ID NO: 2)
-A$_1$-Y-N-E-F-G-A$_2$-E-D-F-Y-D-I-A$_3$-
(17-69-07), most particularly:
the Dap homologues of 17-69-07-N241 designated as SEQ ID 16: ((bAla)-Sar10-AA$_1$(D-Ala)NE(1NaI)(D-Ala)A$_2$EDFYD(tBuGly)A$_3$;
and the Dap homologues of 17-69-07-N268 designated as SEQ ID 17: AA$_1$(D-Ala)NE(1NaI)(D-Ala)A$_2$EDFYD(tBuGly)A$_3$.

In all of the above sequences, A$_1$, A$_2$, and A$_3$ are as hereinbefore defined. Suitable and preferred types and positions of A$_1$, A$_2$, and A$_3$ are as hereinbefore defined.

In these and other embodiments of the invention, the peptide ligand may additionally comprises one or more modifications selected from: N-terminal and/or C-terminal modifications; replacement of one or more amino acid residues with one or more non-natural amino acid residues (such as replacement of one or more polar amino acid residues with one or more isosteric or isoelectronic amino acids; replacement of one or more hydrophobic amino acid residues with other non-natural isosteric or isoelectronic amino acids); addition of a spacer group; replacement of one or more oxidation sensitive amino acid residues with one or more oxidation resistant amino acid residues; replacement of one or more amino acid residues with an alanine, replacement of one or more L-amino acid residues with one or more D-amino acid residues; N-alkylation of one or more amide bonds within the bicyclic peptide ligand; replacement of one or more peptide bonds with a surrogate bond; peptide backbone length modification; substitution of the hydrogen on the α-carbon of one or more amino acid residues with another chemical group, and post-synthetic bioorthogonal modification of amino acids such as cysteine, lysine, glutamate and tyrosine with suitable amine, thiol, carboxylic acid and phenol-reactive reagents.

Suitably, these embodiments may comprise an N-terminal modification using suitable amino-reactive chemistry, and/or C-terminal modification using suitable carboxy-reactive chemistry. For example, the N-terminal modification may comprise the addition of a molecular spacer group which facilitates the conjugation of effector groups and retention of potency of the bicyclic peptide to its target. The spacer group is suitably an oligopeptide group containing from about 5 to about 30 amino acids, such as an Ala, G-Sar10-A group or bAla-Sar10-A group. Alternatively or additionally, the N-terminal and/or C-terminal modification comprises addition of a cytotoxic agent.

Further details of these MT1-MMP binding peptides can be found in our copending published application WO2016/067035 and pending application GB1607827.1 filed on 4 May 2016. The entire disclosure of these applications is expressly incorporated herein by reference.

In a second aspect, the present invention provides a method of making a compound comprising at least one looped peptide structure attached via at least one, for example at least two, alkylamino linkages to a scaffold, the method comprising: providing a peptide having at least one diaminopropionic acid or β-N-(halo)alkyldiaminopropionic acid residues; providing a scaffold molecule having at least two reactive sites for forming alkylamino linkages with the amino groups of the diaminopropionic acid or β-N-Alkyldiaminopropionic acid residues; and forming said alkylamino linkages between the peptide and the scaffold molecule.

Suitably, the methods according to this aspect of the invention are directed to making compounds according to the first aspect of the invention. Accordingly, the details of the scaffold molecule and the peptide are suitably as described above in relation to the first aspect of the invention.

The peptides for use in the methods of the invention can be made using conventional solid-phase synthesis from amino acid starting materials, which may include appropriate protecting groups as described herein. These methods for making peptides are well known in the art.

In embodiments, the peptide has protecting groups on nucleophilic groups other than the amine groups or —SH group intended for forming the alkylamino linkages or thioether linkages (where present). The nucleophilicity of amino acid side chains has been subject to several studies, and listed in descending order: thiolate in cysteines, amines in Lysine, secondary amine in Histidine and Tryptophan, guanidino amines in Arginine, hydroxyls in Serine/Threonine, and finally carboxylates in aspartate and glutamate. Accordingly, it is necessary to apply protecting groups to the more nucleophilic groups on the peptide to prevent undesired side reactions with these groups.

Suitably, the method of the invention comprises reacting, in a nucleophilic substitution reaction, the peptide having two or more reactive side chain amine groups, with a scaffold molecule having two or more leaving groups.

The term "leaving group" herein is used in its normal chemical sense to mean a moiety capable of nucleophilic displacement by an amine group. Any such leaving group can be used here provided it is readily removed by nucleophilic displacement by amine. Suitable leaving groups are conjugate bases of acids having a pKa of less than about 5. Non-limiting examples of leaving groups useful in the invention include halo, such as bromo, chloro, iodo, O-tosylate (OTos), O-mesylate (OMes), O-triflate (OTf) or O-trimethylsilyl (OTMS).

The nucleophilic substitution reactions may be performed in the presence of a base, for example where the leaving group is a conventional anionic leaving group. The present inventors have found that the yields of cyclised peptide derivatives can be greatly increased by suitable choice of solvent and base for the nucleophilic substitution reaction, and furthermore that the preferred solvent and base are different from the prior art solvent and base combinations that involve only the formation of thioether linkages. In particular, the present inventors have found that improved yields are achieved when using a trialkylamine base, i.e. a base of formula $NR_1R_2R_3$, wherein $R_1$, $R_2$ and $R_3$ are independently C1-C5 alkyl groups, suitably C2-C4 alkyl groups, in particular C2-C3 alkyl groups. Especially suitable bases are triethylamine and diisopropylethylamine (DIPEA). These bases have the property of being only weakly nucleophilic, and it is thought that this property accounts for the fewer side reactions and higher yields observed with these bases. The present inventors have further found that the preferred solvents for the nucleophilic substitution reaction are polar and protic solvents, in particular MeCN/$H_2O$ containing MeCN and $H_2O$ in volumetric ratios from 1:10 to 10:1, suitably from 2:10 to 10:2 and more suitably from 3:10 to 10:3, in particular from 4:10 to 10:4.

In a further aspect, the present invention provides a library comprising a plurality of different compounds according to the invention. The different compounds may comprise different peptide sequences and/or different scaffolds. The library can be screened to identify compounds having a desired biological activity.

The library may comprise or consist of, for example, at least about 10, 100 or 1000 different peptide conjugates according to the invention. Suitably, the library may consist of peptide conjugates each having the same scaffold structure but different peptides attached thereto.

In a further aspect, the present invention provides a method for selecting a candidate drug compound, comprising: providing a chemical library of compounds according to the above aspect of the invention, determining the binding of a target molecule to said compounds, and identifying a compound which maximally binds to said target molecule.

A target is a molecule or part thereof to which the peptide derivatives bind. Suitably, the compound of the invention binds selectively to a biological target. For example, it may bind with an affinity greater than about Kd=1000, suitably greater than about Kd=100, for example greater than about Kd=10 as determined by the method described herein. Typically, the target will be analogous to an epitope. One skilled in the art will appreciate that the choice of target molecule is large and varied. They may be for instance human or animal proteins, cytokines, cytokine receptors, enzymes co-factors for enzymes or DNA binding proteins. Suitable cytokines and growth factors include but are not limited to: ApoE, Apo-SAA, BDNF, Cardiotrophin-1, EGF, EGF receptor, ENA78, Eotaxin, Eotaxin-2, Exodus-2, FGF-acidic, FGF-basic, fibroblast growth factor-10 (30). FLT3 derivative, Fractalkine (CX3C), GDNF, G-CSF, GM-CSF, GF-1, insulin, IFNy, IGF-I, IGF-II, IL-1a, IL-1 (3, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-17a, IL-17c, IL-17d, IL-17e, IL-17f, IL-18 (IGIF), IL-21, IL-22, IL-23, IL-31, IL-32, IL-33, IL-34, Inhibin a, Inhibin P, IP-10, keratinocyte growth factor-2 (KGF-2), KGF, Leptin, LIF, Lymphotactin, Mullerian inhibitory substance, monocyte colony inhibitory factor, monocyte attractant protein (30 ibid), M-CSF, MDC (67 a. a.), MDC (69 a. a.), MCP-1 (MCAF), MCP-2, MCP-3, MCP-4, MDC (67 a. a.), MDC (69 a. a.), MIG, MIP-la, MIP-ip, MIP-3a, MIP3 (3, MIP-4, myeloid progenitor inhibitor factor-1 (MPIF-1), NAP-2, Neurturin, Nerve growth factor, P-NGF, NT-3, NT-4, Oncostatin M, PDGF-AA, PDGF-AB, PDGF-BB, PF-4, RANTES, SDFla, SDFlp, SCF, SCGF, stem cell factor (SCF), TARC, TGF-α, TGF-β, TGF-2, TGF-3, tumour necrosis factor (TNF), TNF-α, TNF-β, TNF receptor I, TNF receptor II, TNIL-1, TPO, VEGF, VEGF receptor 1, VEGF receptor 2, VEGF receptor 3, GCP-2, GRO/MGSA, GRO-☐, GRO-☐, HCC1, 1-309, HER 1, HER 2, HER 3 and HER 4. Cytokine receptors include receptors for the foregoing cytokines. Chemokine targets include CC chemokine derivatives CCL21/6Ckine, CCL12/MCP-5, CCL6/C10, CCL22/MDC, CCL14/HCC-1/HCC-3, CCL3L1/MIP-1 alpha Isoform LD78 beta, CCL23/Ck beta 8-1, CCL3/MIP-1 alpha, CCL28, CCL4L1/LAG-1, CCL27/CTACK, CCL4/MIP-1 beta, CCL24/Eotaxin-2/MPIF-2, CCL15/MIP-1 delta, CCL26-like/Eotaxin-3-like, CCL9/10/MIP-1 gamma, CCL26/Eotaxin-3, CCL19/MIP-3 beta, CCL11/Eotaxin, CCL20/MIP-3 alpha, CCL14a/HCC-1, CCL23/MPIF-1, CCL14b/HCC-3, CCL18/PARC, CCL16/HCC-4, CCL5/RANTES, CCL1/I-309/TCA-3, TAFA1/FAM19A1, MCK-2, TAFA5/FAM19A5, CCL2/JE/MCP-1, TAFA3/FAM19A3, CCL8/MCP-2, TAFA4/FAM19A4, CCL7/MCP-3/MARC, CCL17/TARC, CCL13/MCP-4 and CCL25/TECK; chemokine receptors include CCR1, CCR7, CCR2, CCR8, CCR3, CCR9, CCR4, CCR10, CCR5, CCRL2/LCCR/CRAM-A/B and CCR6; CXC chemokine derivatives include CXCL13/BLC/BCA-1, CXCL10/IP-10/CRG-2, CXCL14/BRAK, LIX, CXCL16, CXCL15/Lungkine, CXCL5/ENA-78, CXCL9/MIG, CXCL6/GCP-2, CXCL7/NAP-2, CXCL1/2/3/GRO, CXCL4/PF4, CXCL1/GRO alpha/KC/CINC-1, CXCL12/SDF-1 alpha, CXCL2/GRO beta/MIP-2/CINC-3, CXCL12/SDF-1 beta, CXCL3/GRO gamma/CINC-2/DCIP-1, CXCL12/SDF-1, CXCL11/I-TAC, CXCL7/Thymus Chemokine-1 and CXCL8/IL-8; CXC chemokine receptors include CXCR3, CXCR7/RDC-1, CXCR4, CXCR1/IL-8 RA, CXCR5, CXCR2/IL-8 RB and CXCR6; TNF Superfamily derivatives include 4-1BB Derivative/TNFSF9, LIGHT/TNFSF14, APRIL/TNFSF13, Lymphotoxin, BAFF/BLyS/TNFSF13B, Lymphotoxin beta/TNFSF3, CD27 Derivative/TNFSF7, OX40 Derivative/TNFSF4, CD30 Derivative/TNFSF8, TL1A/TNFSF15, CD40 Derivative/TNFSF5, TNF-alpha/TNFSF1A, EDA (pan), TNF-beta/TNFSF1B, EDA-A1/Ectodysplasin A1, TRAIL/TNFSF10, EDA-A2, TRANCE/TNFSF11, Fas Derivative/TNFSF6, TWEAK/TNFSF12 and GITR Derivative/TNFSF18; TNF Superfamily receptors include 4-1BB/TNFRSF9/CD137, NGF R/TNFRSF16, BAFF R/TNFRSF13C, Osteoprotegerin/TNFRSF11B, BCMA/TNFRSF17, OX40/TNFRSF4, CD27/TNFRSF7, RANK/TNFRSF11A, CD30/TNFRSF8, RELT/TNFRSF19L, CD40/TNFRSF5, TACI/TNFRSF13B, DcR3/TNFRSF6B, TNFRH3/TNFRSF26, DcTRAIL R1/TNFRSF23, TNF R1/TNFRSF1A, DcTRAIL R2/TNFRSF22, TNF RII/TNFRSF1B, DR3/TNFRSF25, TRAIL R1/TNFRSF10A, DR6/TNFRSF21, TRAIL R2/TNFRSF10B, EDAR, TRAIL R3/TNFRSF10C, Fas/TNFRSF6/CD95, TRAIL R4/TNFRSF10D, GITR/TNFRSF18, TROY/TNFRSF19, HVEM/TNFRSF14, TWEAK R/TNFRSF12, Lymphotoxin beta R/TNFRSF3 and XEDAR; Toll-Like Receptors including TLR-1, TLR-2, TLR-3, TLR-4, TLR-5, TLR-6, TLR-7, TLR-8 and TLR-9; enzymes, including Cathepsin A, Cathepsin B, Cathepsin C, Cathepsin D, Cathepsin E, Cathepsin F, MMP 1, MMP2, MMP 3, MMP 7, MMP 8, MMP 9, MMP 10, MMP 11, MMP 12, MMP 13, MMP 14, MMP 15, MMP 16, MMP 17, MMP 19, MMP 20, MMP 21, MMP 23A, MMP 23B, MMP 26, MMP 27, MMP 28, urokinase, kallikreins, including KLK1, KLK2, KLK3, KLK4, KLK5, KLK6, KLK7, KLK8, KLK9, KLK10, KLK11, KLK12, KLK13, KLK14 and KLK15; components of the complement system; Intracellular signalling molecules and transcription factors; p53; and MDM2. Targets may also be large plasma proteins, such as serum albumins, as set forth below.

It will be appreciated that this list is by no means exhaustive.

Additional binding or functional activities may be attached to the N or C terminus of the peptide covalently linked to a molecular scaffold. The functional group may, for example, be selected from the group consisting of: a group capable of binding to a molecule which extends the half-life of the peptide derivative in vivo, and a molecule which extends the half-life of the peptide derivative in vivo. Such a molecule can be, for instance, HSA or a cell matrix protein, and the group capable of binding to a molecule which extends the half-life of the peptide derivative in vivo is an antibody or antibody fragment specific for HSA or a cell matrix protein. Such a molecule may also be a conjugate with high molecular weight PEGs.

In one embodiment, the functional group is a binding molecule, selected from the group consisting of a second peptide derivative comprising a peptide covalently linked to a molecular scaffold, and an antibody or antibody fragment. 2, 3, 4, 5 or more peptide derivatives may be joined together.

The specificities of any two or more of these derivatives may be the same or different; if they are the same, a multivalent binding structure will be formed, which has increased avidity for the target compared to univalent binding molecules. The molecular scaffolds, moreover, may be the same or different, and may subtend the same or different numbers of loops.

The functional group can moreover be an effector group, for example an antibody Fc region.

Attachments to the N or C terminus may be made prior to binding of the peptide to a molecular scaffold, or afterwards. Thus, the peptide may be produced (synthetically, or by biologically derived expression systems) with an N or C terminal peptide group already in place. Preferably, however, the addition to the N or C terminus takes place after the peptide has been combined with the molecular backbone to form a conjugate. For example, Fluorenylmethyloxycarbonyl chloride can be used to introduce the Fmoc protective group at the N-terminus of the peptide. Fmoc binds to serum albumins including HSA with high affinity, and Fmoc-Trp or Fmoc-Lys bind with an increased affinity. The peptide can be synthesised with the Fmoc protecting group left on, and then coupled with the scaffold through the alkylaminos. An alternative is the palmitoyl moiety which also binds HSA and has, for example been used in Liraglutide to extend the half-life of this GLP-1 analogue.

Alternatively, a conjugate of the peptide with the scaffold can be made, and then modified at the N-terminus, for example with the amine- and sulfhydryl-reactive linker N-e-maleimidocaproyloxy) succinimide ester (EMCS). Via this linker the peptide conjugate can be linked to other peptides, for example an antibody Fc fragment.

The binding function may be another peptide bound to a molecular scaffold, creating a multimer; another binding protein, including an antibody or antibody fragment; or any other desired entity, including serum albumin or an effector group, such as an antibody Fc region.

Additional binding or functional activities can moreover be bound directly to the molecular scaffold. In embodiments, the scaffold may further comprise a reactive group to which the additional activities can be bound. Preferably, this group is orthogonal with respect to the other reactive groups on the molecular scaffold, to avoid interaction with the peptide. In one embodiment, the reactive group may be protected, and deprotected when necessary to conjugate the additional activities. Accordingly, in a further aspect of the invention, there is provided a drug conjugate comprising a peptide ligand as defined herein conjugated to one or more effector and/or functional groups.

Effector and/or functional groups can be attached, for example, to the N or C termini of the polypeptide, or to the molecular scaffold.

Appropriate effector groups include antibodies and parts or fragments thereof. For instance, an effector group can include an antibody light chain constant region (CL), an antibody CH1 heavy chain domain, an antibody CH2 heavy chain domain, an antibody CH3 heavy chain domain, or any combination thereof, in addition to the one or more constant region domains. An effector group may also comprise a hinge region of an antibody (such a region normally being found between the CH1 and CH2 domains of an IgG molecule).

In a further embodiment of this aspect of the invention, an effector group according to the present invention is an Fc region of an IgG molecule. Advantageously, a peptide ligand-effector group according to the present invention comprises or consists of a peptide ligand Fc fusion having a tβ half-life of a day or more, two days or more, 3 days or more, 4 days or more, 5 days or more, 6 days or more or 7 days or more. Most advantageously, the peptide ligand according to the present invention comprises or consists of a peptide ligand Fc fusion having a tβ half-life of a day or more.

Functional groups include, in general, binding groups, drugs, reactive groups for the attachment of other entities, functional groups which aid uptake of the macrocyclic peptides into cells, and the like.

The ability of peptides to penetrate into cells will allow peptides against intracellular targets to be effective. Targets that can be accessed by peptides with the ability to penetrate into cells include transcription factors, intracellular signalling molecules such as tyrosine kinases and molecules involved in the apoptotic pathway. Functional groups which enable the penetration of cells include peptides or chemical groups which have been added either to the peptide or the molecular scaffold. Peptides such as those derived from such as VP22, HIV-Tat, a homeobox protein of *Drosophila* (Antennapedia), e.g. as described in Chen and Harrison, Biochemical Society Transactions (2007) Volume 35, part 4, p821; Gupta et al. in Advanced Drug Discovery Reviews (2004) Volume 57 9637. Examples of short peptides which have been shown to be efficient at translocation through plasma membranes include the 16 amino acid penetratin peptide from *Drosophila* Antennapedia protein (Derossi et al (1994) J Biol. Chem. Volume 269 p10444), the 18 amino acid 'model amphipathic peptide' (Oehlke et al (1998) Biochim Biophys Acts Volume 1414 p127) and arginine rich regions of the HIV TAT protein. Non peptidic approaches include the use of small molecule mimics or SMOCs that can be easily attached to biomolecules (Okuyama et al (2007) Nature Methods Volume 4 p153). Other chemical strategies to add guanidinium groups to molecules also enhance cell penetration (Elson-Scwab et al (2007) J Biol Chem Volume 282 p13585). Small molecular weight molecules such as steroids may be added to the molecular scaffold to enhance uptake into cells.

One class of functional groups which may be attached to peptide ligands includes antibodies and binding fragments thereof, such as Fab, Fv or single domain fragments. In particular, antibodies which bind to proteins capable of increasing the half-life of the peptide ligand in vivo may be used.

RGD peptides, which bind to integrins which are present on many cells, may also be incorporated.

In one embodiment, a peptide ligand-effector group according to the invention has a tβ half-life selected from the group consisting of: 12 hours or more, 24 hours or more, 2 days or more, 3 days or more, 4 days or more, 5 days or more, 6 days or more, 7 days or more, 8 days or more, 9 days or more, 10 days or more, 11 days or more, 12 days or more, 13 days or more, 14 days or more, 15 days or more or 20 days or more. Advantageously a peptide ligand-effector group or composition according to the invention will have a tβ half life in the range 12 to 60 hours. In a further embodiment, it will have a tβ half-life of a day or more. In a further embodiment still, it will be in the range 12 to 26 hours.

In one particular embodiment of the invention, the functional group conjugated to the looped peptide is selected from a metal chelator, which is suitable for complexing metal radioisotopes of medicinal relevance. Such effectors, when complexed with said radioisotopes, can present useful agents for cancer therapy. Suitable examples include DOTA, NOTA, EDTA, DTPA, HEHA, SarAr and others (Targeted Radionuclide therapy, Tod Speer, Wolters/Kluver Lippincott Williams & Wilkins, 2011). Possible effector groups also include enzymes, for instance such as carboxypeptidase G2 for use in enzyme/prodrug therapy, where the peptide ligand replaces antibodies in ADEPT.

In one particular embodiment of this aspect of the invention, the functional group is selected from a drug, such as a cytotoxic agent for cancer therapy. Suitable examples include: alkylating agents such as cisplatin and carboplatin, as well as oxaliplatin, mechlorethamine, cyclophosphamide, chlorambucil, ifosfamide; Anti-metabolites including purine analogs azathioprine and mercaptopurine or pyrimidine analogs; plant alkaloids and terpenoids including vinca alkaloids such as Vincristine, Vinblastine, Vinorelbine and Vindesine; Podophyllotoxin and its derivatives etoposide and teniposide; Taxanes, including paclitaxel, originally known as Taxol; topoisomerase inhibitors including camptothecins: irinotecan and topotecan, and type II inhibitors including amsacrine, etoposide, etoposide phosphate, and teniposide. Further agents can include antitumour antibiotics which include the immunosuppressant dactinomycin (which is used in kidney transplantations), doxorubicin, epirubicin, bleomycin and others.

In one further particular embodiment of the invention according to this aspect, the cytotoxic agent is selected from DM1 or MMAE.

DM1 is a cytotoxic agent which is a thiol-containing derivative of maytansine and has the following structure:

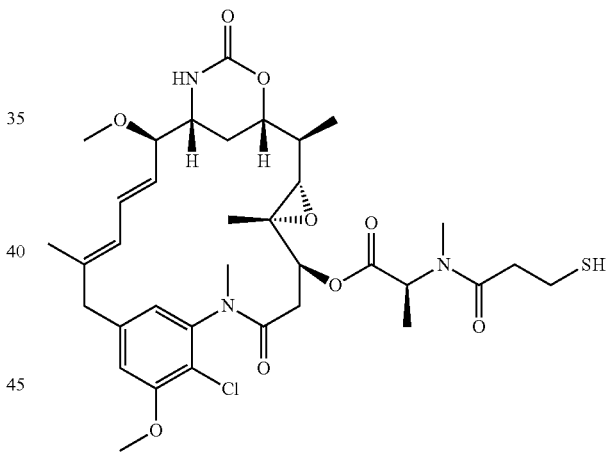

Monomethyl auristatin E (MMAE) is a synthetic antineoplastic agent and has the following structure:

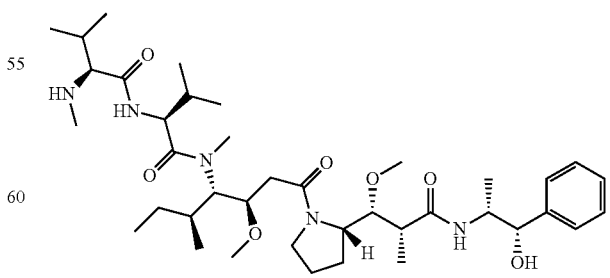

In one embodiment, the cytotoxic agent is linked to the bicyclic peptide by a cleavable bond, such as a disulphide bond. In a further embodiment, the groups adjacent to the disulphide bond are modified to control the hindrance of the disulphide bond, and by this the rate of cleavage and concomitant release of cytotoxic agent.

Published work established the potential for modifying the susceptibility of the disulphide bond to reduction by introducing steric hindrance on either side of the disulphide bond (Kellogg et al (2011) Bioconjugate Chemistry, 22, 717). A greater degree of steric hindrance reduces the rate of reduction by intracellular glutathione and also extracellular (systemic) reducing agents, consequentially reducing the ease by which toxin is released, both inside and outside the cell. Thus, selection of the optimum in disulphide stability in the circulation (which minimises undesirable side effects of the toxin) versus efficient release in the intracellular milieu (which maximises the therapeutic effect) can be achieved by careful selection of the degree of hindrance on either side of the disulphide bond.

The hindrance on either side of the disulphide bond is modulated through introducing one or more methyl groups on either the targeting entity (here, the bicyclic peptide) or toxin side of the molecular construct.

Thus, in one embodiment, the cytotoxic agent is selected from a compound of formula:

wherein n represents an integer selected from 1 to 10; and $R_1$ and $R_2$ independently represent hydrogen or methyl groups.

In one embodiment of the compound of the above formula, n represents 1 and $R_1$ and $R_2$ both represent hydrogen (i.e. the maytansine derivative DM1).

In an alternative embodiment of the compound of the above formula, n represents 2, $R_1$ represents hydrogen and $R_2$ represents a methyl group (i.e. the maytansine derivative DM3).

In one embodiment of the compound, n represents 2 and $R_1$ and $R_2$ both represent methyl groups (i.e. the maytansine derivative DM4).

It will be appreciated that the cytotoxic agent can form a disulphide bond, and in a conjugate structure with a bicyclic peptide, the disulphide connectivity between the thiol-toxin and thiol-bicyclic peptide is introduced through several possible synthetic schemes.

In one embodiment, the bicyclic peptide component of the conjugate has the following structure:

wherein m represents an integer selected from 0 to 10,

Bicycle represents any suitable looped peptide structure as described herein; and $R_3$ and $R_4$ independently represent hydrogen or methyl.

Compounds of the above formula where $R_3$ and $R_4$ are both hydrogen are considered unhindered and compounds of the above formula where one or all of $R_3$ and $R_4$ represent methyl are considered hindered.

It will be appreciated that the bicyclic peptide of the above formula can form a disulphide bond, and in a conjugate structure with a cytotoxic agent described above, the disulphide connectivity between the thiol-toxin and thiol-bicyclic peptide is introduced through several possible synthetic schemes.

In one embodiment, the cytotoxic agent is linked to the bicyclic peptide by the following linker:

wherein $R_1$, $R_2$, $R_3$ and $R_4$ represent hydrogen or C1-C6 alkyl groups;

Toxin refers to any suitable cytotoxic agent defined herein;

Bicycle represents any suitable looped peptide structure as described herein;

n represents an integer selected from 1 to 10; and m represents an integer selected from 0 to 10.

When $R_1$, $R_2$, $R_3$ and $R_4$ are each hydrogen, the disulphide bond is least hindered and most susceptible to reduction. When $R_1$, $R_2$, $R_3$ and $R_4$ are each alkyl, the disulphide bond is most hindered and least susceptible to reduction. Partial substitutions of hydrogen and alkyl yield a gradual increase in resistance to reduction, and concomitant cleavage and release of toxin. Preferred embodiments include: $R_1$, $R_2$, $R_3$ and $R_4$ all H; $R_1$, $R_2$, $R_3$ all H and $R_4$=methyl; $R_1$, $R_2$=methyl and $R_3$, $R_4$=H; $R_1$, $R_3$=methyl and $R_2$, $R_4$=H; and $R_1$, $R_2$=H, $R_3$, $R_4$=C1-C6 alkyl.

In one embodiment, the toxin of compound is a maytansine and the conjugate comprises a compound of the following formula:

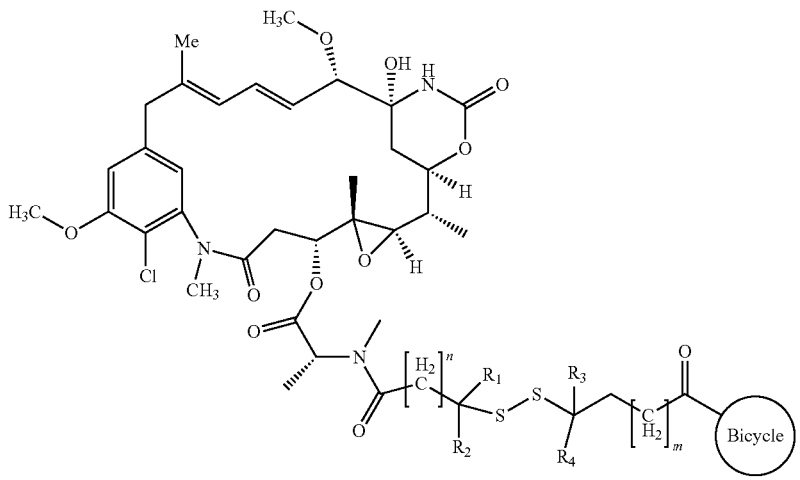

wherein $R_1$, $R_2$, $R_3$ and $R_4$ are as defined above;
Bicycle represents any suitable looped peptide structure as defined herein;
n represents an integer selected from 1 to 10; and
m represents an integer selected from 0 to 10.

Further details and methods of preparing the above-described conjugates of bicycle peptide ligands with toxins are described in detail in our published patent application WO2016/067035 and pending application GB1607827.1 filed on 4 May 2016. The entire disclosure of these applications is expressly incorporated herein by reference.

The linker between the toxin and the bicycle peptide may comprise a triazole group formed by click-reaction between an azide-functionalized toxin and an alkyne-functionalized bicycle peptide structure (or vice-versa). In other embodiments, the bicycle peptide may contain an amide linkage formed by reaction between a carboxylate-functionalized toxin and the N-terminal amino group of the bicycle peptide.

The linker between the toxin and the bicycle peptide may comprise a cathepsin-cleavable group to provide selective release of the toxin within the target cells. A suitable cathepsin-cleavable group is valine-citrulline.

The linker between the toxin and the bicycle peptide may comprise one or more spacer groups to provide the desired functionality, e.g. binding affinity or cathepsin cleavability, to the conjugate. A suitable spacer group is para-amino benzyl carbamate (PABC) which may be located intermediate the valine-citrulline group and the toxin moiety.

Thus, in embodiments, the bicycle peptide-drug conjugate may have the following structure made up of Toxin-PABC-cit-val-triazole-Bicycle:

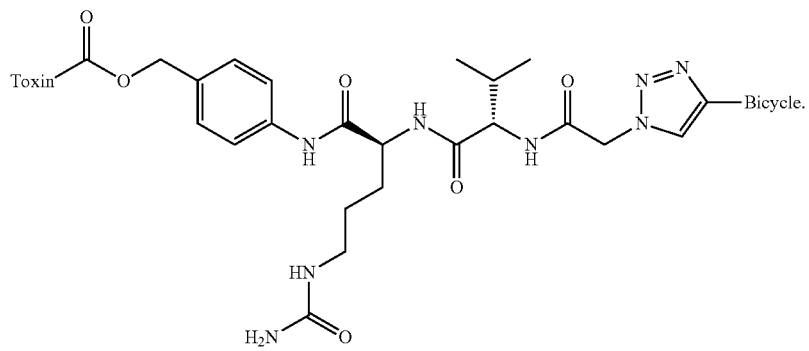

In further embodiments, the bicycle peptide-drug conjugate may have the following structure made up of Toxin-PABC-cit-val-dicarboxylate-Bicycle:

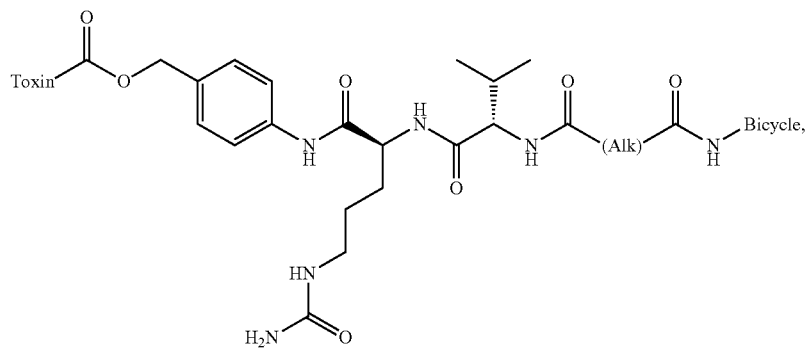

Wherein (alk) is an alkylene group of formula $C_nH_{2n}$ wherein n is from 1 to 10 and may be linear or branched, suitably (alk) is n-propylene or n-butylene.

Peptide derivatives according to the present invention may be employed in in vivo therapeutic and prophylactic applications, in vitro and in vivo diagnostic applications, in vitro assay and reagent applications, and the like.

In general, the use of a peptide derivative can replace that of an antibody. Derivatives selected according to the invention are of use diagnostically in Western analysis and in situ protein detection by standard immunohistochemical procedures; for use in these applications, the derivatives of a selected repertoire may be labelled in accordance with techniques known in the art. In addition, such peptide derivatives may be used preparatively in affinity chromatography procedures, when complexed to a chromatographic support, such as a resin. All such techniques are well known to one of skill in the art. Peptide derivatives according to the present invention possess binding capabilities similar to those of antibodies, and may replace antibodies in such assays.

Diagnostic uses include any uses which to which antibodies are normally put, including test-strip assays, laboratory assays and immunodiagnostic assays.

Therapeutic and prophylactic uses of peptide derivatives prepared according to the invention involve the administration of derivatives selected according to the invention to a recipient mammal, such as a human. Substantially pure peptide derivatives of at least 90 to 95% homogeneity are preferred for administration to a mammal, and 98 to 99% or more homogeneity is most preferred for pharmaceutical uses, especially when the mammal is a human. Once purified, partially or to homogeneity as desired, the selected peptides may be used diagnostically or therapeutically (including extracorporeally) or in developing and performing assay procedures, immunofluorescent stainings and the like (Lefkovite and Pernis, (1979 and 1981) Immunological Methods, Volumes I and II, Academic Press, NY).

The peptide derivatives of the present invention will typically find use in preventing, suppressing or treating inflammatory states, allergic hypersensitivity, cancer, bacterial or viral infection, and autoimmune disorders (which include, but are not limited to, Type I diabetes, multiple sclerosis, rheumatoid arthritis, systemic lupus erythematosus, Crohn's disease and myasthenia gravis).

In the instant application, the term "prevention" involves administration of the protective composition prior to the induction of the disease. "Suppression" refers to administration of the composition after an inductive event, but prior to the clinical appearance of the disease. "Treatment" involves administration of the protective composition after disease symptoms become manifest.

Animal model systems which can be used to screen the effectiveness of the peptide derivatives in protecting against or treating the disease are available.

Methods for the testing of systemic lupus erythematosus (SLE) in susceptible mice are known in the art (Knight et al. (1978) J Exp. Med., 147: 1653; Reinersten et al. (1978) New Eng. J. Med., 299: 515). Myasthenia Gravis (MG) is tested in SJL/J female mice by inducing the disease with soluble AchR protein from another species (Lindstrom et al. (1988) Adv. Immunol., 42: 233). Arthritis is induced in a susceptible strain of mice by injection of Type II collagen (Stuart et al. (1984) Ann. Rev. Immunol., 42: 233). A model by which adjuvant arthritis is induced in susceptible rats by injection of mycobacterial heat shock protein has been described (Van Eden et al. (1988) Nature, 331: 171). Thyroiditis is induced in mice by administration of thyroglobulin as described (Maron et al. (1980) J. Exp. Med., 152: 1115). Insulin dependent diabetes mellitus (IDDM) occurs naturally or can be induced in certain strains of mice such as those described by Kanasawa et al. (1984) Diabetologia, 27: 113. EAE in mouse and rat serves as a model for MS in human. In this model, the demyelinating disease is induced by administration of myelin basic protein (see Paterson (1986) Textbook of Immunopathology, Mischer et al., eds, Grune and Stratton, New York, pp. 179-213; McFarlin et al. (1973) Science, 179: 478: and Satoh et al. (1987) J. Immunol., 138: 179).

Generally, the present peptide derivatives will be utilised in purified form together with pharmacologically appropriate carriers. Typically, these carriers include aqueous or alcoholic/aqueous solutions, emulsions or suspensions, any including saline and/or buffered media. Parenteral vehicles include sodium chloride solution, Ringer's dextrose, dextrose and sodium chloride and lactated Ringer's. Suitable physiologically-acceptable adjuvants, if necessary to keep a peptide complex in suspension, may be chosen from thickeners such as carboxymethylcellulose, polyvinylpyrrolidone, gelatin and alginates.

Intravenous vehicles include fluid and nutrient replenishers and electrolyte replenishers, such as those based on Ringer's dextrose. Preservatives and other additives, such as antimicrobials, antioxidants, chelating agents and inert gases, may also be present (Mack (1982) Remington's Pharmaceutical Sciences, 16th Edition).

The peptide derivatives of the present invention may be used as separately administered compositions or in conjunction with other agents. These can include antibodies, antibody fragments and various immunotherapeutic drugs, such as cyclosporine, methotrexate, adriamycin or cisplatinum, and immunotoxins. Pharmaceutical compositions can include "cocktails" of various cytotoxic or other agents in conjunction with the selected antibodies, receptors or binding proteins thereof of the present invention, or even combinations of selected peptides according to the present invention having different specificities, such as peptides selected using different target derivatives, whether or not they are pooled prior to administration.

The route of administration of pharmaceutical compositions according to the invention may be any of those commonly known to those of ordinary skill in the art. For therapy, including without limitation immunotherapy, the selected antibodies, receptors or binding proteins thereof of the invention can be administered to any patient in accordance with standard techniques. The administration can be by any appropriate mode, including parenterally, intravenously, intramuscularly, intraperitoneally, transdermally, via the pulmonary route, or also, appropriately, by direct infusion with a catheter. The dosage and frequency of administration will depend on the age, sex and condition of the patient, concurrent administration of other drugs, counterindications and other parameters to be taken into account by the clinician.

The peptide derivatives of this invention can be lyophilised for storage and reconstituted in a suitable carrier prior to use. This technique has been shown to be effective and art-known lyophilisation and reconstitution techniques can be employed. It will be appreciated by those skilled in the art that lyophilisation and reconstitution can lead to varying degrees of activity loss and that use levels may have to be adjusted upward to compensate.

The compositions containing the present peptide derivatives or a cocktail thereof can be administered for prophylactic and/or therapeutic treatments. In certain therapeutic applications, an adequate amount to accomplish at least partial inhibition, suppression, modulation, killing, or some other measurable parameter, of a population of selected cells is defined as a "therapeutically-effective dose". Amounts needed to achieve this dosage will depend upon the severity of the disease and the general state of the patient's own immune system, but generally range from 0.005 to 5.0 mg of selected peptide derivative per kilogram of body weight, with doses of 0.05 to 2.0 mg/kg/dose being more commonly used. For prophylactic applications, compositions containing the present peptide derivatives or cocktails thereof may also be administered in similar or slightly lower dosages.

A composition containing a peptide derivative according to the present invention may be utilised in prophylactic and therapeutic settings to aid in the alteration, inactivation, killing or removal of a select target cell population in a mammal. In addition, the selected repertoires of peptides described herein may be used extracorporeally or in vitro selectively to kill, deplete or otherwise effectively remove a target cell population from a heterogeneous collection of cells. Blood from a mammal may be combined extracorporeally with the selected peptide derivatives whereby the undesired cells are killed or otherwise removed from the blood for return to the mammal in accordance with standard techniques.

The invention is further described with reference to the following examples.

EXAMPLES

Materials and Methods
Protein Expression

The MT1-MMP hemopexin-like repeats (also known as the MT1-MMP hemopexin domain), residues Cys319-Gly511 from the human gene, were transiently expressed in HEK293 cells as secreted N-terminally His6-tagged soluble protein, using the pEXPR-IBA42 (IBA) expression vector. Following expression, the protein was purified by Nickel-NTA affinity chromatography followed by gel filtration, and purity was checked by SDS-PAGE. Batch to batch variability was also monitored by fluorescence thermal shift experiments in the presence/absence of a hemopexin domain binding bicycle.

Peptide Synthesis

Peptide synthesis was based on Fmoc chemistry, using a Symphony peptide synthesiser manufactured by Peptide Instruments and a Syro II synthesiser by MultiSynTech. Standard Fmoc-amino acids were employed (Sigma, Merck), with the following side chain protecting groups: Arg(Pbf); Asn(Trt); Asp(OtBu); Cys(Trt); Glu(OtBu); Gln(Trt); His(Trt); Lys(Boc); Ser(tBu); Thr(tBu); Trp(Boc); and Tyr(tBu) (Sigma). The coupling reagent was HCTU (Pepceuticals), diisopropylethylamine (DIPEA, Sigma) was employed as a base, and deprotection was achieved with 20% piperidine in DMF (AGTC). Syntheses were performed using 0.37 mmol/gr Fmoc-Rink amide AM resin (AGTC), Fmoc-amino acids were utilised at a four-fold excess, and base was at a four-fold excess with respect to the amino acids. Amino acids were dissolved at 0.2M in DMSO, HCTU at 0.4M in DMF, and DIPEA at 1.6M in N-methylpyrrolidone (Alfa Aesar). Conditions were such that coupling reactions contained between 20 to 50% DMSO in DMF, which reduced aggregation and deletions during the solid phase synthesis and enhanced yields. Coupling times were generally 30 minutes, and deprotection times 2×5 minutes. Fmoc-N-methylglycine (Fmoc-Sar-OH, Merck) was coupled for 1 hr, and deprotection and coupling times for the following residue were 20 min and 1 hr, respectively. After synthesis, the resin was washed with dichloromethane, and dried. Cleavage of side-chain protecting groups and from the support was effected using 10 mL of 95:2.5:2.5:2.5 v/v/v/w TFA/$H_2O$/iPr$_3$SiH/dithiothreitol for 3 hours. Following cleavage, the spent resin was removed by filtration, and the filtrate was added to 35 mL of diethylether that had been cooled at −80° C. Peptide pellet was centrifuged, the etheric supernatant discarded, and the peptide pellet washed with cold ether two more times. Peptides were then resolubilised in 5-10 mL acetonitrile-water and lyophilised. A small sample was removed for analysis of purity of the crude product by mass spectrometry (MALDI-TOF, Voyager DE from Applied Biosystems). Following lyophilisation, peptide powders were taken up in 10 mL 6 M guanidinium hydrochloride in $H_2O$, supplemented with 0.5 mL of 1 M dithiothreitol, and loaded onto a C8 Luna preparative HPLC column (Phenomenex). Solvents ($H_2O$, acetonitrile) were acidified with 0.1% heptafluorobutyric acid. The gradient ranged from 30-70% acetonitrile in 15 minutes, at a flowrate of 15-20 mL/min, using a Gilson preparative HPLC system. Fractions containing pure linear peptide material (as identified by MALDI) were used for preparation of the bicycle derivatives by coupling to a scaffold molecule as described further below.

All amino acids, unless noted otherwise, were used in the L-configurations. Non-natural amino acids were incorporated into peptide sequence using the general methods described above. The list of non-natural amino acid precursors employed herein are summarised in the table below:

| Supplier | Short name | Full chemical name |
| --- | --- | --- |
| AGTC | D-Asp | Fmoc-D-Asp(tBu)—OH |
| Iris Biotech | HPhe | Fmoc-L-Homophenylalanine |
| Alfa Aesar | 5FPhe | Fmoc-pentafluoro-L-phenylalanine |
| PolyPeptide Gropu | 4BrPhe | Fmoc-4-bromo-L-phenylalanine |
| Iris Biotech | bAla | Fmoc-beta-Ala-OH |
| Iris Biotech | 3Pal | Fmoc-L-3Pal-OH |
| Iris Biotech | 4Pal | Fmoc-L-4Pal-OH |
| Iris Biotech | D-Pro | Fmoc-D-Pro-OH |
| Merck Novabiochem | Aib | Fmoc-Aib-OH |
| Merck Novabiochem | D-Ala | Fmoc-D-Ala-OH |
| Merck Novabiochem | D-Arg | Fmoc-D-Arg(Pbf)-OH |
| Merck Novabiochem | D-Gln | Fmoc-D-Gln(Trt)-OH |
| Merck Novabiochem | D-His | Fmoc-D-His(Trt)-OH |
| Merck Novabiochem | Hyp | Fmoc-Hyp(tBu)—OH |
| Merck Novabiochem | D-Leu | Fmoc-D-Leu-OH |
| Merck Novabiochem | HArg | Fmoc-L-HArg(Boc)2-OH |
| Peptech Corporation | 4,4-BPAl | Fmoc-L-4,4'-Biphenylalanine |
| Peptech Corporation | 3,3-DPA | Fmoc-L-3,3-Diphenylalanine |
| Peptech Corporation | Dpg | Fmoc-Dipropylglycine |
| Peptech Corporation | 1Nal | Fmoc-L-1-Naphthylalanine |
| Peptech Corporation | 2NAl | Fmoc-L-2-Naphthylalanine |
| Peptech Corporation | Pip | Fmoc-L-Pipecolic acid |
| Polypeptide Group | Aze | Fmoc-L-azetidine-2-carboxylic acid |
| Polypeptide Group | Cha | Fmoc-beta-cyclohexyl-L-alanine |
| Polypeptide Group | 4FluoPro | (2S,4R)-Fmoc-4-fluoro-pyrrolidine-2-carboxylic acid |
| AGTC | D-Asp | Fmoc-D-Asp(tBu)—OH |
| Merck | tBuGly | Fmoc-α-tert-butylglycine |
| Iris Biotech | Chg | Fmoc-L-cyclohexylglycine |
| Fluorochem | Phg | Fmoc-Phenylglycine-OH |
| Iris Biotech | 3Pal | Fmoc-L-3Pal-OH |
| Iris Biotech | 4Pal | Fmoc-L-4Pal-OH |
| Merck Novabiochem | D-Leu | Fmoc-D-Leu-OH |
| Merck Novabiochem | HArg | Fmoc-L-HArg(Boc)2-OH |
| Polypeptide Group | 3,4 DCPhe | Fmoc-3,4-dichloro-L-phenylalanine |
| Polypeptide Group | Cha | Fmoc-beta-cyclohexyl-L-alanine |

In addition, the following non-natural amino acid precursors were used for the preparation of the DAP and N-Alk-Dap modified peptides:

| Compound | CAS | Mw | Supplier | Order No |
| --- | --- | --- | --- | --- |
| Fmoc-L-Dap(Boc,Me)—OH | 446847-80-9 | 440.49 | Iris Biotech GMBH | FAA4195 |
| Fmoc-Dap(Boc)-OH | 162558-25-0 | 426.46 | Sigma Aldrich | 47551 |

Binding Affinity to MT1-MMP

Binding affinity was measured using competition assays using Fluorescence Polarisation (anisotropy).

Fluorescent tracers referred to herein are bicyclic peptides that have been fluoresceinated using 5,6-carboxyfluorescein. Fluoresceination may be performed on the N-terminal amino group of the peptide, which is separated from the bicycle core sequence by a sarcosine spacer (usually Sar5). This can be done during Fmoc solid phase synthesis or post-synthetically (after cyclisation with TBMB and purification) if the N-terminal amino group is unique to the peptide. Fluoresceination can also be performed on the C-terminus, usually on a Lysine introduced as the first C-terminal residue, which is then separated from the bicycle core sequence by a sarcosine spacer (usually Sar6). Thus, N-terminal tracers can have a molecular format described as Fluo-Gly-Sar5-A(BicycleCoreSequence), and (BicycleCoreSequence)-A-Sar6-K(Fluo) for a C-terminally fluoresceinated construct. Fluorescent tracers used in the Examples are A-(17-69)-A-Sar6-K(Fluo), A-(17-69-07)-A-Sar6-K(Fluo), and A-(17-69-12)-A-Sar6-K(Fluo). Due to the acidic nature of the 17-69 fluorescent peptides, they were typically prepared as concentrated DMSO stocks, from which dilution were prepared in 100 mM Tris pH 8 buffer.

Due to their high affinities to the MT1-MMP Hemopexin domain (PEX), the fluoresceinated derivatives herein can be used for competition experiments (using FP for detection). Here, a pre-formed complex of PEX with the fluorescent PEX-binding tracer is titrated with free, non-fluoresceinated bicyclic peptide. Since all 17-69-based peptides are expected to bind at the same site, the titrant will displace the fluorescent tracer from PEX. Dissociation of the complex can be measured quantitatively, and the Kd of the competitor (titrant) to the target protein determined. The advantage of the competition method is that the affinities of non-fluoresceinated bicyclic peptides can be determined accurately and rapidly.

Concentrations of tracer are usually at the Kd or below (here, 1 nM), and the binding protein (here, hemopexin of MT1-MMP) is at a 15-fold excess such that >90% of the tracer is bound. Subsequently, the non-fluorescent competitor bicyclic peptide (usually just the bicycle core sequence) is titrated, such that it displaces the fluorescent tracer from the target protein. The displacement of the tracer is measured and associated with a drop in fluorescence polarisation. The drop in fluorescence polarisation is proportional to the fraction of target protein bound with the non-fluorescent titrant, and thus is a measure of the affinity of titrant to target protein.

The raw data is fit to the analytical solution of the cubic equation that describes the equilibria between fluorescent tracer, titrant, and binding protein. The fit requires the value of the affinity of fluorescent tracer to the target protein, which can be determined separately by direct binding FP experiments (see previous section). The curve fitting was performed using Sigmaplot 12.0 and used an adapted version of the equation described by Zhi-Xin Wang (FEBS Letters 360 (1995) 111-114).

Reference Example 1

Figure 2:
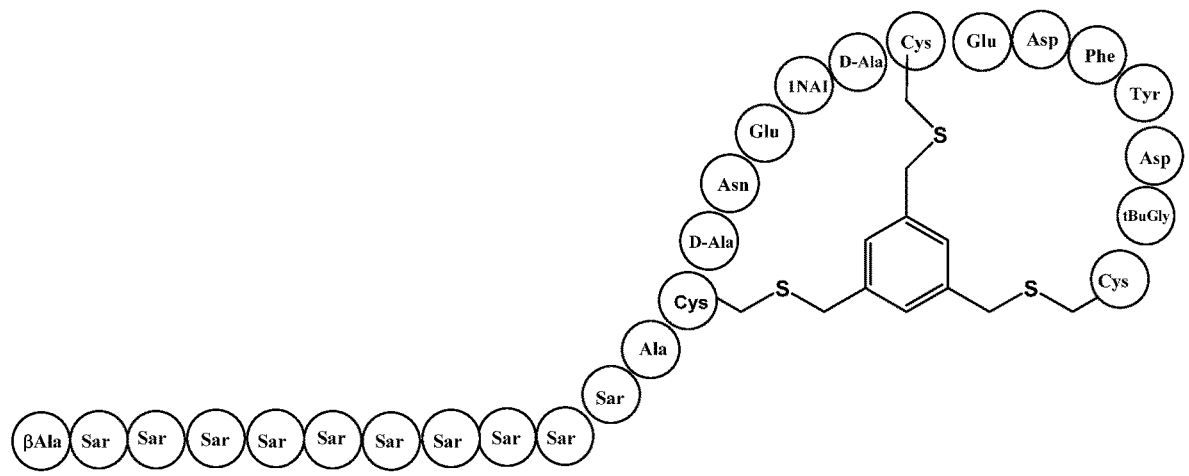
FIG. 2 shows a thioether-linked bicyclic peptide ligand according to the prior art; designated as 17-69-07-N241

The Bicyclic Peptide chosen for comparison of thioether to alkylamino scaffold linkage was designated 17-69-07-N241. It is a bicycle conjugate of a thioether-forming peptide with a trimethylene benzene scaffold. The structure of this bicycle derivative is shown schematically in FIG. 2. The linear peptide before conjugation has sequence:

```
                                         (SEQ ID NO: 16)
H-(β-Ala)-Sar10-Ala-Cys-(D-Ala)-Asn-Glu- (1Nal)-(D-Ala)-Cys-Glu-Asp-Phe-Tyr-Asp- (tBuGly)-Cys-NH₂.
```

Conjugation to 1,3,5-tris(bromomethyl)benzene (TBMB, Sigma) was carried out as follows. The linear peptide was diluted with $H_2O$ up to ~35 mL, ~500 μL of 100 mM TBMB in acetonitrile was added, and the reaction was initiated with 5 mL of 1 M $NH_4HCO_3$ in $H_2O$. The reaction was allowed to proceed for ~30-60 min at RT, and lyophilised once the reaction had completed (judged by MALDI). Following lyophilisation, the modified peptide was purified as above, while replacing the Luna C8 with a Gemini C18 column (Phenomenex), and changing the acid to 0.1% trifluoroacetic acid. Pure fractions containing the correct TMB-modified material were pooled, lyophilised and kept at −20° C. for storage.

The resulting Bicycle derivative designated 17-69-07-N241 showed high affinity to MT1-MMP. The measured affinity (Kd) to MT1-MMP of the derivative was 0.23 nM. The derivative is therefore regarded as a promising candidate for targeting tumor cells that express the cell surface metalloproteinase MT1-MMP.

Example 1

Figure 3:
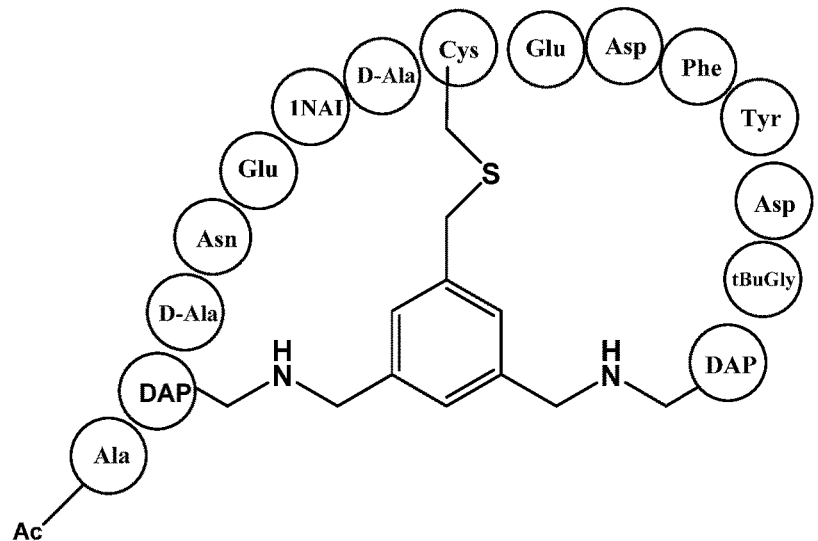
FIG. 3 shows a first secondary amino-linked bicyclic peptide ligand according to the present invention.

A bicycle peptide designated 17-69-07-N385 was made corresponding to the bicycle region of the peptide derivative of Reference Example 1, minus the b-Ala-Sar10 tail, and with replacement of the first and third cysteine residues by DAP residues forming alkylamino linkages to the TBMB scaffold. The structure of this derivative is shown schematically in FIG. 3.

The linear peptide used to form this bicycle was as follows:

(SEQ ID NO: 34)
Ac-A(Dap)(D-Ala)NE(1Nal)(D-Ala)CEDFYD(tBuGly)(Dap).

The linear peptide and the bicycle peptide had the following LCMS Characteristics:

|  | Retention Time | m/z present |
| --- | --- | --- |
| Linear peptide | 4.17 min | 886.1, 1771.7 |
| Cyclised peptide | 4.39 min | 942.7 |

Various reagents for the cyclisation step were tried as follows. Reagents were made up to the concentrations indicated in the table below in the chosen solvent. To a volume of peptide solution was added half that volume of TBMB solution, the mixture stirred well then half of the volume of base solution. The reaction was mixed and sampled periodically for LCMS analysis.

| Reagent | Initial Solution Concentration | Volume equivalents added to reaction | Final Reaction Concentration |
| --- | --- | --- | --- |
| Peptide | 1.0 mM | 1.0 | 0.5 mM |
| TBMB | 2.6 mM | 0.5 | 0.65 mM |
| Base | 200 mM | 0.5 | 50 mM |

Example: to 50 μL peptide solution was added 25 μL TBMB solution. The solution was mixed thoroughly then 25 μL base solution was added.

In cases where the solvent used is DMF, all reagents are made up in DMF. In cases where the solvent used is DMSO, all reagents are made up in DMSO. In cases where the solvent used is MeCN/H$_2$O, peptide solutions are made up in 50% MeCN/H$_2$O, TBMB solutions are made up in MeCN and base solutions are made up in H$_2$O, except when the base is DIPEA, in which case the base solution is made up in MeCN. All cyclisations were performed at room temperature. The results were as follows (range of spectrum set at 3.5-5.5 min. Spectrum at 220 nm integrated and sum of major peaks taken):

| Solvent | Base | Total integration | Product integration | % Product | Time |
| --- | --- | --- | --- | --- | --- |
| MeCN/H$_2$O | NEt$_3$ | 4641.0 | 2857.1 | 62% | 5 h |
|  | Na$_2$CO$_3$ | 5470.8 | 546.1 | 10% | 5 h |
|  | NaHCO$_3$ | 9956.5 | 3530.4 | 35% | 4 h |
|  | NH$_4$HCO$_3$ | 6948.9 | 0 | 0% | 5 h |
|  | Tetramethyl guanidine | 12130.5 | 211.9 | 2% | 5 h |
|  | DIPEA | 9081.1 | 5951.6 | 66% | 16 h |

It can be seen that the purity following cyclisation is highly dependent on the choice of base. Product purity ranges from 2 to 66%, with the latter involving a mixture of Acetonitrile/water in the presence of DIPEA. Unlike the cyclisation of Reference Example 1, the yield is relatively low when using the conventional NaHCO$_3$ as the base. Best yields are achieved using the trialkylamines, namely triethylamine and diisopropylethylamine (DIPEA).

Figure 7:
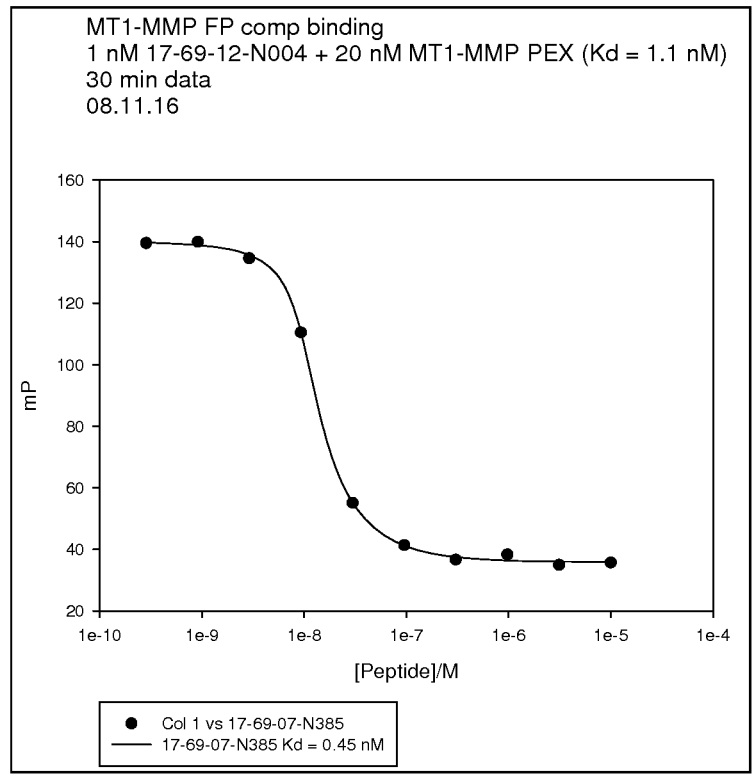
FIG. 7 shows competitive affinity binding assay data against MT1-MMP for the derivative of FIG. 3.

Comparative binding to MT1-MMP data are shown in FIG. 7. The measured Kd is 0.45 nM, which demonstrates that the change to alkylamino linkages in this example resulted in remarkably little change in binding affinity relative to the thioether linked derivative of Reference Example 1.

Example 2

Figure 4:
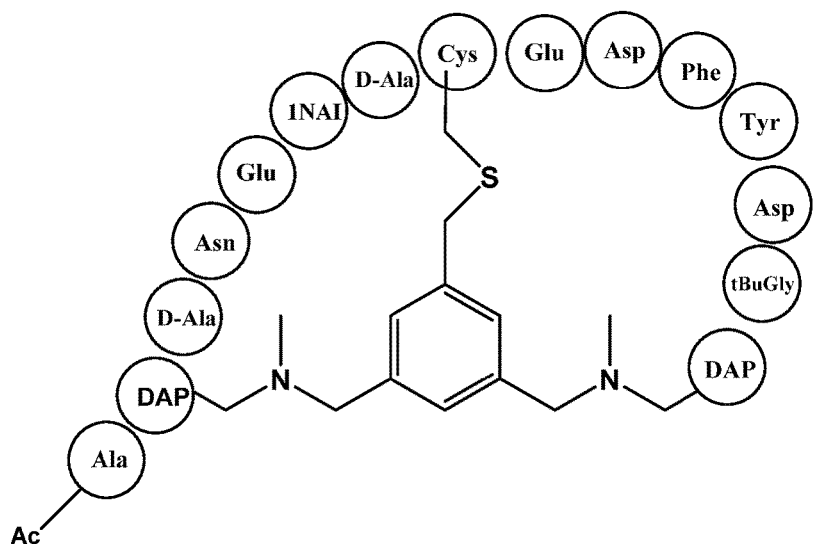
FIG. 4 shows a tertiary N-methyl amino-linked bicyclic peptide ligand according to the present invention.

A bicycle peptide designated 17-69-07-N426 was made corresponding to the bicycle peptide of Example 1 with replacement of the DAP residues by N-MeDAP residues. The structure of this derivative is shown schematically in FIG. 4. The linear peptide used to form this bicycle was as follows:

(SEQ ID NO: 28)
Ac-A(Dap(Me))(D-Ala)NE(1Nal)(D-Ala)CEDFYD(tBuGly)
(Dap(Me)).

The linear peptide and the bicycle peptide had the following LCMS Characteristics:

|  | Retention Time | m/z present |
| --- | --- | --- |
| Linear peptide | 4.19 min | 900.1, 1799.1 |
| Cyclised peptide | 4.38 min | 956.0, 1913.7 |

Various different reaction conditions, solvents, and bases were used for the cyclisation step as described in Example 1, with the following results (all cyclisations performed at room temperature):

| Solvent | Base | Total integration | Product integration | % Product | Time |
| --- | --- | --- | --- | --- | --- |
| MeCN/H$_2$O | Na$_2$CO$_3$ | 21659.8 | 12714.5 | 59% | 1 h |
| MeCN/H$_2$O | DIPEA | 10547.7 | 9841.3 | 93% | 16 h |

The purity following cyclisation is again dependent on the nature of the base. Purity with Na$_2$CO$_3$ as base is, as expected, low (see Example 1). Using the optimal condition of Acetonitrile/water in the presence of DIPEA, purity following cyclisation is very high (93%) demonstrating that N-methylation of Dap reduces the level of side reactions.

Figure 8:
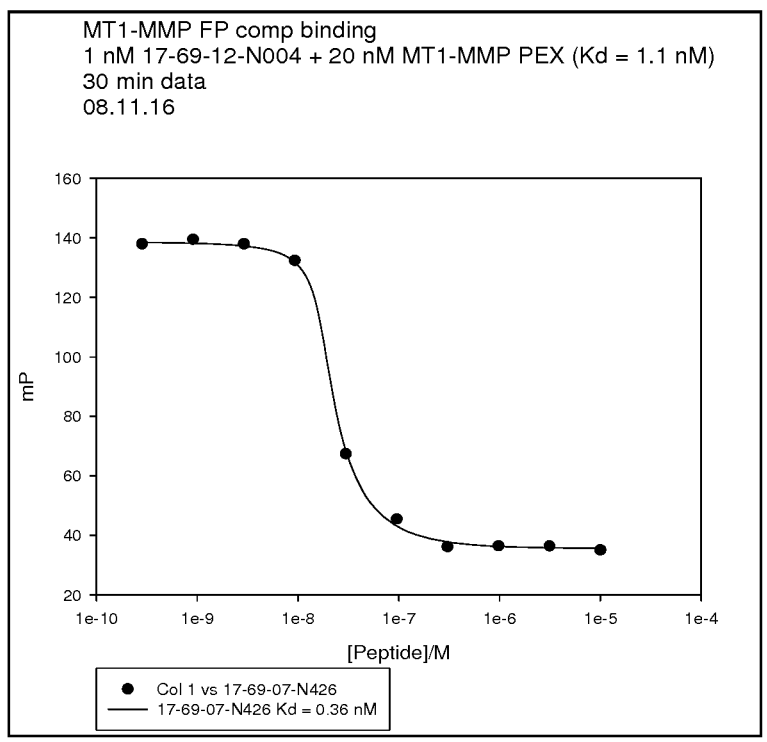
FIG. 8 shows competitive affinity binding assay data against MT1-MMP for the derivative of FIG. 4.

Comparative binding to MT1-MMP data are shown in FIG. 8. The measured Kd is 0.36 nM, which is almost unchanged from the thioether linked derivative of Reference Example 1. This potency is retained despite the two N-methylations on the linkage, and thus the derivative of the present example is of great interest.

Example 3

A bicycle peptide designated 17-69-07-N428 was made corresponding to the bicycle peptide of Example 1 with replacement of the Tyr9 by Phe9 (removal of Tyr hydroxyl). The linear peptide used to form this bicycle was as follows:

```
                                          (SEQ ID NO: 19)
Ac-A(Dap)(D-Ala)NE(1NaI)(D-Ala)CEDFF9D(tBuGly)
(Dap).
```

The linear peptide and the bicycle peptide had the following LCMS Characteristics:

|  | Retention Time | m/z present |
| --- | --- | --- |
| Linear peptide | 4.51 min | 876.5, 1755.4 |
| Cyclised peptide | 4.80 min | 935.3 |

Various different reaction conditions, solvents, and bases were used for the cyclisation step as described in Example 1, with the following results (LCMS range of spectrum set at 4-6 min. Spectrum at 220 nm integrated and sum of major peaks taken):

| Solvent | Base | Temp | Total integration | Product integration | % Product | Time |
| --- | --- | --- | --- | --- | --- | --- |
| MeCN/H$_2$O | DIPEA | rt | 5962.8 | 4209.3 | 71% | 6 h |
| MeCN/H$_2$O | DIPEA | 50° C. | 5936.4 | 2898.3 | 49% | 1 h |
| DMF | DIPEA | rt | 4804.6 | 84.7 | 2% | 1 h |
| DMF | DIPEA | 50° C. | 4384.8 | 309.7 | 7% | 1 h |
| MeCN/H$_2$O | TMG | rt | 5050.8 | 2023.8 | 40% | 1 h |
| MeCN/H$_2$O | K$_2$CO$_3$ | rt | 6366.7 | 4109.2 | 65% | 4 h |
| MeCN/H$_2$O | K$_2$CO$_3$ | 50° C. | 5314.5 | 2306.7 | 43% | 1 h |

It can be seen that product purity ranges from 2 to 71%, with the latter involving a mixture of Acetonitrile/water in the presence of DIPEA. The removal of the Tyr-OH (Tyr→Phe9) increases product yield significantly relative to the same reaction with the tyrosine-containing peptide under MeCN/H$_2$O/TMG/rt or MeCN/H$_2$O/K$_2$CO$_3$/rt conditions. Use of DMSO as solvent gave very messy chromatograms which could not be easily analysed.

Figure 9:
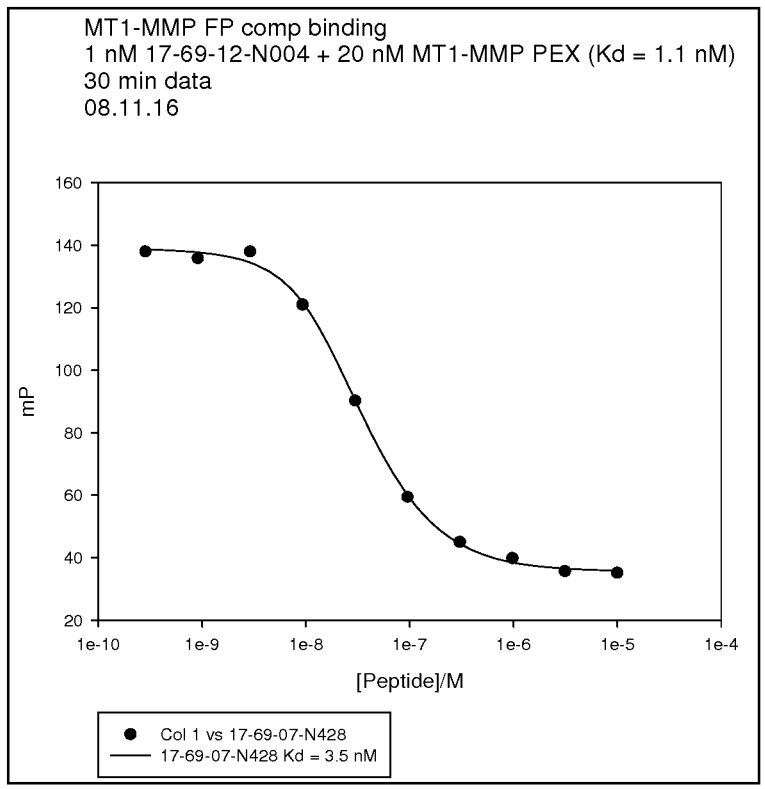
FIG. 9 shows competitive affinity binding assay data against MT1-MMP for a further derivative according to the invention.

Comparative binding data of this 17-69-07-N428 derivative to MT1-MMP are shown in FIG. 9. The measured Kd is 3.5 nM. The slight reduction in binding affinity relative to the thioether linked derivative of Reference Example 1 would appear to be mainly attributable to the replacement of the Tyr9 by Phe9.

Example 4

Figure 5:
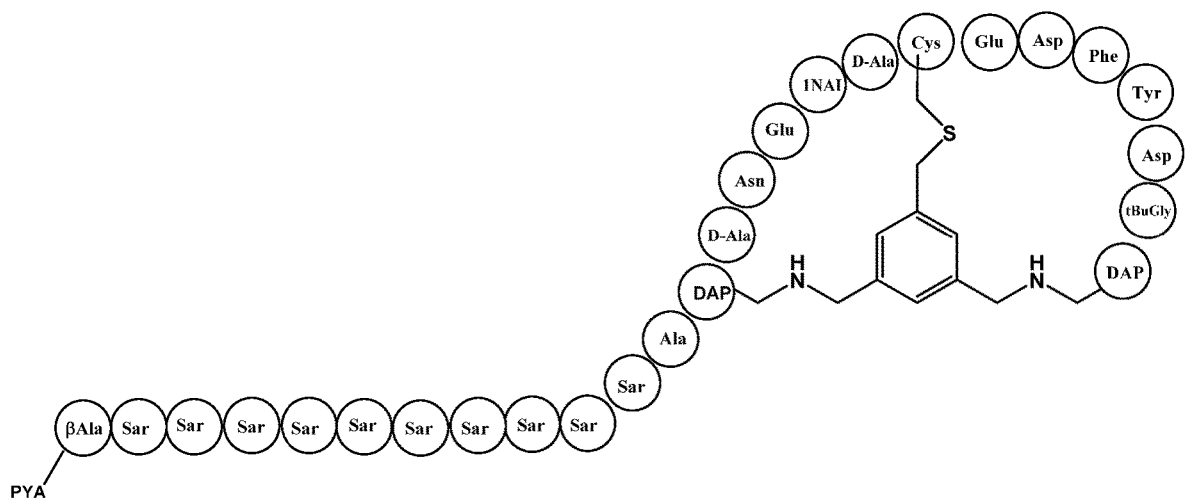
FIG. 5 shows a third secondary amino-linked bicyclic peptide ligand according to the present invention, which is the Dap analogue of 17-69-07-N241.

A bicycle peptide designated 17-69-07-N434 was made corresponding to the bicycle peptide of Example 1 with an N-terminal Sar10 spacer similar to that of Reference Example 1, and conjugating group PYA (pentynoic acid, for "click" derivatisation with toxin). The structure of this derivative is shown schematically in FIG. 5. The linear peptide used to form this bicycle was as follows:

```
                                          (SEQ ID NO: 35)
(PYA)-(B-Ala)-Sar10-A(Dap)(D-Ala)NE(1NaI)(D-Ala)
CEDFYD(tBuGly)(Dap).
```

The linear peptide and the bicycle peptide had the following LCMS Characteristics:

|  | Retention Time | m/z present |
| --- | --- | --- |
| Linear peptide | 4.18 | 863.7, 1294.8 |
| Cyclised peptide | 4.37 | 902.6, 1353.0 |

Cyclisation was performed as follows:
The

| Solvent | Base | Temp | Total integration | Product integration | % Product | Time |
| --- | --- | --- | --- | --- | --- | --- |
| MeCN/H$_2$O | DIPEA | rt | 4445.6 | 2666.5 | 60% | 4 h | resulting derivative 17-69-07-N434 is the Dap1/3 equivalent of N241 (Reference Example 1) with an N-terminal alkyn required for derivatisation with effectors, i.e. toxins. This peptide can be cyclised with TBMB at 60% purity. The measured k$_d$ with MT1-MMP was 1.52 nM, making this bicycle peptide highly suitable for targeting MT1-MMP.

Example 5

Replacement of the TBMB scaffold molecule used in Examples 1 to 3 by TBAB was performed as follows.

The linear peptides used to form 17-69-07-N385, 17-69-07-N426 and 17-69-07-N428 in Examples 1 to 3 were cyclised with TBAB at the same concentrations and equivalents as those used for TBMB.

Figure 6:
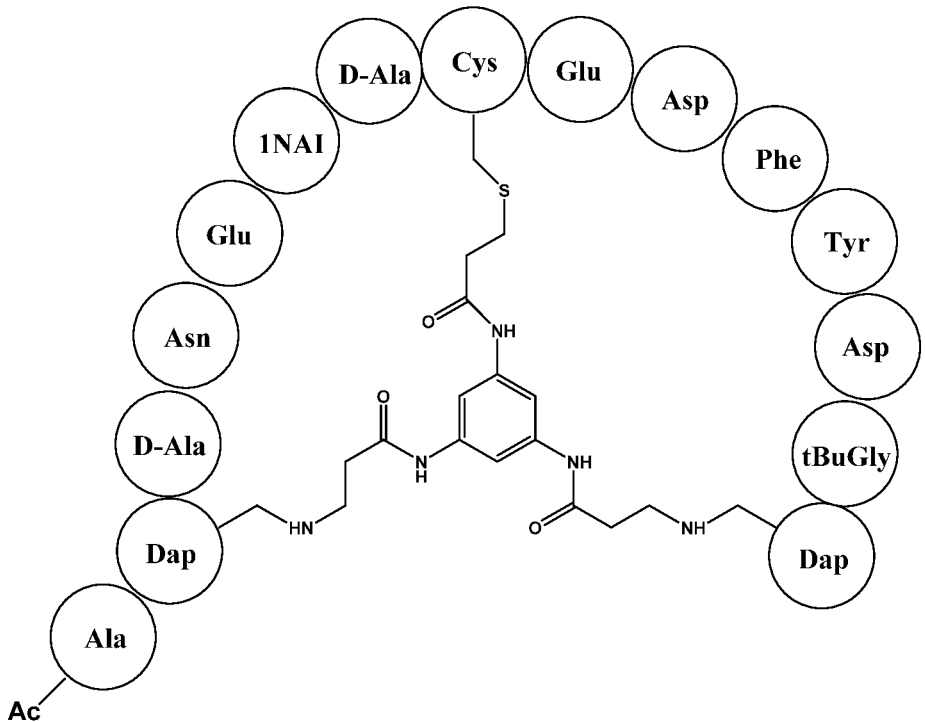
FIG. 6 shows a fourth secondary amino-linked bicyclic peptide ligand according to the present invention, cyclised with the TBAB scaffold.

The structure of the TBAB derivative with the N385 peptide is shown schematically in FIG. 6.

DIPEA was employed as base of choice with a solvent mixture of MeCN/H$_2$O at room temperature. The following results were achieved.

| Peptide | Product retention time | Total integration | Product integration | % Product | Time |
| --- | --- | --- | --- | --- | --- |
| 17-69-07-N385 | 4.28 min | 9399.8 | 8830.0 | 94% | 16 h |
| 17-69-07-N426 | 4.47 min | 11941.6 | 11485.1 | 96% | 16 h |
| 17-69-07-N428 | 4.70 min | 8321.8 | 7941.5 | 95% | 16 h |

These results show that TBAB (haloacetyl-) chemistry offers higher cyclisation rates and greater selectivity than TBMB, as can be seen from the % Product column.

Example 6

A bicycle peptide designated 17-69-07-N474 was made corresponding to the bicycle peptide of Example 1 with replacement of the Cys6 by Dap(Me). The linear peptide used to form this bicycle was as follows: Ac-A(Dap(Me)) (D-Ala)NE(1NaI)(D-Ala)(Dap(Me))EDFYD(tBuGly)(Dap (Me)) (SEQ ID NO. 33).

Figure 10:
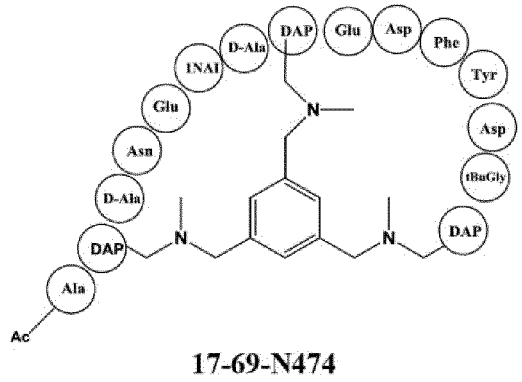
FIG. 10 shows schematic structures of certain bicycle peptide-TBMB derivatives according to the invention.
Figure 10:
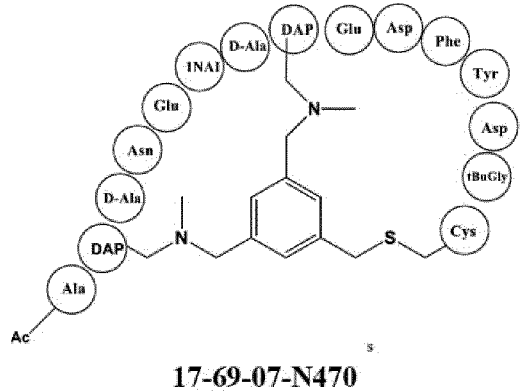
Figure 10:
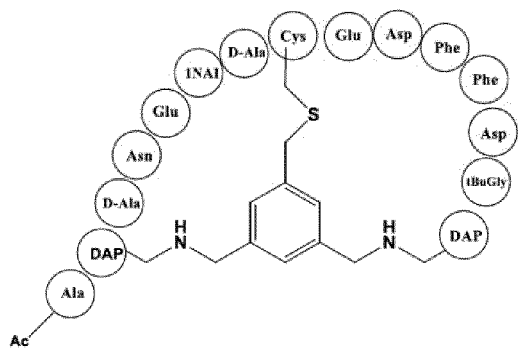
Figure 10:
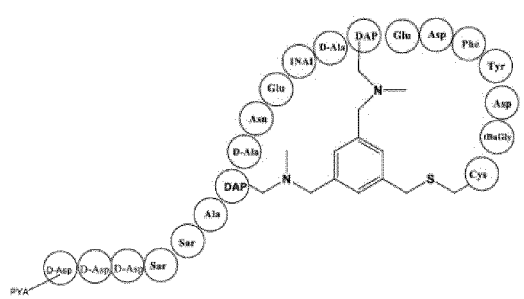
Figure 10:
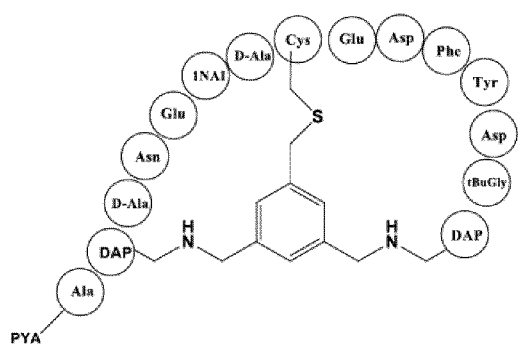
Figure 10:
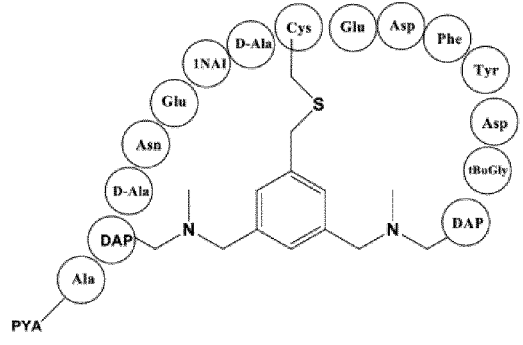
Figure 11:
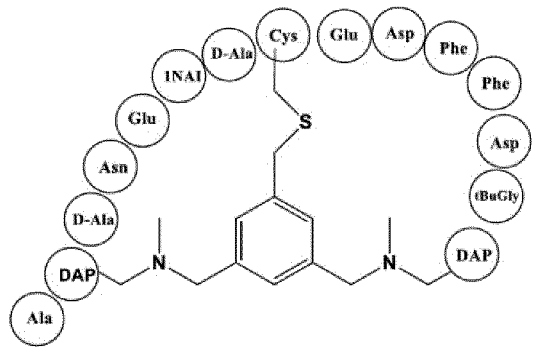
FIG. 11 shows the schematic structures of further bicycle peptide-TBMB derivatives in accordance with the present invention.
Figure 11:
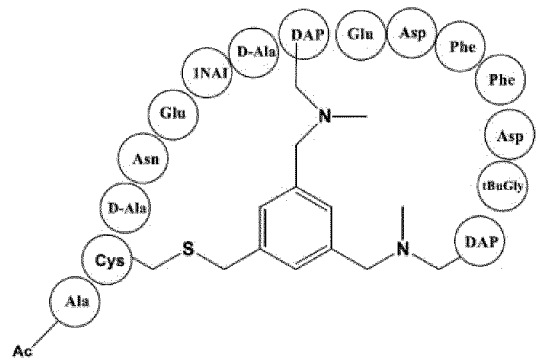
Figure 11:
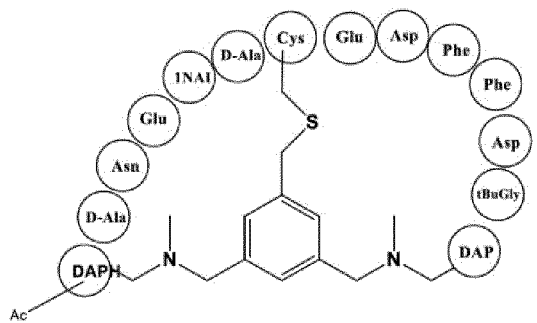
Figure 11:
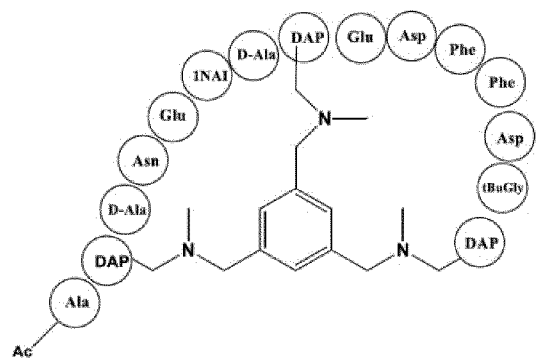
Figure 12:
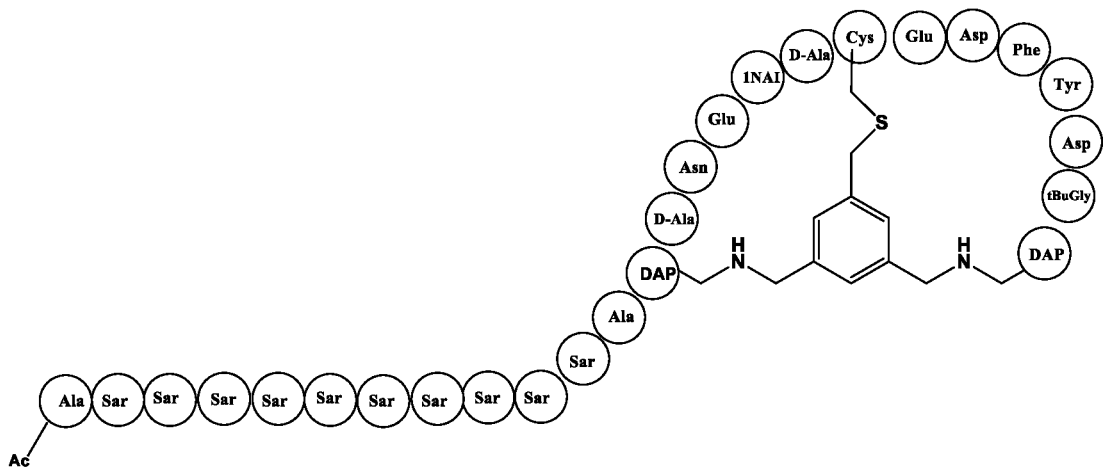
FIG. 12 shows the schematic structures of further bicycle peptide-TBMB derivatives in accordance with the present invention.
Figure 12:
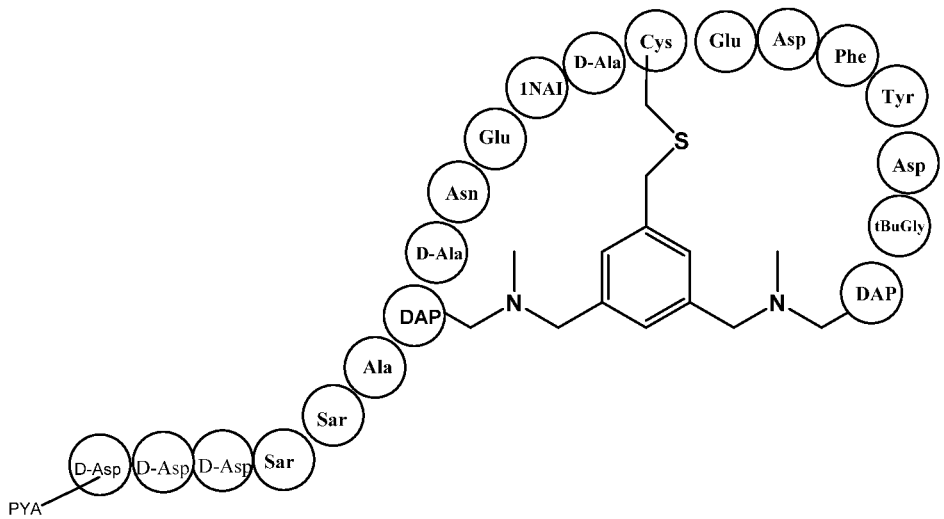
Figure 12:
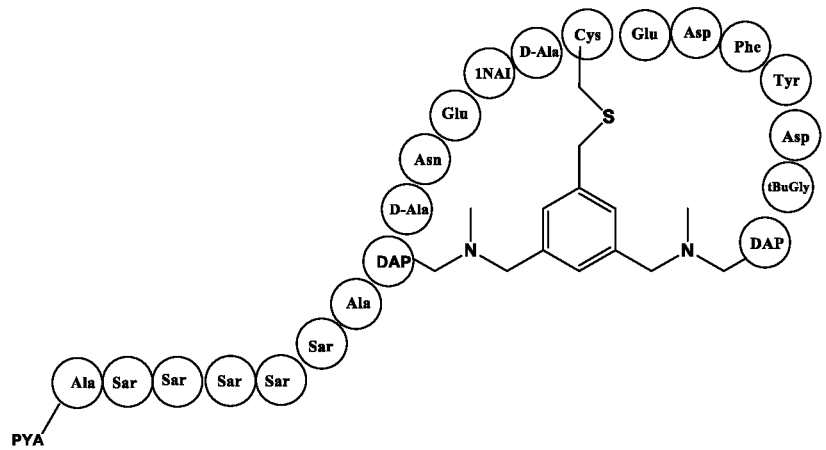
Figure 13:
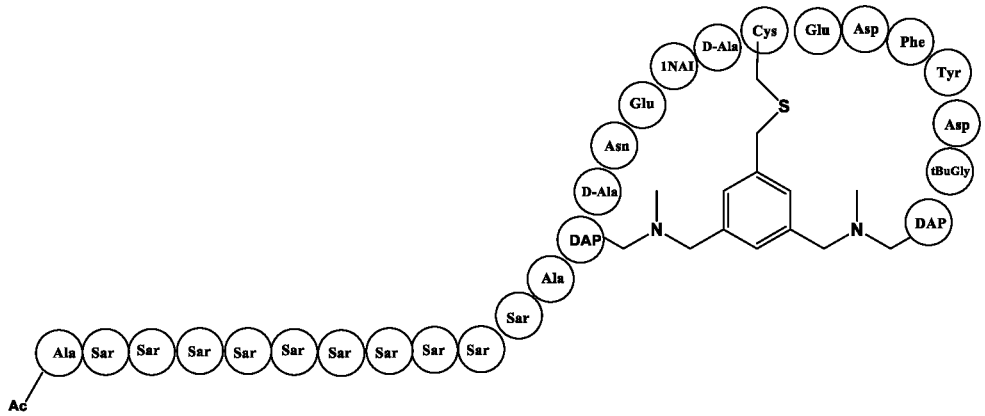
FIG. 13 shows the schematic structures of further bicycle peptide-TBMB derivatives in accordance with the present invention.
Figure 13:
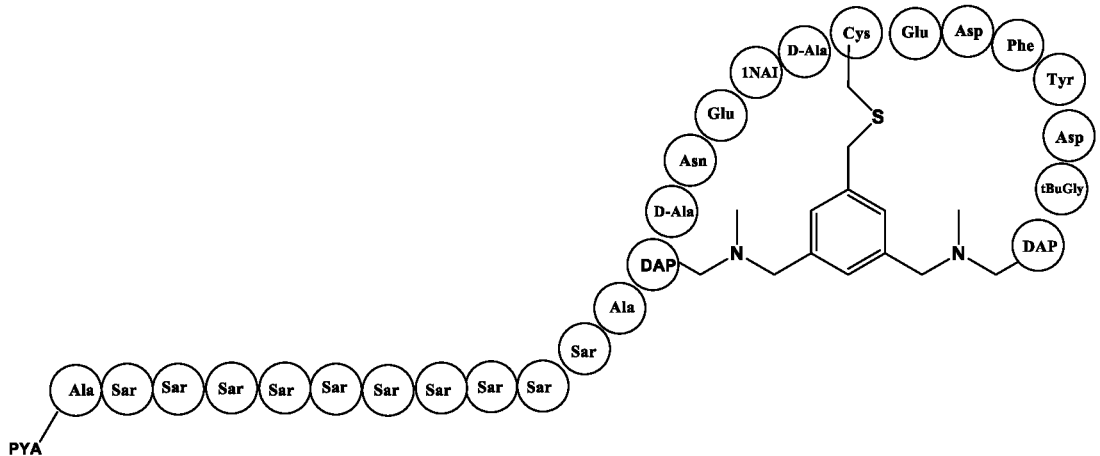
Figure 13:
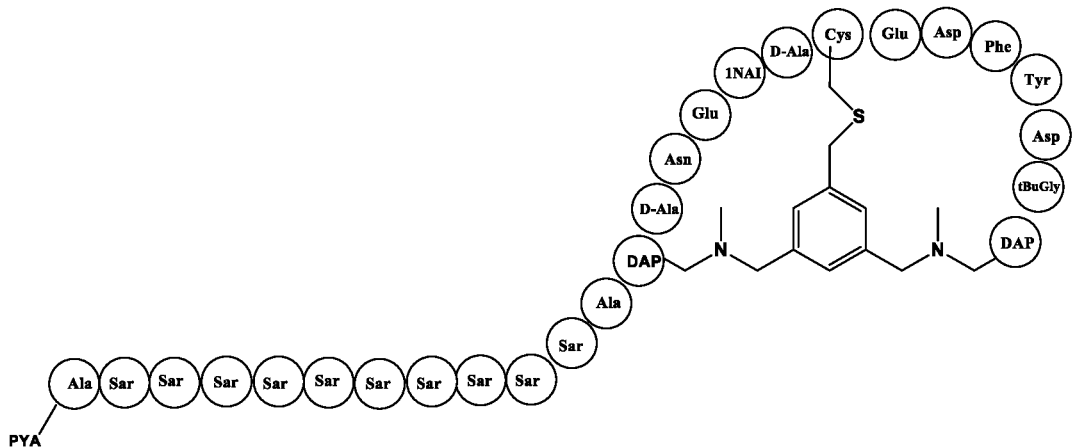

The structure of the TBMB derivative with the N385 peptide is shown schematically in FIG. 10.

The linear peptide and the bicycle peptide had the following LCMS Characteristics:

|  | Retention time | m/z present |
|---|---|---|
| Linear peptide | 3.61 min | 599.64, 898.96, 1795.90 |
| Cyclised peptide | 3.98 min | 637.68, 956.03, 1910.04 |

The cyclisation was performed according to the following procedure: 50 μL of a 1 mM solution of peptide in MeCN/H$_2$O (1:1) was mixed with 25 L 2.6 mM TBMB in MeCN, then 25 L 200 mM DIPEA in MeCN/H$_2$O (pH adjusted to 10 with acetic acid) was added and the solution mixed. (1.3 equivalents TBMB and 100 equivalents base with respect to peptide present in the reaction). LCMS samples were taken after 4 hours, and overnight with the reaction proceeding as shown in the table below.

| Total integration | Product integration | % Product | Time |
|---|---|---|---|
| 3120 | 1248 | 40 | 4 h |
| 3784 | 3632 | 96 | 18 h (overnight) |

Binding to MT1-MMP was assessed in the same manner as the other examples. The measured Kd is 8.0 nM, which is less than the thioether linked derivative of Reference Example 1. This compound still binds with high affinity despite the three N-methylDaps on the linkage, and thus the derivative of the present example is of great interest.

Example 7

The following further bicycle peptides according to the invention were prepared and tested for binding affinity with MT1-MMP using the methods described above. Schematic structures of these bicycle peptide compounds are shown in FIGS. 10-13.

| Compound ID | Sequence | Binding Affinity |
|---|---|---|
| 17-69-07-N428 | Ac-A(Dap)(D-Ala)NE(1Nal)(D-Ala)CEDFFD(tBuGly)(Dap) (SEQ ID NO: 19) | n/a |
| 17-69-07-N438 | PYA-A(Dap)(D-Ala)NE(1Nal)(D-Ala)CEDFYD(tBuGly)(Dap) (SEQ ID NO: 20) | Ki (h) = 3.1 nM |
| 17-69-07-N455 | Ac-(B-Ala)-Sar10-A(Dap)(D-Ala)NE(1Nal)(D-Ala)CEDFYD(tBuGly)(Dap) (SEQ ID NO: 21) | Ki (h) = 4 nM |
| 17-69-07-N470 | Ac-A(Dap(Me))(D-Ala)NE(1Nal)(D-Ala)(Dap(Me))EDFYD(tBuGly)C (SEQ ID NO: 22) | Ki (h) = 8.3 nM |
| 17-69-07-N473 | (PYA)-(D-Asp)3-Sar2-A(Dap(Me))(D-Ala)NE(1Nal)(D-Ala)(Dap(Me))EDFYD(tBuGly)C (SEQ ID NO: 23) | Ki (h) = 7.3 nM |
| 17-69-07-N443 | PYA-A(Dap(Me))(D-Ala)NE(1Nal)(D-Ala)CEDFYD(tBuGly)(Dap(Me)) (SEQ ID NO: 24) | Ki (h) = 3.2 nM |
| 17-69-07-N471 | (PYA)-(D-Asp)3-Sar2-A(Dap(Me))(D-Ala)NE(1Nal)(D-Ala)CEDFYD(tBuGly)(Dap(Me)) (SEQ ID NO: 25) | Ki (h) = 4.6 nM |
| 17-69-07-N472 | (PYA)-(B-Ala)-Sar5-A(Dap(Me))(D-Ala)NE(1Nal)(D-Ala)CEDFYD(tBuGly)(Dap(Me)) (SEQ ID NO: 26) | Ki (h) = 3.4 nM |
| 17-69-07-N454 | Ac-(B-Ala)-Sar10-A(Dap(Me))(D-Ala)NE(1Nal)(D-Ala)CEDFYD(tBuGly)(Dap(Me)) (SEQ ID NO: 27) | Ki (h) = 3.0 nM |
| 17-69-07-N452 | A(Dap(Me))(D-Ala)NE(1Nal)(D-Ala)CEDFYD(tBuGly)(Dap(Me)) (SEQ ID NO: 28) | Ki (h) = 4.0 nM |
| 17-69-07-N450 | (PYA)-(B-Ala)-Sar10-A(Dap(Me))(D-Ala)NE(1Nal)(D-Ala)CEDFYD(tBuGly)(Dap(Me)) (SEQ ID NO: 29) | Ki = 3.7 nM; Kd = 1.91 (SPR) |
| 17-69-07-N451 | (B-Ala)-Sar10-A(Dap(Me))(D-Ala)NE(1Nal)(D-Ala)CEDFYD(tBuGly)(Dap(Me)) (SEQ ID NO: 30) | Ki (h) = 3.7 nM |
| 17-69-07-N461 | Ac(Dap(Me))(D-Ala)NE(1Nal)(D-Ala)CEDFYD(tBuGly)(Dap(Me)) (SEQ ID NO: 31) | Ki (h) = 6.0 nM |
| 17-69-07-N479 | Ac-A(Dap(Me))(D-Ala)NE(1Nal)(D-Ala)CEDFYD(tBuGly)(Dap(Me)) (SEQ ID NO: 32) | Ki (h) = 15.6 nM |
| 17-69-07-N474 | Ac-A(Dap(Me))(D-Ala)NE(1Nal)(D-Ala)(Dap(Me))EDFYD(tBuGly)(Dap(Me)) (SEQ ID NO: 33) | Ki (h) = 7.5 nM |

It can be seen that high affinity to MT1-MMP is achieved with these alkylamino-linked bicycle compounds according to the invention. Further studies showed full cross-reactivity of bicycle peptides according to the invention with dog, mouse/rat and human MT1-MMP. Further studies showed high specificity of bicycle peptides according to the invention, with no significant cross-reactivity with MMP1 ectodomain, MMP2 ectodomain, MMP15 ectodomain (hemopexin domain) or MMP16 hemopexin domain. The pharmacokinetics of bicycle peptides according to the invention were also determined to be similar to the corresponding bicycle peptides having three thioether linkages to the scaffold, but with slightly longer half-life in serum measurements for the bicycle peptides of the invention.

Example 8

Figure 14:
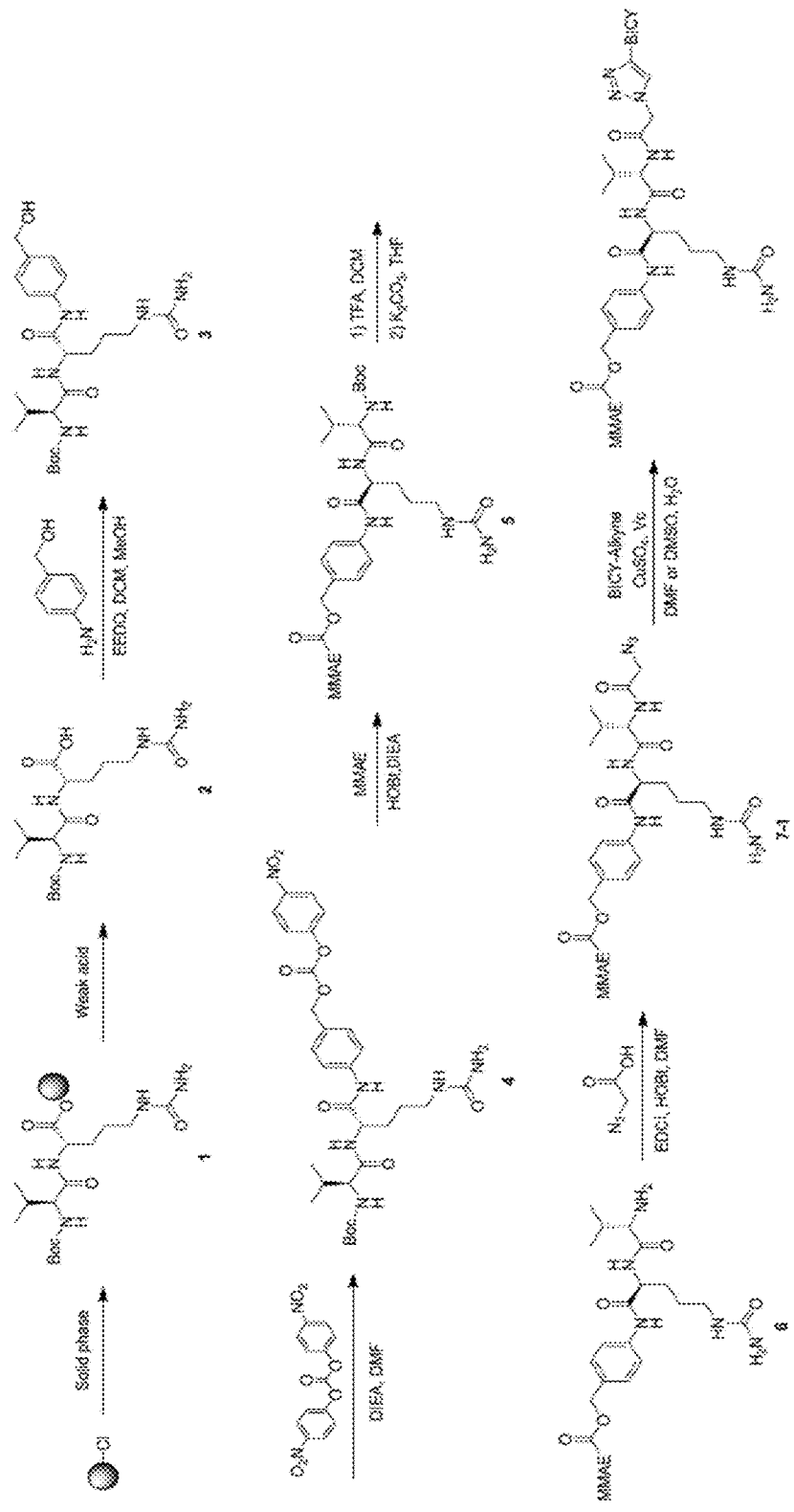
FIG. 14 shows a reaction scheme for preparation of a bicycle peptide-drug conjugate according to the invention by a click reaction to form a triazole linkage.

Bicycle peptide-drug conjugates (BCDs) in which bicycle peptides according to the invention are coupled to monomethyl auristatin E (MMAE) by a triazole cyclization reaction were prepared in accordance with the reaction scheme shown in FIG. 14. In addition to the triazole group, the linker groups in the conjugates include valine-citrulline (a cathepsin-cleavable group) and para-amino benzyl carbamate (PABC), a spacer group. The steps of the reaction scheme were performed as follows.

General Procedure for Preparation of Compound 3

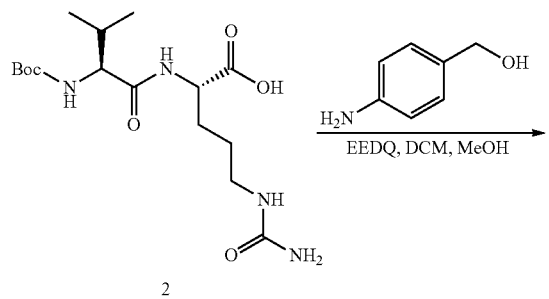

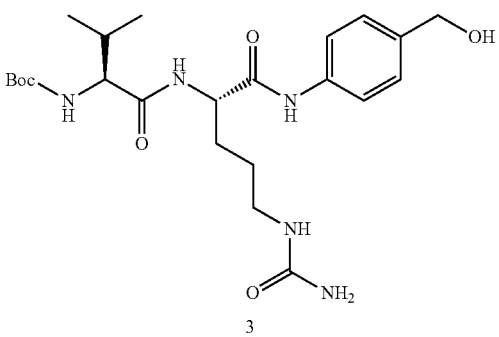

To a solution of compound 2 (30 g, 80 mmol) in DCM (300 mL) and MeOH (150 mL) was added 4-aminophenyl methanol (11 g, 88 mmol) and EEDQ (40 g, 160 mmol) in the dark. The mixture was stirred at 30° C. for 16 hr. TLC (DCM:MeOH=10/1, $R_f$=0.43) indicated compound 2 was consumed completely and many new spots formed. The reaction was clean according to TLC. The resulting reaction mixture was concentrated to give a residue, which was purified by flash silica gel chromatography (ISCO®; 330 g×3 SepaFlash® Silica Flash Column, Eluent of 0~20% MeOH/Dichloromethane@100 mL/min). Compound 3 (20 g, 52% yield) was obtained as a white solid.

General Procedure for Preparation of Compound 4

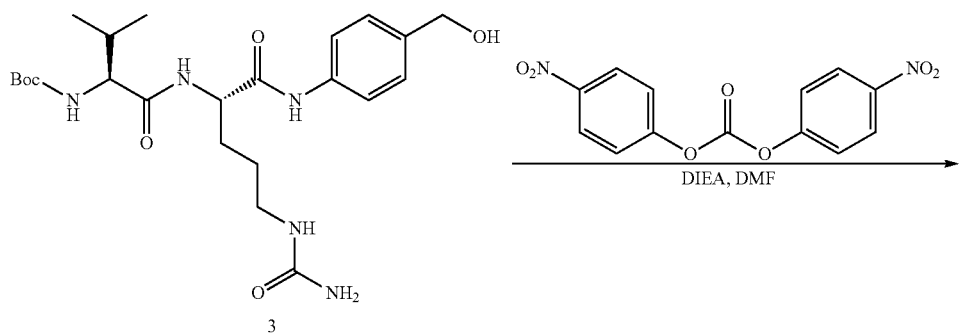

-continued

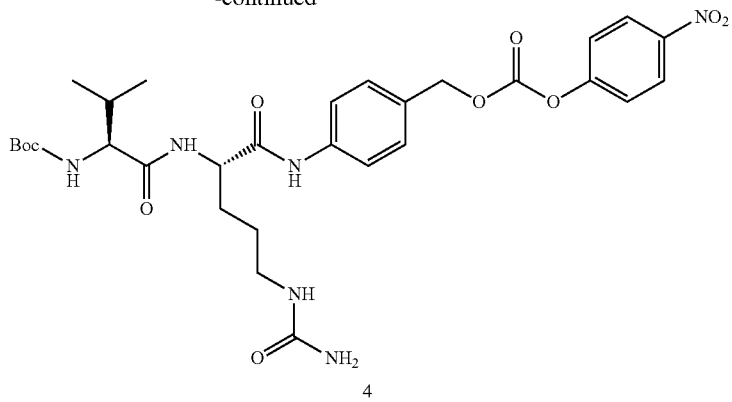

4

To a solution of compound 3 (5.0 g, 10.4 mmol) in DMF (40 mL) was added DIEA (5.4 g, 7.26 mL, 41.7 mmol) and bis(4-nitrophenyl) carbonate (12.7 g, 41.7 mmol). The mixture was stirred at 0° C. and under nitrogen for 1 hr. TLC (DCM:MeOH=10/1, $R_f$=0.66) indicated compound 3 was consumed completely and one new spot formed. The reaction was clean according to TLC and LCMS (ES8241-10-P1A, product: RT=1.15 min) showed the desired product was formed. The resulting reaction mixture was purified directly by prep-HPLC under neutral condition. Compound 4 (12 g, 60% yield) was obtained as a white solid.

General Procedure for Preparation of Compound 5

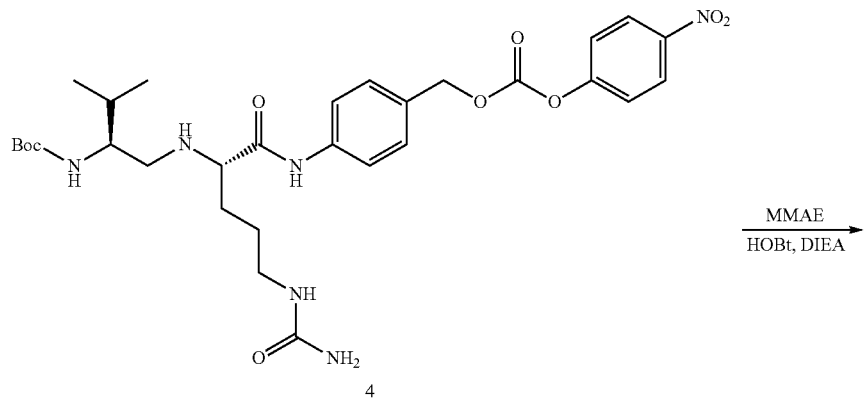

4

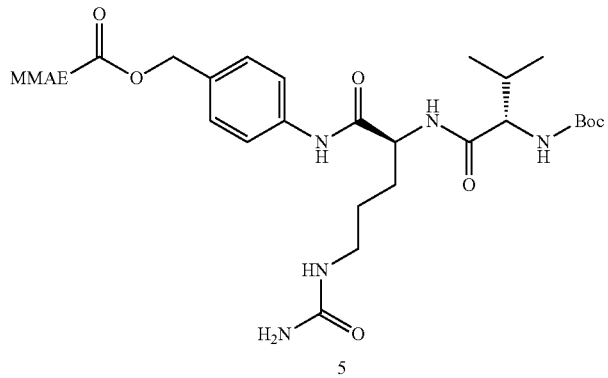

5

One batch of reaction was carried out as following: a solution of compound 4 (1.2 g, 1.68 mmol) in DMF (10 mL) was added DIEA (1.22 mL, 6.98 mmol,) under nitrogen atmosphere, the solution was stirred at 0° C. for 10 min, then HOBt (226 mg, 1.68 mmol) and MMAE (1.00 g, 1.40 mmol) were added thereto, the mixture was degassed and purged with N₂ for 3 times, which was stirred at 35° C. for 16 hr. LC-MS (ES8396-1-P1A1, product: RT=1.19 min) showed compound 4 was consumed completely and one main peak with desired mass was detected. The resulting reaction mixture of five batches was combined in 1 L of beaker and 500 mL water was added, then a precipitate was formed and filtered to collect. The precipitate was triturated with EtOAc overnight. Compound 5 (5 g, 59% yield) was obtained as a white solid.

General Procedure for Preparation of Compound 6

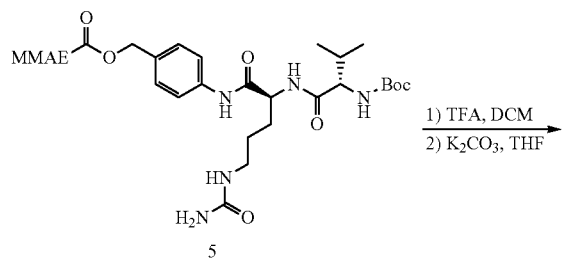

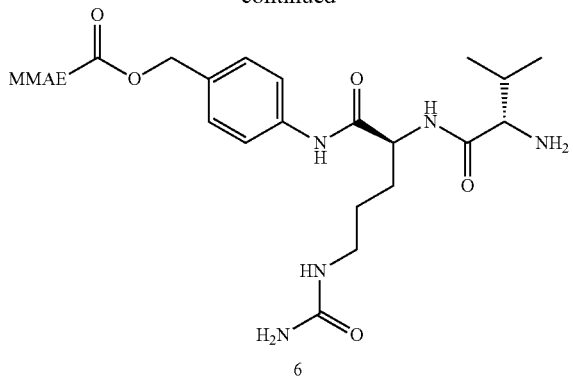

Compound 5 (3.3 g, 2.7 mmol) was dissolved in DCM (18 mL) in the presence of TFA (44 mmol, 3.5 mL), then the solution was stirred at 25° C. for 3 hr. Subsequently the reaction mixture was concentrated under reduced pressure to remove DCM and TFA to give a residue. The residue was dissolved in THF (20 mL), treated with K₂CO₃ (1.8 g, 13 mmol) and the mixture was further stirred at 25° C. for additional 12 hr. LC-MS (ES8396-2-P1B1, product: RT=1.04 min) showed one main peak with desired mass was detected. The reaction mixture was filtered and concentrated under reduced pressure to give a residue. The residue was dissolved in 10 mL of DMF and purified by prep-HPLC (neutral condition). Compound 6 (1.6 g, 53% yield) was obtained as a white solid.

General Procedure for Preparation of Compound 7-1

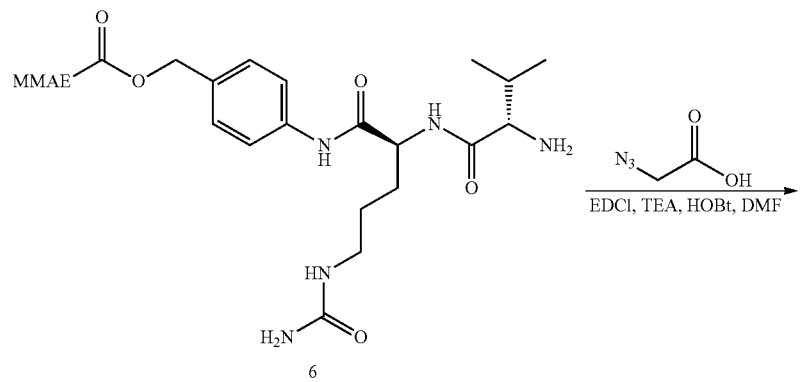

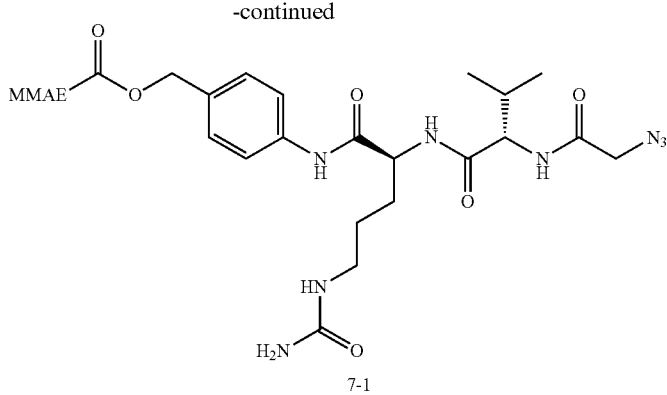

7-1

Compound 6 (1.2 g, 1.1 mmol) and 2-azidoacetic acid (162 mg, 1.6 mmol) were dissolved in DMF (10 mL). TEA (450 uL, 3.2 mmol), HOBt (217 mg, 1.6 mmol) and EDCI (307 mg, 1.6 mmol) were added to the solution under nitrogen, and the mixture was stirred at 0° C. for 30 min, then the mixture was warmed to 25° C. slowly with further stirring for 15.5 hr. LC-MS (ES8396-3-P1A, product: RT=1.04 min) showed compound 6 was consumed completely and one main peak with desired mass was detected. 2 mL of water was added to the reaction mixture to form a clear solution. Then the solution was purified directly by prep-HPLC under neutral condition. Compound 7-1 (0.9 g, 70% yield) was obtained as a white solid.

General Procedure for Preparation of BT17BDC-53

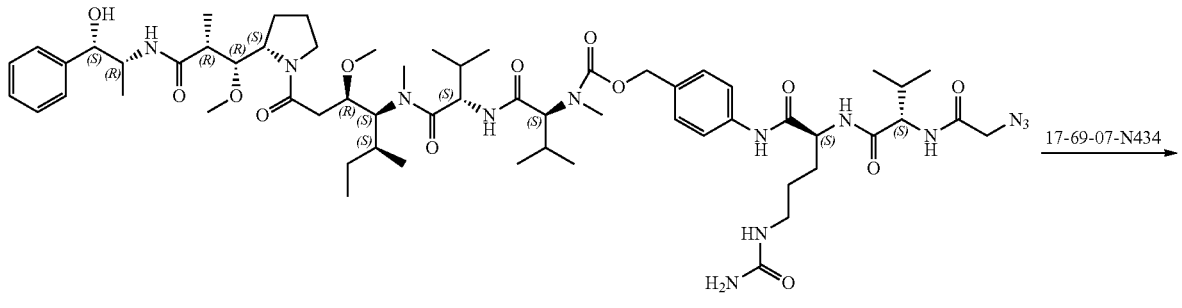

(2-azidoacetic-acid)-Val-Cit-PABC-MMAE

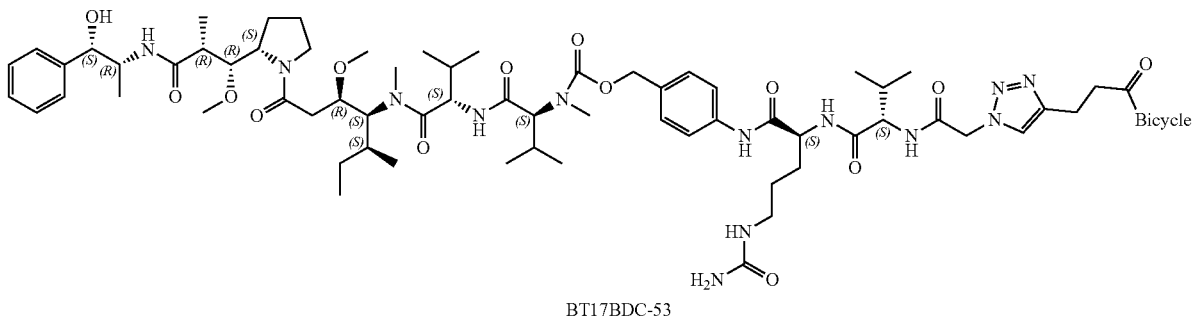

BT17BDC-53

To a mixture of (2-azidoacetic-acid)-Val-Cit-PABC-MMAE (16 mg, 13.26 umol, 1 eq) and BICYCLE alkyne (17-69-07-N434, 30 mg, 11.09 umol, 0.8 eq) in DMF (3 mL) and H$_2$O (2 mL) was added CuI (1.26 mg, 6.63 umol, 0.5 eq). The mixture was stirred at 25° C. under N$_2$ for 20 hr. LC-MS showed (2-azidoacetic-acid)-Val-Cit-PABC-MMAE was consumed completely and one main peak with desired MS was detected. The resulting reaction mixture was purified by prep-HPLC (TFA condition). Compound BT17BDC-53 (23.7 mg, 6.06 umol, 54.64% yield) was obtained as a white solid.

General Procedure for Preparation of BT17BDC-59

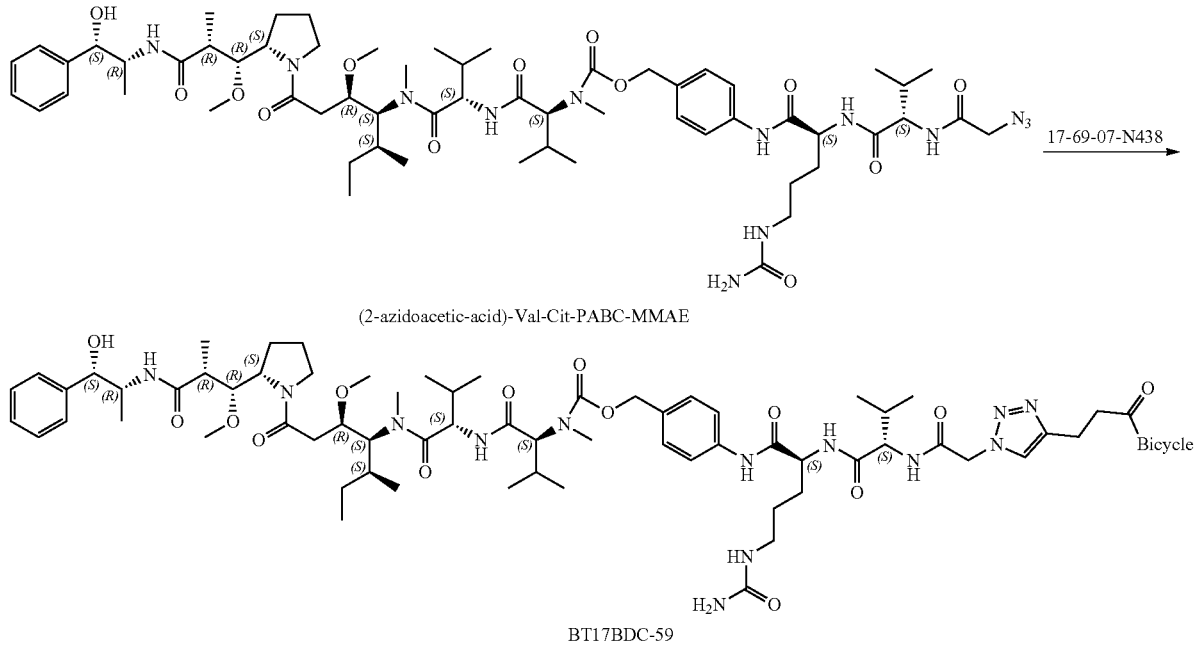

To a mixture of (2-azidoacetic-acid)-Val-Cit-PABC-MMAE (31 mg, 25.69 umol, 1.2 eq) and (17-69-07-N438, 40 mg, 20.8 umol, 1 eq) in DMF (3 mL) was added a solution of CuSO$_4$ (10.25 mg, 64.24 umol, 3 eq) in Water (0.4 mL) and a solution of Ascorbic Acid (37.71 mg, 214.12 umol, 10 eq) in Water (0.4 mL) under nitrogen. Then the mixture was stirred at 25° C. for 1 hr. LC-MS showed (2-azidoacetic-acid)-Val-Cit-PABC-MMAE was consumed completely and one main peak with desired MS was detected. The resulting reaction mixture was purified by prep-HPLC (TFA condition). BT17BDC-59 (26.7 mg, 8.53 umol, 41.02% yield) was obtained as a white solid.

General Procedure for Preparation of BT17BDC61

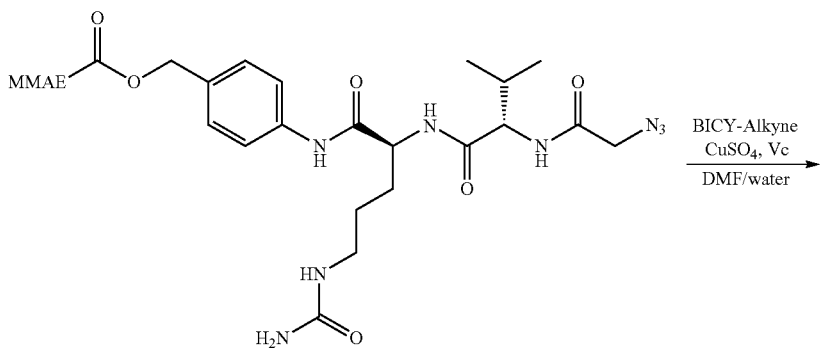

7-1

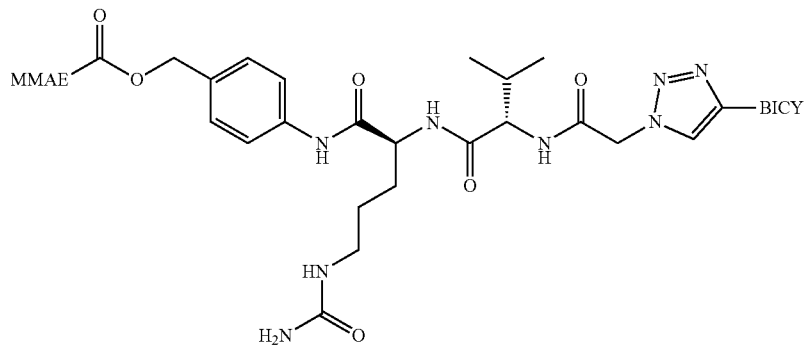

Compound 7-1 (250 mg, 207 umol) and BICY-ALKYNE 17-69-07-N450 (515 mg, 188 umol) were taken in an 50 mL of round flask, DMF (5 mL) was added, and followed by aqueous ascorbic acid solution (1 M, 1.88 mL) and aqueous $CuSO_4$ solution (1 M, 570 uL) under nitrogen atmosphere, then the mixture was stirred at 25° C. for 1 hr. LC-MS (ES8396-8-P1A, product: RT=1.03 min) showed BICY-ALKYNE was consumed completely and one main peak with desired mass was detected. The reaction mixture was filtered to remove the undissolved substance, filtrate was purified directly by prep-HPLC (TFA condition). BT17BDC61 (262 mg, 35% yield) was obtained as a white solid.

General Procedure for Preparation of BT17BDC62

Compound 7-1 (250 mg, 207 umol) and BICY-ALKYNE 17-69-07-N443 (368 mg, 188 umol) were taken in a 50 mL of round flask. DMF (5 mL) was added, followed by adding an aqueous solution of ascorbic acid (1 M, 1.88 mL) and a aqueous solution of $CuSO_4$ (1 M, 570 uL). Then the mixture was stirred at 25° C. for 1 hr. LC-MS (ES8396-9-P1A, product: RT=1.07 min) showed BICY-ALKYNE was consumed completely and one main peak with desired mass was detected. The reaction mixture was filtered to remove the undissolved substance, The resulting filtrate was purified directly by prep-HPLC (TFA condition). BT17BDC62 (253 mg, 42% yield) was obtained as a white solid.

Example 9

Figure 15A:
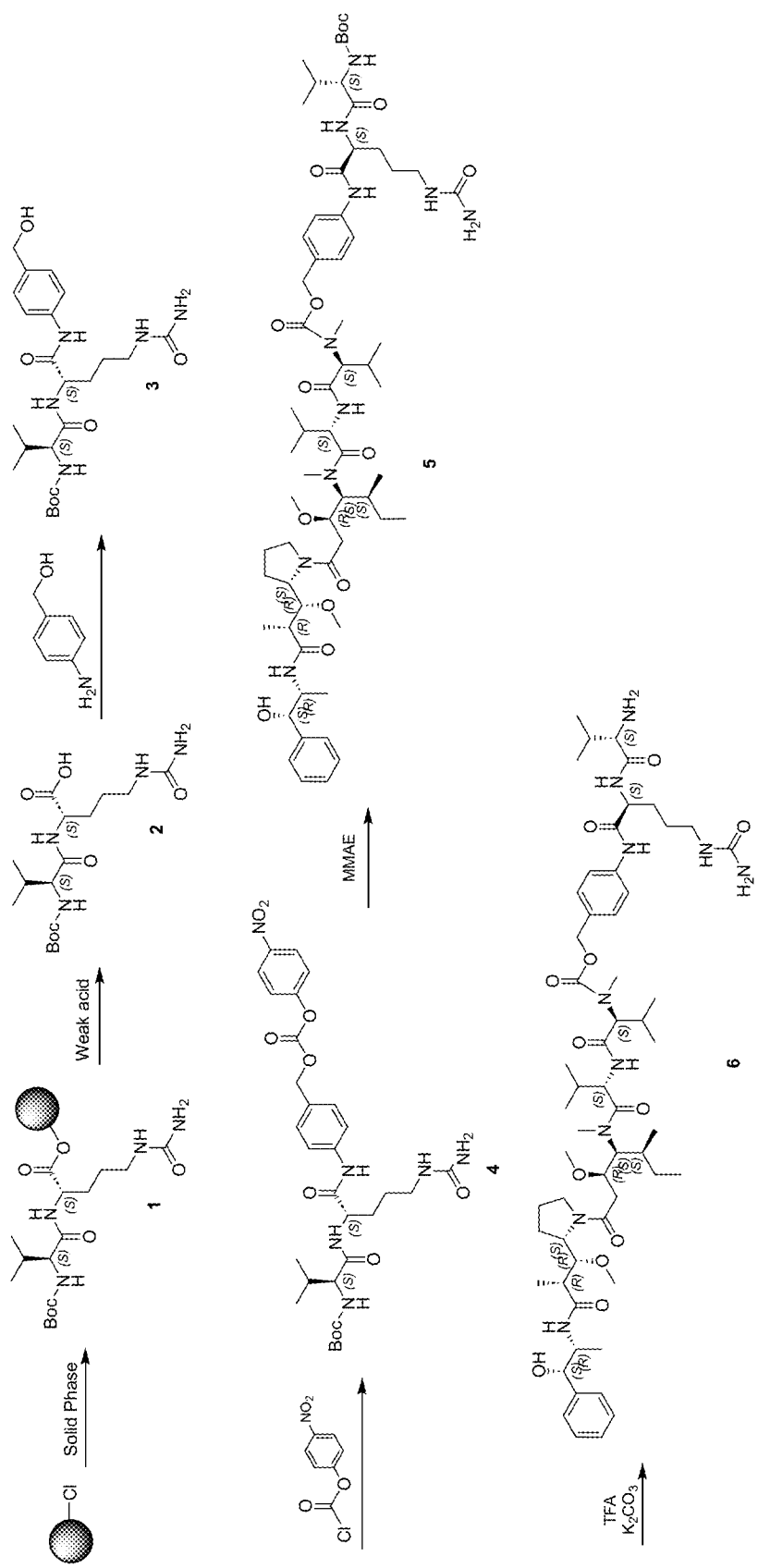
FIG. 15A and FIG. 15B each show part of a reaction scheme for preparation of a bicycle peptide-drug conjugate according to the invention by having an amido linkage.
Figure 15B:
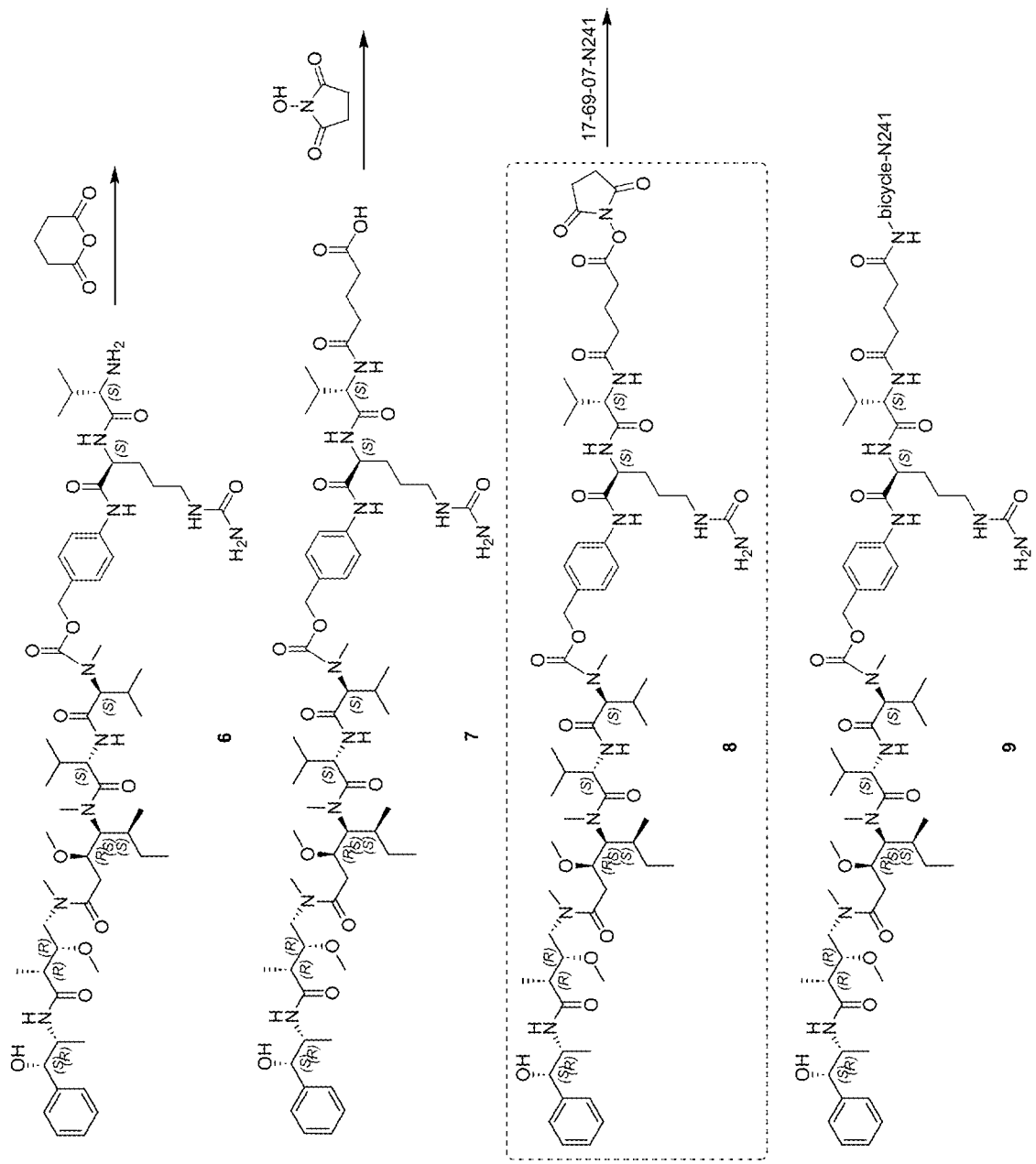
Figure 16:
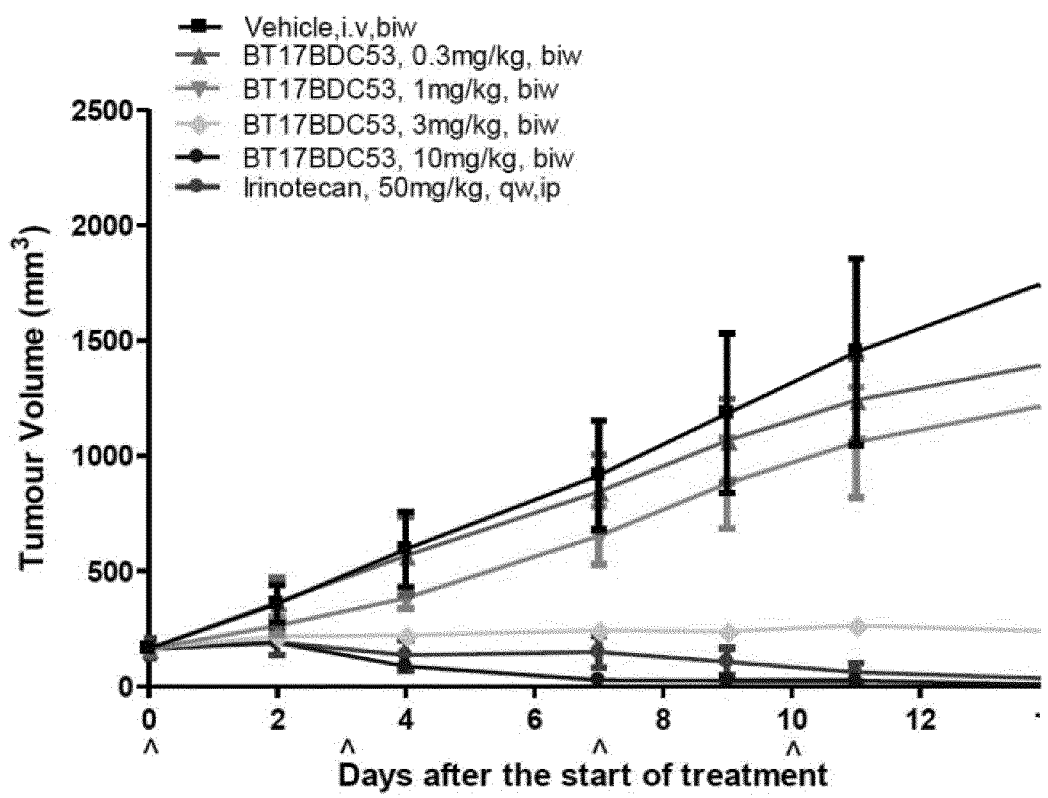
FIG. 16 shows tumor volume and body mass over time for Balb/c nude mice having HT1020 tumor cell tumors after treatment with a bicycle peptide-drug conjugate according to the invention.
Figure 16:
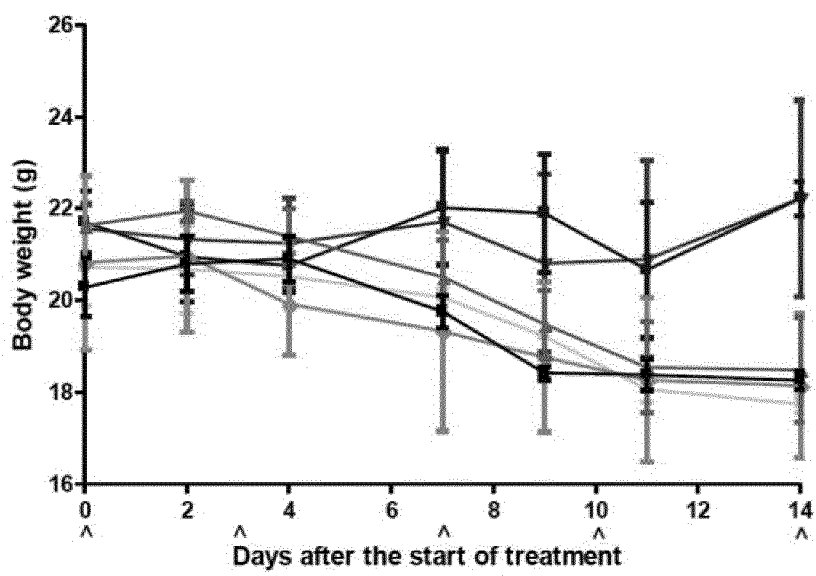
Figure 17:
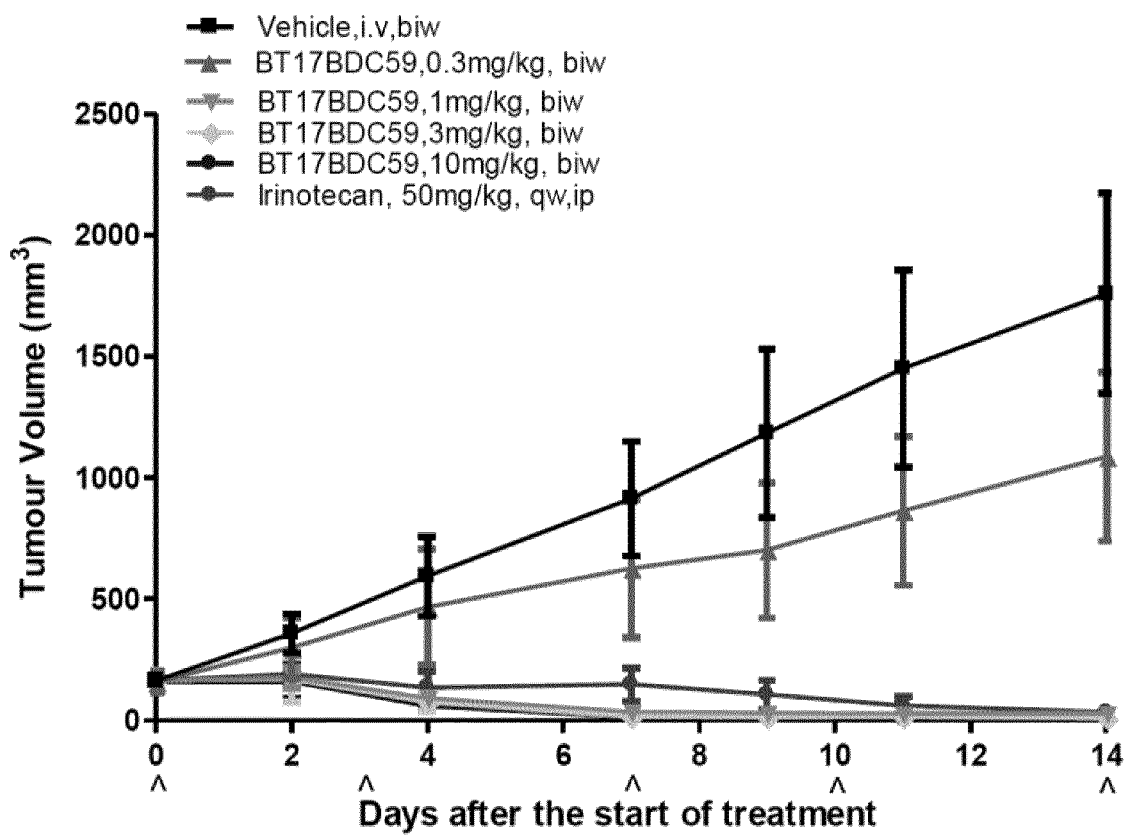
FIG. 17 shows tumor volume and body mass over time for Balb/c nude mice having HT1020 tumor cell tumors after treatment with a further bicycle peptide-drug conjugate according to the invention.
Figure 17:
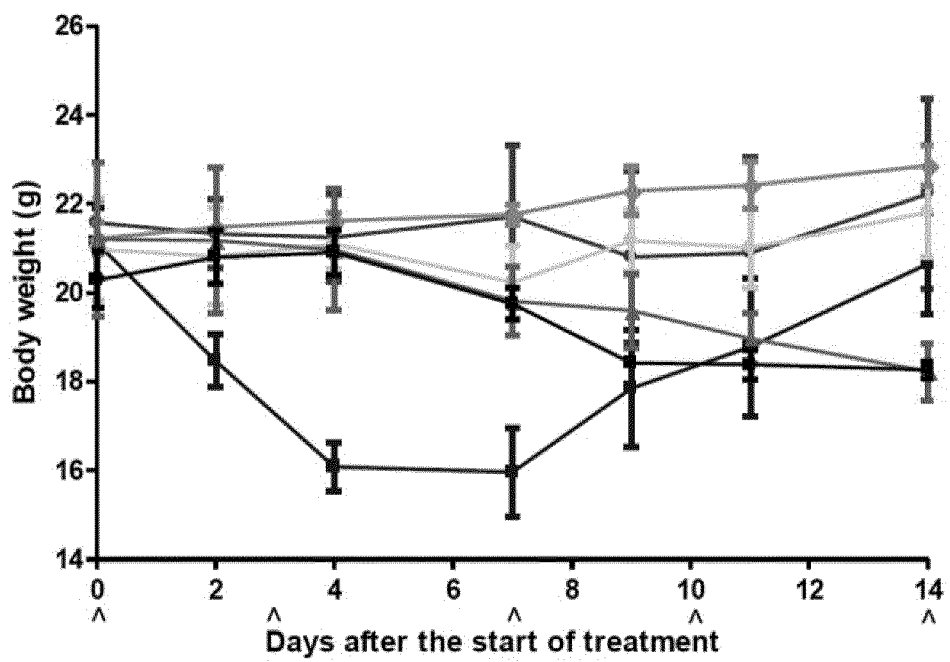
Figure 18:
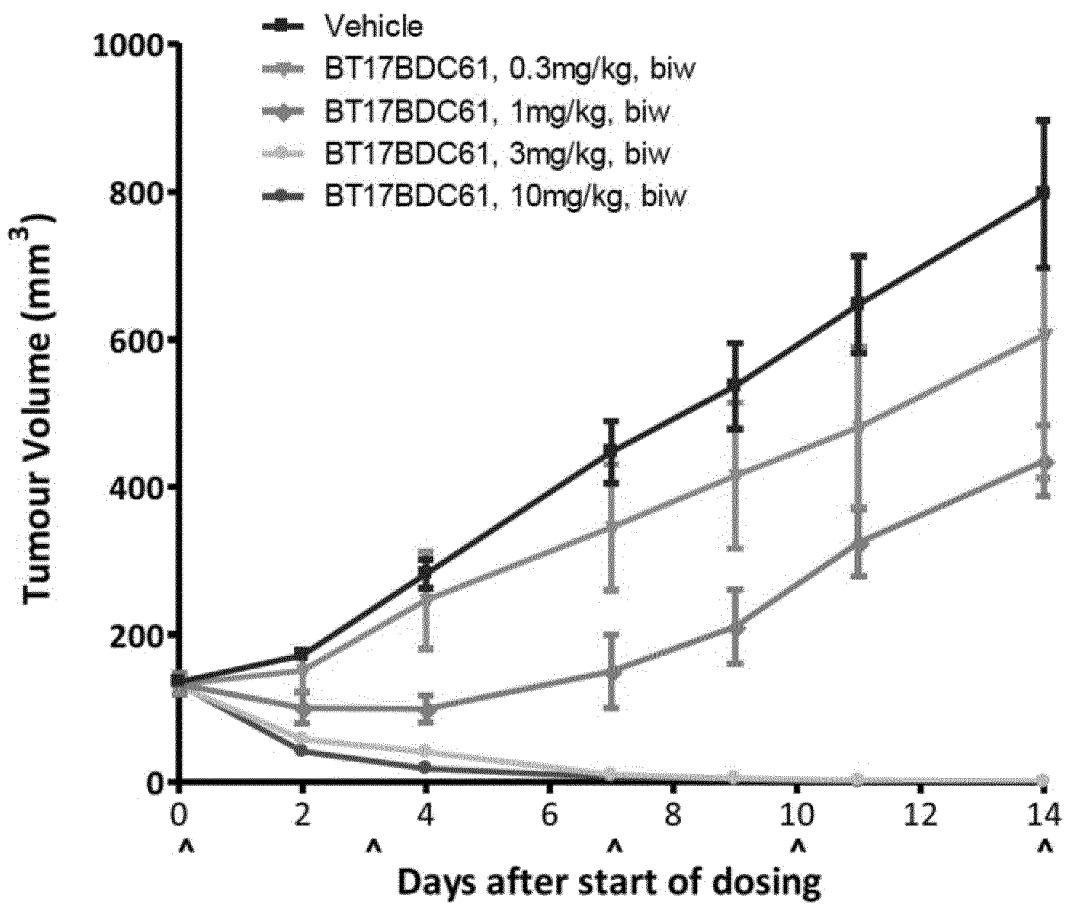
FIG. 18 shows tumor volume and body mass over time for Balb/c nude mice having HT1020 tumor cell tumors after treatment with a further bicycle peptide-drug conjugate according to the invention.
Figure 18:
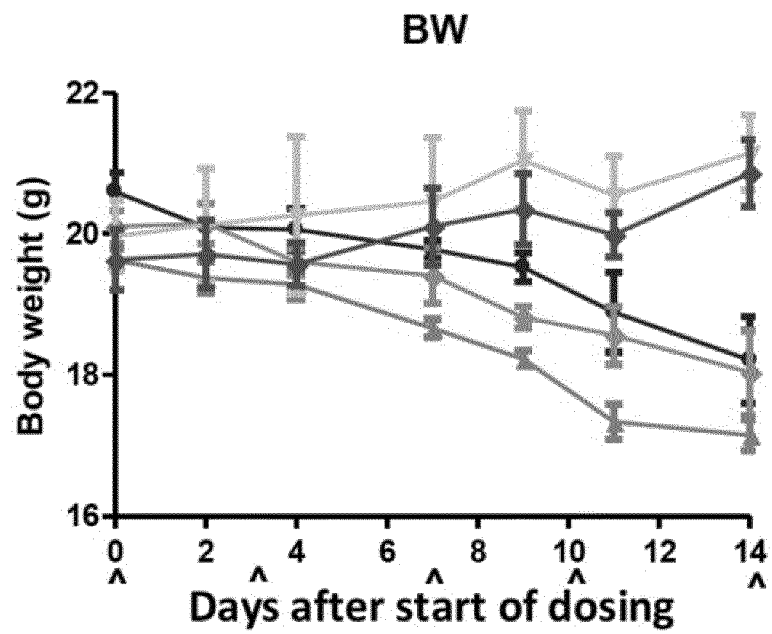
Figure 19:
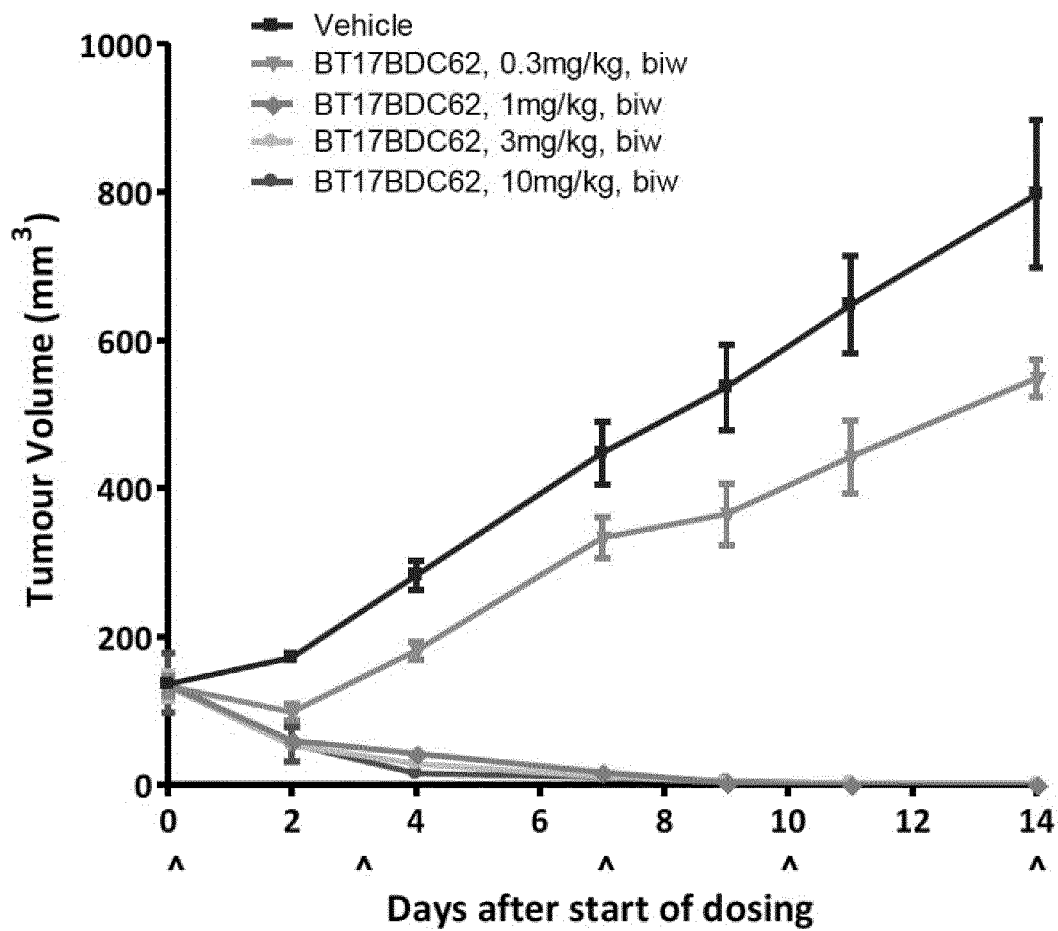
FIG. 19 shows tumor volume and body mass over time for Balb/c nude mice having HT1020 tumor cell tumors after treatment with a further bicycle peptide-drug conjugate according to the invention.
Figure 19:
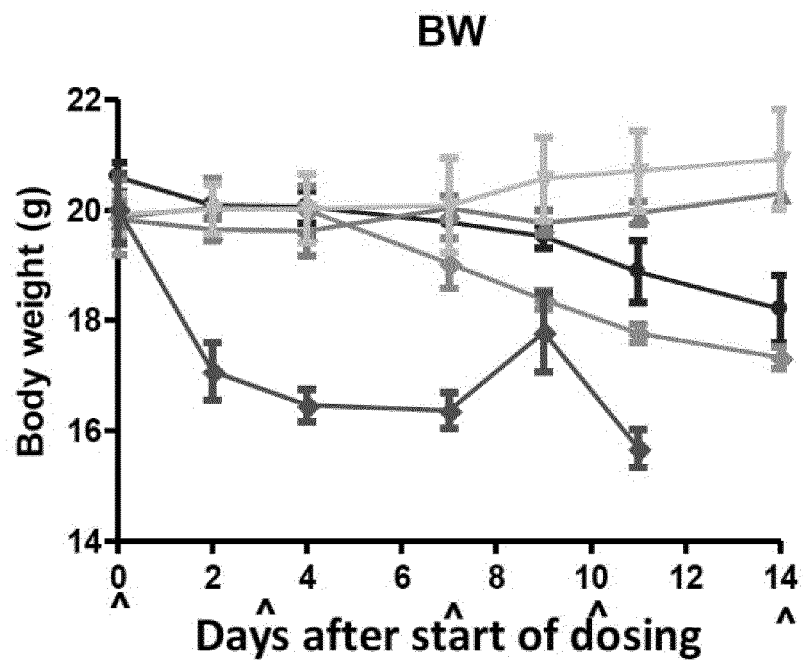
Figure 20:
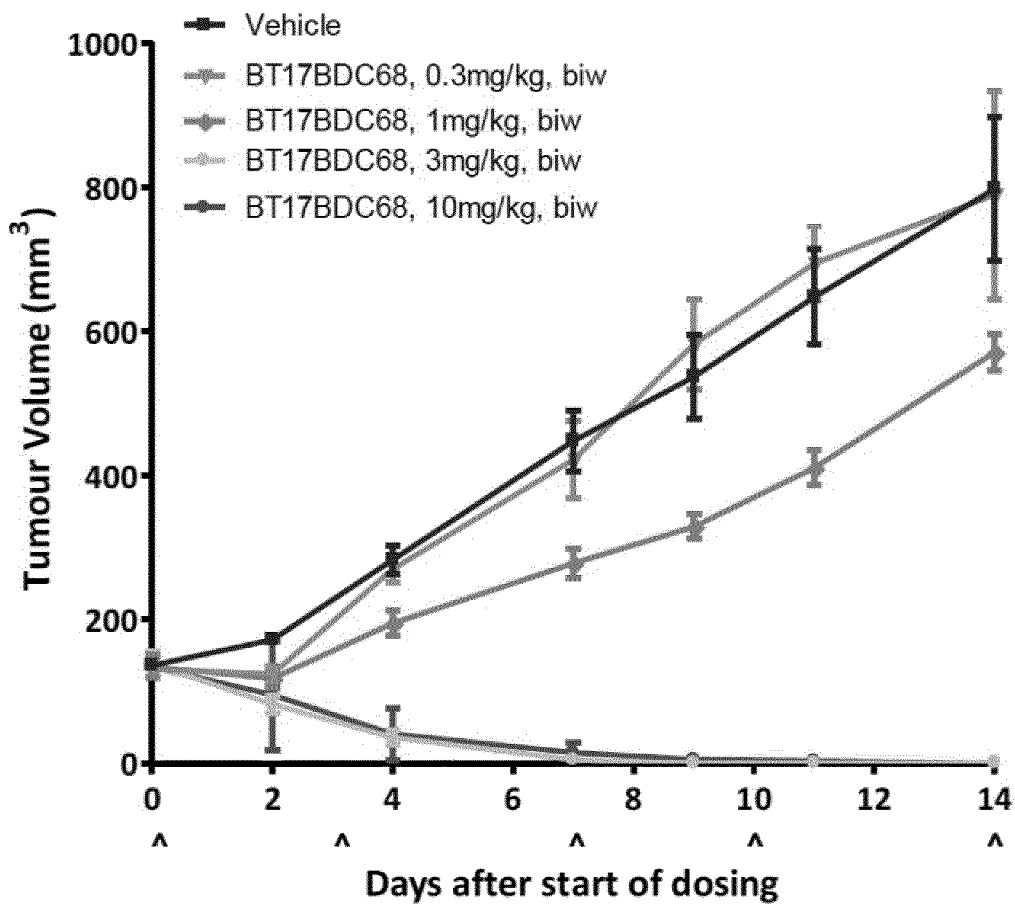
FIG. 20 shows tumor volume and body mass over time for Balb/c nude mice having HT1020 tumor cell tumors after treatment with a further bicycle peptide-drug conjugate according to the invention.
Figure 20:
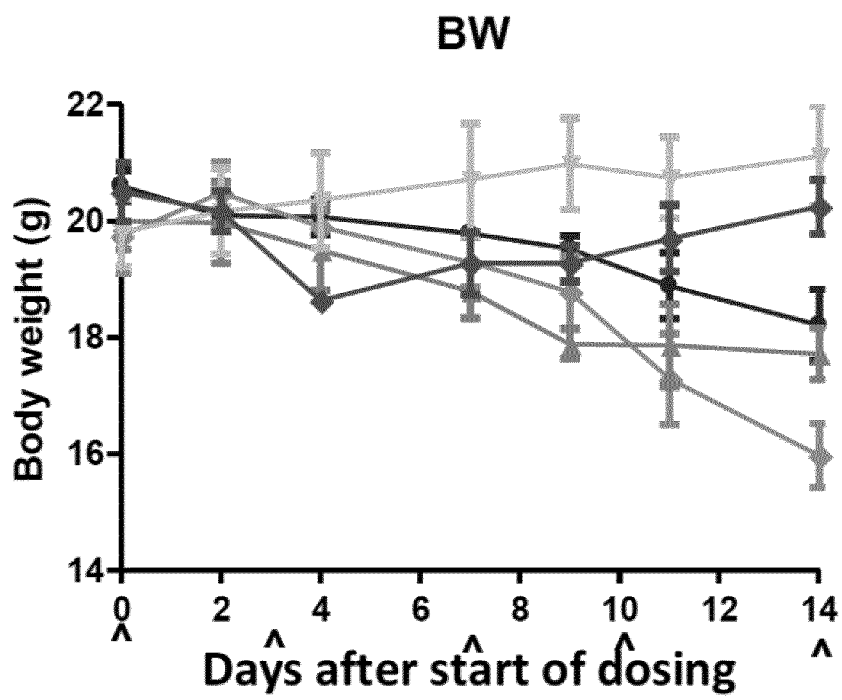

Bicycle-drug conjugates (BCDs) in which bicycle peptides according to the invention are coupled to monomethyl auristatin E (MMAE) by amide formation between a terminal glutaryl group of the linker and terminal amino of the peptide were prepared in accordance with the reaction scheme shown in FIG. 15. The steps of the reaction scheme were performed as follows.

General Procedure for Preparation of Compound 3

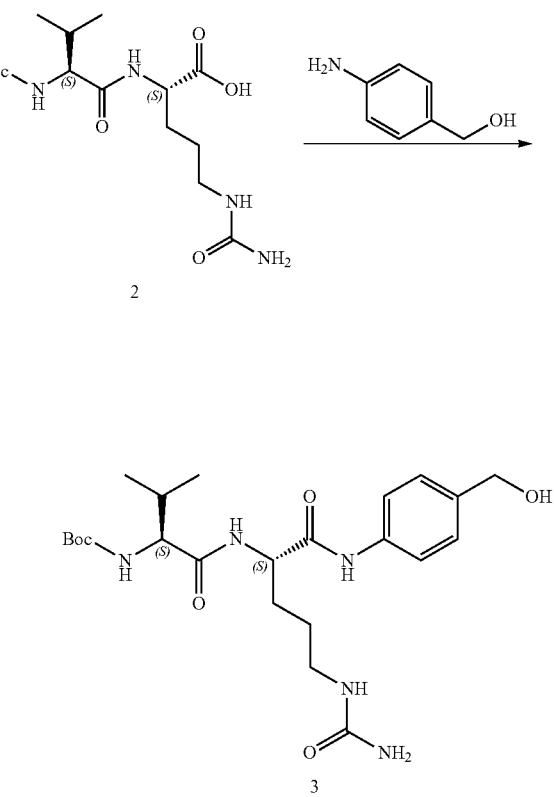

To a solution of Compound 2 (7.00 g, 18.70 mmol, 1.00 eq) in DCM (80.00 mL) and MeOH (40.00 mL) was added (4-aminophenyl)methanol (2.53 g, 20.56 mmol, 1.10 eq) and EEDQ (9.25 g, 37.39 mmol, 2.00 eq) in the dark. And the mixture was stirred at 25° C. for 8 hr. LC-MS showed Compound 2 was consumed completely and one main peak with desired MS was detected. The resulting reaction mixture was concentrated under reduced pressure to remove the solvent to give a residue. The residue was purified by flash silica gel chromatography (ISCO®; 120 g SepaFlash® Silica Flash Column, Eluent of 0~10% MeOH/DCM @ 85 mL/min). Compound 3 (7.00 g, 14.60 mmol, 78.06% yield) was obtained as a white solid.

General Procedure for Preparation of Compound 4

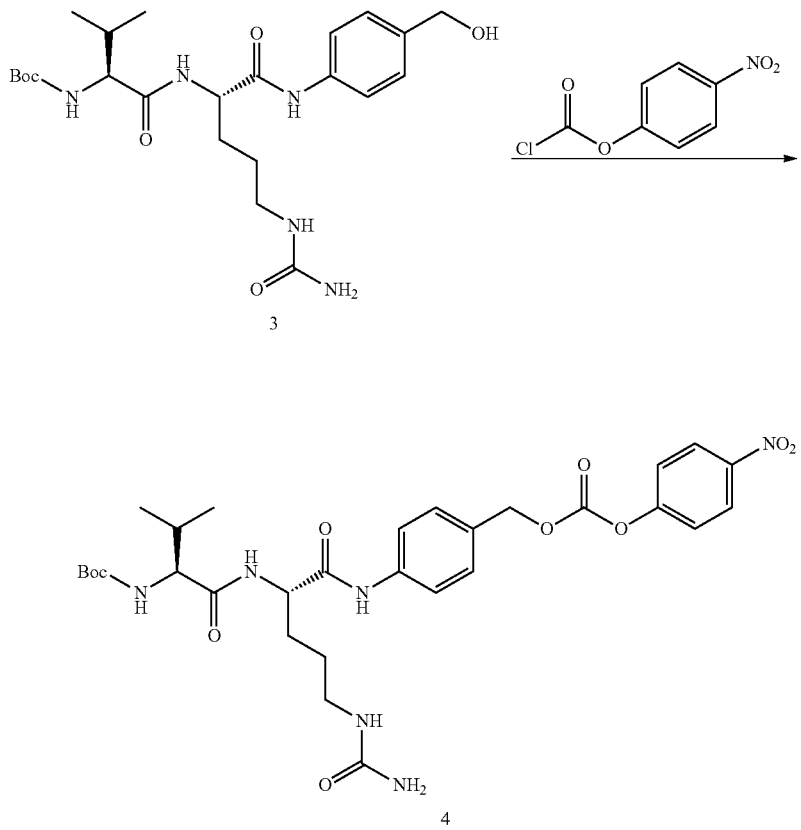

To a solution of Compound 3 (4.00 g, 8.34 mmol, 1.00 eq) and 4-nitrophenyl carbonochloridate (6.72 g, 33.36 mmol, 4.00 eq) in THF (20.00 mL) and DCM (10.00 mL) was added PYRIDINE (2.64 g, 33.36 mmol, 2.69 mL, 4.00 eq). And the reaction mixture was stirred at 25° C. for 5 hr. LC-MS showed Compound 3 was consumed completely and one main peak with desired MS was detected. The reaction mixture was concentrated under reduced pressure to give a residue, which was purified by flash silica gel chromatography (ISCO®; 120 g SepaFlash® Silica Flash Column, Eluent of 0~20% DM/MeOH @ 85 mL/min). Compound 4 (2.20 g, 3.41 mmol, 40.92% yield) was obtained as a white solid.

General Procedure for Preparation of Compound 5

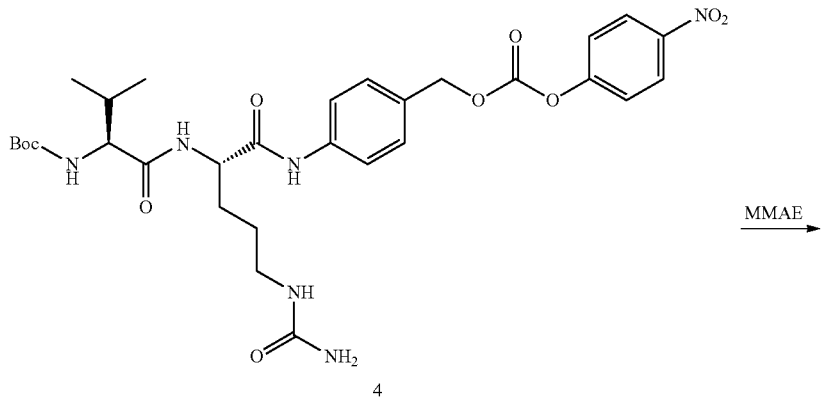

-continued

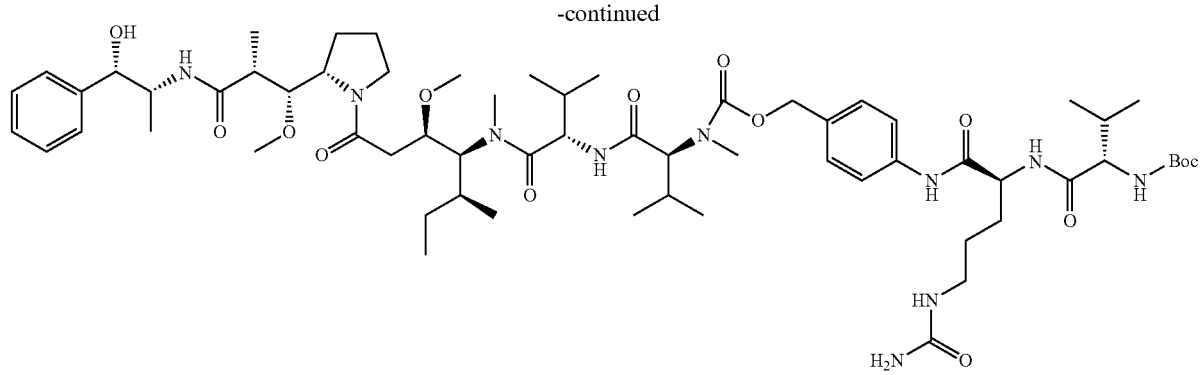

5

A mixture of Compound 4 (500.00 mg, 775.59 umol, 1.00 eq) and DIEA (1.00 g, 7.76 mmol, 1.35 mL, 10.00 eq) in DMF (10.00 mL) was stirred under nitrogen at 0° C. for 30 min. And MMAE (445.49 mg, 620.47 umol, 0.80 eq) and HOBt (104.80 mg, 775.59 umol, 1.00 eq) was added to the above mixture. The reaction mixture was stirred under nitrogen at 0° C. for 10 min and at 30° C. for additional 18 hr. LC-MS showed Compound 4 was consumed completely and one main peak with desired MS was detected. The resulting reaction mixture was purified directly by flash C18 gel chromatography (ISCO®; 330 g SepaFlash® C18 Flash Column, Eluent of 0-50% MeCN/H$_2$O @ 85 mL/min). Compound 5 (400.00 mg, 326.92 umol, 42.15% yield) was obtained as a white solid.

General Procedure for Preparation of Compound 6

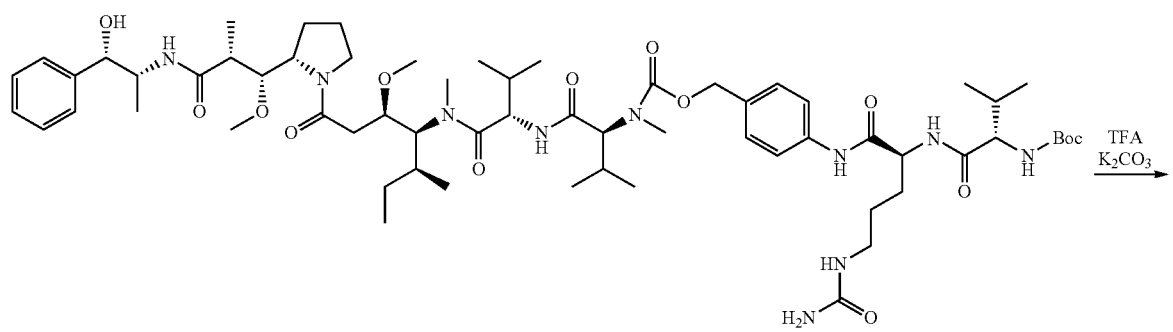

5

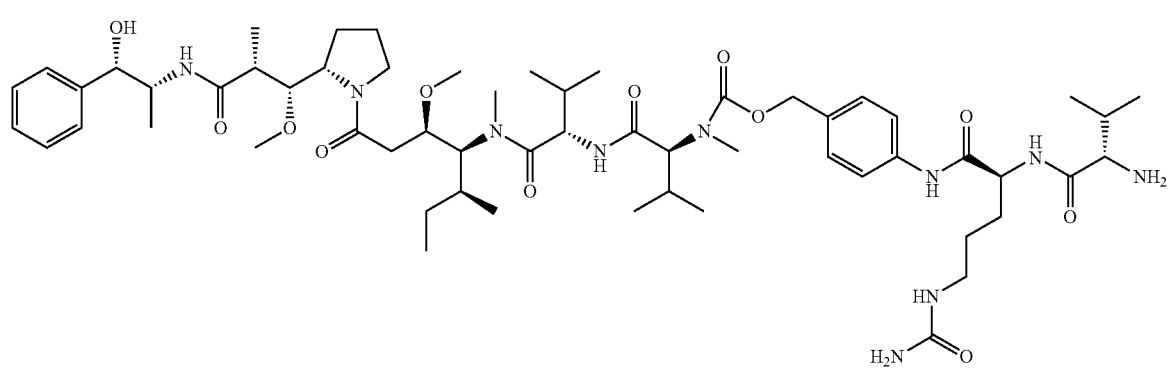

6

To a solution of Compound 5 (430.00 mg, 351.44 umol, 1.00 eq) in DCM (36.00 mL) was added TFA (6.16 g, 54.03 mmol, 4.00 mL, 153.73 eq) and the mixture was stirred at 25° C. for 2 hr. The mixture was then concentrated under reduced pressure to give a residue, which was dissolved in THF (10.00 mL), and $K_2CO_3$ (1.21 g, 8.79 mmol, 25.00 eq) was added to the mixture. The reaction was stirred at 25° C. for 12 hr. LC-MS showed Compound 5 was consumed completely and one main peak with desired MS was detected. The resulting reaction mixture was filtered and the filtrate was concentrated under reduced pressure to give a residue, which was purified by flash C18 gel chromatography (ISCO®; 120 g SepaFlash® C18 Flash Column, Eluent of 0~50% MeCN/$H_2O$@85 mL/min). Compound 6 (290.00 mg, 258.14 umol, 73.45% yield) was obtained as a white solid.

General Procedure for Preparation of Compound 7

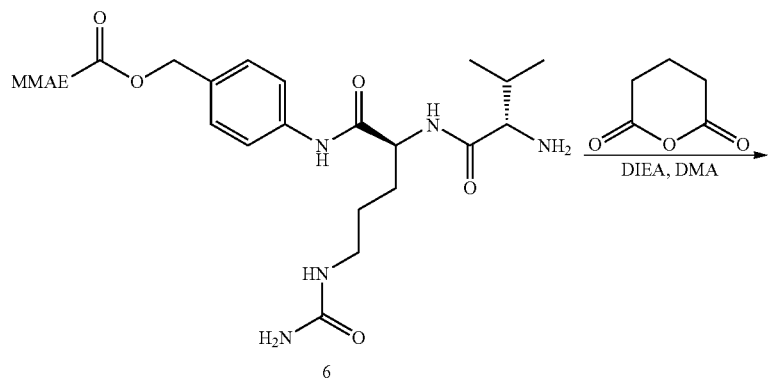

6

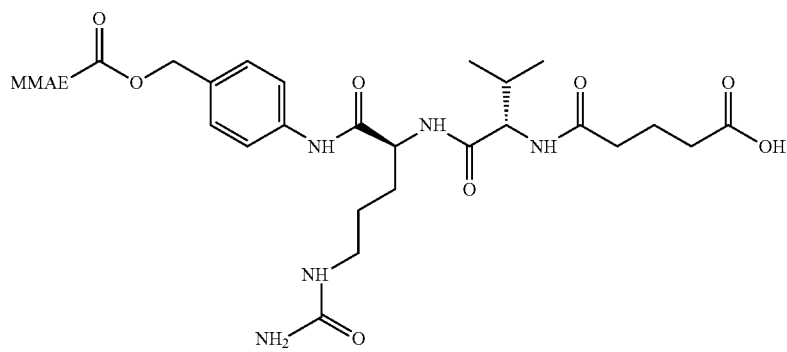

7-2

A vial containing (400 mg, 356 umol) was purged using a nitrogen balloon. Anhydrous DMA (5 mL) was added with stirring and the solution was cooled to 0° C. in an ice water bath. DIEA (130 uL, 712 umol) was then added and the reaction was stirred at 0° C. for 10 min. tetrahydropyran-2,6-dione (81 mg, 712 umol) was added and the ice bath was then removed. The reaction was stirred at 25° C. for 1 hr. LC-MS (ES8396-4-P1A, product: RT=1.08 min) showed compound 6 was consumed completely and one main peak with desired mass was detected. The mixture was diluted with 5 mL of water and then purified by prep-HPLC (neutral condition). Compound 7-2 (330 mg, 75% yield) was obtained as a white solid.

General Procedure for Preparation of Compound 8

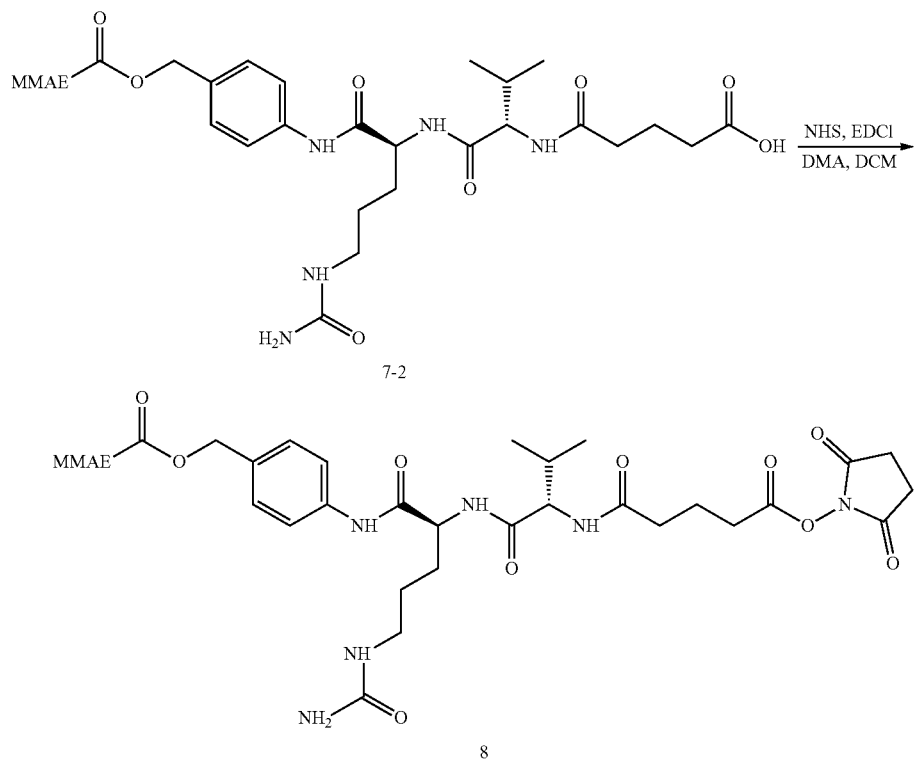

Compound 7-2 (330 mg, 267 umol) in anhydrous DMA (4.5 mL) and DCM (1.5 mL) was added HOSu (92 mg, 800 umol) under nitrogen with stirring for 10 min at 0° C. using an ice bath. Then EDCI (154 mg, 800 umol) was added to the mixture with further stirring at 25° C. for 16 hr. LC-MS (ES8396-5-P1A, product: RT=1.15 min) showed compound 7-2 was consumed completely and one main peak with desired mass was detected. The resulting reaction mixture was diluted with 5 mL of water and then purified by prep-HPLC (neutral condition). Compound 8 (250 mg, 70% yield) was obtained as a white solid.

General Procedure for Preparation of BT17BDC68

A 50 mL of round bottom flask which contained BICY-$NH_2$ 17-69-07-N451 (80.0 mg, 30 umol) in DMA (4 mL) was purged using nitrogen balloon. DIEA (20 uL, 114 umol) was then added with stirring at 25° C. for 10 min. Compound 8 (40 mg, 30 umol) was then added and the reaction was stirred under a positive nitrogen atmosphere for 18 hr at 25° C. LC-MS (ES6635-127-P1A1, product: RT=1.06 min) showed compound 8 was consumed completely and one main peak with desired MS was detected. The resulting reaction mixture was purified by prep-HPLC (TFA condition). BT17BDC68 (33.9 mg, 29% yield) was obtained as a white solid.

Example 10

The in vitro binding affinities of the bicycle peptide-drug conjugates prepared above were measured for MT1-MMP as previously described herein. The results were as follows.

| Compound ID | Parent Bicycle ID | Linker | Binding Affinity (Ki in nM) |
|---|---|---|---|
| BT17BDC-53 | 17-69-07-N434 | Triazole-2-azidoacetyl-ValCit-PABC | Human ki = 3.6, 2.5; rat/mouse ki = 1.8, 1.6 |
| BT17BDC-59 | 17-69-07-N438 | Triazole-2-azidoacetyl-ValCit-PABC | Human ki = 2.8, 2.7; rat/mouse ki = 1.8, 1.7 |
| BT17BDC-61 | 17-69-07-N450 | Triazole-2-azidoacetyl-ValCit-PABC | Human ki = 3.2, 2.9; rat/mouse ki = 1.8, 1.6 |

-continued

| Compound ID | Parent Bicycle ID | Linker | Binding Affinity (Ki in nM) |
|---|---|---|---|
| BT17BDC-62 | 17-69-07-N443 | Triazole-2-azidoacetyl-ValCit-PABC-CO2— | Human ki = 3.9, 3.3; rat/mouse ki = 2.1, 1.9 |
| BT17BDC-68 | 17-69-07-N451 | glutaryl-Val-Cit PABC | Human ki = 2.9, 3.3; rat/mouse ki = 1.8, 1.6 |

It can be seen that in all cases the binding affinity of the bicycle peptides is maintained following conjugation to MMAE.

Example 11

The plasma stability of BT17BDC-53 in mouse and human serums was studied. The conjugate was found to be stable ($T_1/2$ greater than 50 hours at 4 μm concentration) in both mouse and human serums. The stability appears to be slightly greater than that of the corresponding conjugates in which the peptide is linked to the scaffold by three thioether linkages.

Example 12

The in vivo efficacy against tumors of the bicycle peptide drug conjugates prepared above were evaluated as follows.

HT1080 tumor cells were maintained in vitro as a monolayer culture in EMEM medium supplemented with 10% heat inactivated fetal bovine serum at 37 C in an atmosphere of 5% $CO_2$ and air. The tumor cells were routinely subcultured twice weekly by trypsin-EDTA treatment. The cells growing in an exponential growth phase were harvested and counted for tumor inoculation.

BALB/c nude mice were inoculated subcutaneously at the right flank with HT1080 tumor cells (% x $10^6$) in 0.2 ml of PBS for tumor development. 39 animals were randomized when the average tumor volume reached 134 $mm^2$.

The BDC compounds were formulated at 0.03 mg/ml in a vehicle buffer containing 25 mM histidine and 10% Sucrose. The formulations were administered twice weekly (biw) at 0.3, 1, 3 and 10 mg/kg. Tumor volume and body weight were measured up to 14 days from the first dosing. The results are shown in FIGS. 16-20.

The results show that all five of the conjugates that were tested exhibit strong dose-dependent tumor inhibition. At doses of 3 mg/kg and 10 mg/kg the tumors appeared to be completely eradicated. BT17BDC53, 61 and 68 were well tolerated up to 10 mg/kg. BT17BDC62 was tolerated up to about 5 mg/kg. BT17BDC59 was tolerated up to 3 mg/kg. This suggests that the presence of the N-terminal Sar10 spacer in BT17BDC53, 61 and 68 reduces the systemic toxicity of the conjugates.

All publications mentioned in the above specification are herein incorporated by reference. Various modifications and variations of the described aspects and embodiments of the present invention will be apparent to those skilled in the art without departing from the scope of the present invention. Although the present invention has been described in connection with specific preferred embodiments, it should be understood that the invention as claimed should not be unduly limited to such specific embodiments. Indeed, various modifications of the described modes for carrying out the invention which are apparent to those skilled in the art are intended to be within the scope of the following claims.

The invention claimed is:

1. A compound comprising a looped peptide structure attached via at least one alkylamino linkage to a molecular scaffold, wherein the looped peptide structure is a Bicycle structure comprising two peptide loops subtended between three linkages to the scaffold, a central linkage attached to the two peptide loops, wherein the molecular scaffold comprises a tris-substituted (hetero)aromatic or (hetero)alicyclic moiety, and wherein the looped peptide structure comprises a sequence:

$(X)_l A_1 (X)_m A_2 (X)_n A_3 (X)_o$;

or a pharmaceutically acceptable salt thereof,
wherein:
$A_1$, $A_2$ and $A_3$ are selected from cysteine, Dap, N-AlkDap, or N-HAlkDap, provided that at least one of $A_1$, $A_2$ and $A_3$ is Dap, N-AlkDap or N-HAlkDap, wherein each of $A_1$, $A_2$ and $A_3$ attaches to the molecular scaffold via a thioether linkage or an alkylamino linkage;
X is any amino acid residue;
m is 3, 4, 5, 6, 7, 8 or 9;
n is 3, 4, 5, 6, 7, 8 or 9;
l is a number between 0 and 20; and
o is a number between 0 and 20.

2. The compound according to claim 1, wherein at least one of $A_1$, $A_2$ and $A_3$ is cysteine, attaching to the molecular scaffold via a thioether linkage.

3. The compound according to claim 1, wherein two of $A_1$, $A_2$ and $A_3$ is Dap, N-AlkDap or N-HAlkDap, attaching to the molecular scaffold by alkylamino linkages.

4. The compound according to claim 1, wherein the molecular scaffold comprises a (hetero)aromatic moiety.

5. The compound according to claim 1, wherein the molecular scaffold comprises a tris-substituted six-membered (hetero)aromatic or (hetero)alicyclic ring structure.

6. The compound according to claim 1, wherein the molecular scaffold is a tris-methylene substituted (hetero)aromatic or (hetero)alicyclic moiety.

7. The compound according to claim 1, wherein the molecular scaffold comprises alkylamino linkages at alpha or beta-carbon positions with respect to a carbonyl, situated on a (hetero)aryl scaffold or a (hetero)alicyclic scaffold.

8. The compound according to claim 1, wherein the compound is a drug conjugate comprising the looped peptide structure conjugated to one or more effector and/or functional groups selected from a cytotoxic agent, a metal chelator, and an antibody or a fragment thereof.

9. The compound as defined in claim 8, wherein the effector and/or functional groups are a cytotoxic agent or a metal chelator.

10. The compound as defined in claim 9, wherein the cytotoxic agent is linked to the looped peptide structure by a cleavable bond.

11. The compound as defined in claim 9, wherein the cytotoxic agent is selected from DM1 and MMAE.

12. The compound as defined in claim 9, wherein the compound is a drug conjugate having a structure:

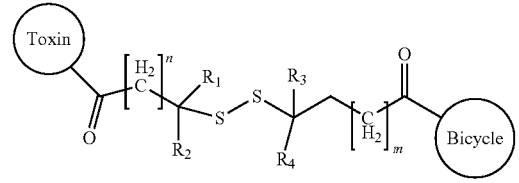

wherein: $R_1$, $R_2$, $R_3$ and $R_4$ are each independently hydrogen or C1-C6 alkyl groups;
Toxin is a cytotoxic agent;
Bicycle is the looped peptide structure;
n is an integer selected from 1 to 10; and
m is an integer selected from 0 to 10.

13. The compound as defined in claim 12, wherein either: $R_1$, $R_2$, $R_3$ and $R_4$ are all H; or $R_1$, $R_2$, $R_3$ are all H and $R_4$=methyl; or $R_1$, $R_2$=methyl and $R_3$, $R_4$=H; or $R_1$, $R_3$=methyl and $R_2$, $R_4$=H; or $R_1$, $R_2$=H and $R_3$, $R_4$=C1-C6 alkyl.

14. The compound as defined in claim 9, wherein the compound is a drug conjugate having a structure:

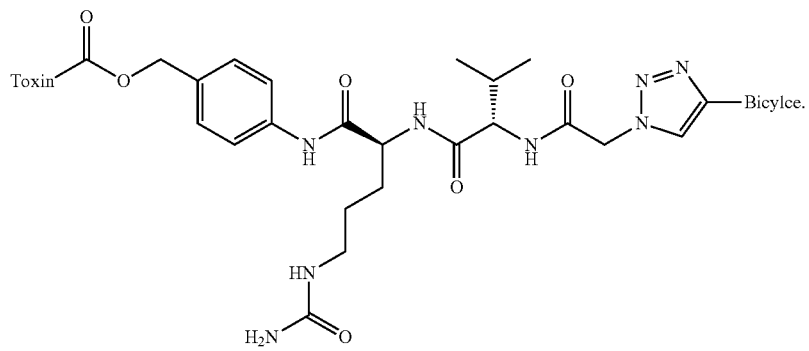

15. The compound as defined in claim 9, wherein the compound is a drug conjugate having a structure:

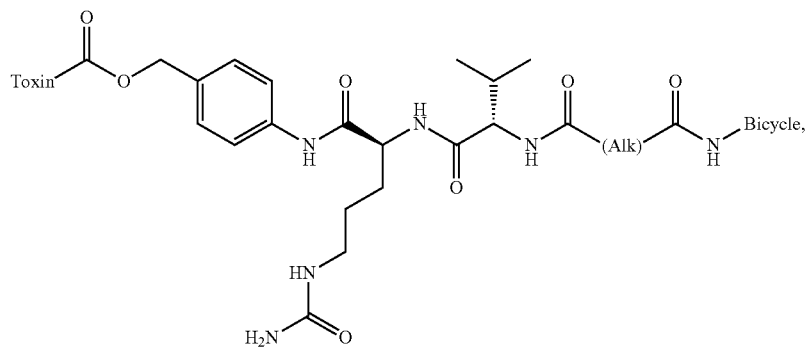

wherein (Alk) is a linear or branched alkylene group of formula $CH_2n$ wherein n is from 1 to 10, and Bicycle is the looped peptide structure.

16. The compound according to claim 1, wherein $A_1$, $A_2$ and $A_3$ are Dap, N-AlkDap or N-HAlkDap, attaching to the molecular scaffold by alkylamino linkages.

17. The compound according to claim 1, wherein the molecular scaffold is 1,3,5-Tris(bromomethyl)benzene (TBMB), 2,4,6-tris(bromomethyl) mesitylene, or 1,3,5-tris (bromoacetamido)benzene (TBAB).

18. The compound as defined in claim 10, wherein the cleavable bond is a disulphide bond.

19. The compound as defined in claim 9, wherein the cytotoxic agent is linked to the looped peptide structure by a valine-citrulline group.

20. The compound as defined in claim 9, wherein the cytotoxic agent is linked to the looped peptide structure by a linker comprising a triazole group.

21. The compound as defined in claim 9, wherein the cytotoxic agent is linked to the looped peptide structure by a para-amino benzyl carbamate (PABC) group.

22. The compound according to claim 8, wherein the antibody or a fragment thereof comprises an antibody light chain constant region (CL), an antibody CH1 heavy chain domain, an antibody CH2 heavy chain domain, an antibody CH3 heavy chain domain, or any combination thereof.

23. The compound according to claim 8, wherein the antibody or a fragment thereof is an Fc region of an IgG molecule.

* * * * *

SEQUENCE LISTING

```
<160> NUMBER OF SEQ ID NOS: 35

<210> SEQ ID NO 1
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"
<220> FEATURE:
<221> NAME/KEY: VARIANT
<222> LOCATION: (1)..(1)
<223> OTHER INFORMATION: /replace="Dap" or "N-AlkDap" or "N-HAlkDap"
<220> FEATURE:
<221> NAME/KEY: MOD_RES
<222> LOCATION: (2)..(2)
<223> OTHER INFORMATION: Any amino acid
<220> FEATURE:
<221> NAME/KEY: VARIANT
<222> LOCATION: (3)..(3)
<223> OTHER INFORMATION: /replace="Cys" or "Gln" or "Met" or "Ser" or
    "Thr" or "Gly" or "Ala" or "Ile" or "Leu" or "Pro" or "Val"
<220> FEATURE:
<221> NAME/KEY: MOD_RES
<222> LOCATION: (4)..(5)
<223> OTHER INFORMATION: Any amino acid
<220> FEATURE:
<221> NAME/KEY: VARIANT
<222> LOCATION: (7)..(7)
<223> OTHER INFORMATION: /replace="Dap" or "N-AlkDap" or "N-HAlkDap"
<220> FEATURE:
<221> NAME/KEY: MOD_RES
<222> LOCATION: (12)..(13)
<223> OTHER INFORMATION: Any amino acid
```

```
<220> FEATURE:
<221> NAME/KEY: VARIANT
<222> LOCATION: (14)..(14)
<223> OTHER INFORMATION: /replace="Dap" or "N-AlkDap" or "N-HAlkDap"
<220> FEATURE:
<221> NAME/KEY: MISC_FEATURE
<222> LOCATION: (1)..(14)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 1

Cys Xaa Asn Xaa Xaa Gly Cys Glu Asp Phe Tyr Xaa Xaa Cys
1               5                   10

<210> SEQ ID NO 2
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Dap" or "N-AlkDap" or "N-HAlkDap"
<220> FEATURE:
<221> NAME/KEY: VARIANT
<222> LOCATION: (7)..(7)
<223> OTHER INFORMATION: /replace="Dap" or "N-AlkDap" or "N-HAlkDap"
<220> FEATURE:
<221> NAME/KEY: VARIANT
<222> LOCATION: (14)..(14)
<223> OTHER INFORMATION: /replace="Dap" or "N-AlkDap" or "N-HAlkDap"
<220> FEATURE:
<221> NAME/KEY: MISC_FEATURE
<222> LOCATION: (1)..(14)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 2

Cys Tyr Asn Glu Phe Gly Cys Glu Asp Phe Tyr Asp Ile Cys
1               5                   10

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000
```

```
<210> SEQ ID NO 6
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Dap" or "N-AlkDap" or "N-HAlkDap"
<220> FEATURE:
<221> NAME/KEY: VARIANT
<222> LOCATION: (2)..(2)
<223> OTHER INFORMATION: /replace="Met" or "Phe" or "Val"
<220> FEATURE:
<221> NAME/KEY: VARIANT
<222> LOCATION: (3)..(3)
<223> OTHER INFORMATION: /replace="Cys" or "Gln" or "Met" or "Ser" or
      "Thr" or "Gly" or "Ala" or "Ile" or "Leu" or "Pro" or "Val"
<220> FEATURE:
<221> NAME/KEY: VARIANT
<222> LOCATION: (4)..(4)
<223> OTHER INFORMATION: /replace="Cys" or "Gln" or "Met" or "Ser" or
      "Thr" or "Asp" or "Glu"
<220> FEATURE:
<221> NAME/KEY: VARIANT
<222> LOCATION: (5)..(5)
<223> OTHER INFORMATION: /replace="Trp" or "Tyr"
<220> FEATURE:
<221> NAME/KEY: VARIANT
<222> LOCATION: (7)..(7)
<223> OTHER INFORMATION: /replace="Dap" or "N-AlkDap" or "N-HAlkDap"
<220> FEATURE:
<221> NAME/KEY: VARIANT
<222> LOCATION: (12)..(12)
<223> OTHER INFORMATION: /replace="Glu"
<220> FEATURE:
<221> NAME/KEY: VARIANT
<222> LOCATION: (13)..(13)
<223> OTHER INFORMATION: /replace="Ala" or "Ile" or "Leu" or "Pro" or
      "Val"
<220> FEATURE:
<221> NAME/KEY: VARIANT
<222> LOCATION: (14)..(14)
<223> OTHER INFORMATION: /replace="Dap" or "N-AlkDap" or "N-HAlkDap"
<220> FEATURE:
<221> NAME/KEY: MISC_FEATURE
<222> LOCATION: (1)..(14)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 6

Cys Tyr Asn Asn Phe Gly Cys Glu Asp Phe Tyr Asp Gly Cys
1               5                   10

<210> SEQ ID NO 7
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Dap" or "N-AlkDap" or "N-HAlkDap"
<220> FEATURE:
<221> NAME/KEY: VARIANT
<222> LOCATION: (2)..(2)
```

```
<223> OTHER INFORMATION: /replace="Met" or "Phe" or "Val"
<220> FEATURE:
<221> NAME/KEY: VARIANT
<222> LOCATION: (3)..(3)
<223> OTHER INFORMATION: /replace="Gly"
<220> FEATURE:
<221> NAME/KEY: VARIANT
<222> LOCATION: (4)..(4)
<223> OTHER INFORMATION: /replace="Gln"
<220> FEATURE:
<221> NAME/KEY: VARIANT
<222> LOCATION: (7)..(7)
<223> OTHER INFORMATION: /replace="Dap" or "N-AlkDap" or "N-HAlkDap"
<220> FEATURE:
<221> NAME/KEY: VARIANT
<222> LOCATION: (14)..(14)
<223> OTHER INFORMATION: /replace="Dap" or "N-AlkDap" or "N-HAlkDap"
<220> FEATURE:
<221> NAME/KEY: MISC_FEATURE
<222> LOCATION: (1)..(14)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 7

Cys Tyr Asn Glu Phe Gly Cys Glu Asp Phe Tyr Asp Ile Cys
1               5                   10

<210> SEQ ID NO 8
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Dap" or "N-AlkDap" or "N-HAlkDap"
<220> FEATURE:
<221> NAME/KEY: VARIANT
<222> LOCATION: (2)..(2)
<223> OTHER INFORMATION: /replace="Met" or "Phe"
<220> FEATURE:
<221> NAME/KEY: VARIANT
<222> LOCATION: (3)..(3)
<223> OTHER INFORMATION: /replace="Gly"
<220> FEATURE:
<221> NAME/KEY: VARIANT
<222> LOCATION: (4)..(4)
<223> OTHER INFORMATION: /replace="Gln"
<220> FEATURE:
<221> NAME/KEY: VARIANT
<222> LOCATION: (7)..(7)
<223> OTHER INFORMATION: /replace="Dap" or "N-AlkDap" or "N-HAlkDap"
<220> FEATURE:
<221> NAME/KEY: VARIANT
<222> LOCATION: (14)..(14)
<223> OTHER INFORMATION: /replace="Dap" or "N-AlkDap" or "N-HAlkDap"
<220> FEATURE:
<221> NAME/KEY: MISC_FEATURE
<222> LOCATION: (1)..(14)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 8
```

Cys Tyr Asn Glu Phe Gly Cys Glu Asp Phe Tyr Asp Ile Cys
1               5                   10

<210> SEQ ID NO 9
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Dap" or "N-AlkDap" or "N-HAlkDap"
<220> FEATURE:
<221> NAME/KEY: VARIANT
<222> LOCATION: (2)..(2)
<223> OTHER INFORMATION: /replace="Met"
<220> FEATURE:
<221> NAME/KEY: VARIANT
<222> LOCATION: (4)..(4)
<223> OTHER INFORMATION: /replace="Gln"
<220> FEATURE:
<221> NAME/KEY: VARIANT
<222> LOCATION: (7)..(7)
<223> OTHER INFORMATION: /replace="Dap" or "N-AlkDap" or "N-HAlkDap"
<220> FEATURE:
<221> NAME/KEY: VARIANT
<222> LOCATION: (14)..(14)
<223> OTHER INFORMATION: /replace="Dap" or "N-AlkDap" or "N-HAlkDap"
<220> FEATURE:
<221> NAME/KEY: MISC_FEATURE
<222> LOCATION: (1)..(14)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 9

Cys Tyr Asn Glu Phe Gly Cys Glu Asp Phe Tyr Asp Ile Cys
1               5                   10

<210> SEQ ID NO 10
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Dap" or "N-AlkDap" or "N-HAlkDap"
<220> FEATURE:
<221> NAME/KEY: VARIANT
<222> LOCATION: (7)..(7)
<223> OTHER INFORMATION: /replace="Dap" or "N-AlkDap" or "N-HAlkDap"
<220> FEATURE:
<221> NAME/KEY: VARIANT
<222> LOCATION: (14)..(14)
<223> OTHER INFORMATION: /replace="Dap" or "N-AlkDap" or "N-HAlkDap"
<220> FEATURE:
<221> NAME/KEY: MISC_FEATURE
<222> LOCATION: (1)..(14)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 10

Cys Met Asn Gln Phe Gly Cys Glu Asp Phe Tyr Asp Ile Cys
1               5                   10

<210> SEQ ID NO 11
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Dap" or "N-AlkDap" or "N-HAlkDap"
<220> FEATURE:
<221> NAME/KEY: VARIANT
<222> LOCATION: (7)..(7)
<223> OTHER INFORMATION: /replace="Dap" or "N-AlkDap" or "N-HAlkDap"
<220> FEATURE:
<221> NAME/KEY: VARIANT
<222> LOCATION: (14)..(14)
<223> OTHER INFORMATION: /replace="Dap" or "N-AlkDap" or "N-HAlkDap"
<220> FEATURE:
<221> NAME/KEY: MISC_FEATURE
<222> LOCATION: (1)..(14)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 11

Cys Phe Gly Glu Phe Gly Cys Glu Asp Phe Tyr Asp Ile Cys
1               5                   10

<210> SEQ ID NO 12
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Dap" or "N-AlkDap" or "N-HAlkDap"
<220> FEATURE:
<221> NAME/KEY: VARIANT
<222> LOCATION: (7)..(7)
<223> OTHER INFORMATION: /replace="Dap" or "N-AlkDap" or "N-HAlkDap"
<220> FEATURE:
<221> NAME/KEY: VARIANT
<222> LOCATION: (14)..(14)
<223> OTHER INFORMATION: /replace="Dap" or "N-AlkDap" or "N-HAlkDap"
<220> FEATURE:
<221> NAME/KEY: MISC_FEATURE
<222> LOCATION: (1)..(14)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 12

Cys Val Asn Glu Phe Gly Cys Glu Asp Phe Tyr Asp Ile Cys
1               5                   10

```
<210> SEQ ID NO 13
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Dap" or "N-AlkDap" or "N-HAlkDap"
<220> FEATURE:
<221> NAME/KEY: VARIANT
<222> LOCATION: (7)..(7)
<223> OTHER INFORMATION: /replace="Dap" or "N-AlkDap" or "N-HAlkDap"
<220> FEATURE:
<221> NAME/KEY: VARIANT
<222> LOCATION: (14)..(14)
<223> OTHER INFORMATION: /replace="Dap" or "N-AlkDap" or "N-HAlkDap"
<220> FEATURE:
<221> NAME/KEY: MISC_FEATURE
<222> LOCATION: (1)..(14)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 13

Cys Phe Asn Glu Phe Gly Cys Glu Asp Phe Tyr Asp Ile Cys
1               5                   10

<210> SEQ ID NO 14
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Dap" or "N-AlkDap" or "N-HAlkDap"
<220> FEATURE:
<221> NAME/KEY: VARIANT
<222> LOCATION: (7)..(7)
<223> OTHER INFORMATION: /replace="Dap" or "N-AlkDap" or "N-HAlkDap"
<220> FEATURE:
<221> NAME/KEY: VARIANT
<222> LOCATION: (14)..(14)
<223> OTHER INFORMATION: /replace="Dap" or "N-AlkDap" or "N-HAlkDap"
<220> FEATURE:
<221> NAME/KEY: MISC_FEATURE
<222> LOCATION: (1)..(14)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 14

Cys Tyr Asn Glu Tyr Gly Cys Glu Asp Phe Tyr Asp Ile Cys
1               5                   10

<210> SEQ ID NO 15
<211> LENGTH: 14
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (1)..(1)
<223> OTHER INFORMATION: /replace="Dap" or "N-AlkDap" or "N-HAlkDap"
<220> FEATURE:
<221> NAME/KEY: VARIANT
<222> LOCATION: (7)..(7)
<223> OTHER INFORMATION: /replace="Dap" or "N-AlkDap" or "N-HAlkDap"
<220> FEATURE:
<221> NAME/KEY: VARIANT
<222> LOCATION: (14)..(14)
<223> OTHER INFORMATION: /replace="Dap" or "N-AlkDap" or "N-HAlkDap"
<220> FEATURE:
<221> NAME/KEY: MISC_FEATURE
<222> LOCATION: (1)..(14)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 15

Cys Tyr Asn Glu Trp Gly Cys Glu Asp Phe Tyr Asp Ile Cys
1               5                   10

<210> SEQ ID NO 16
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: beta-Ala
<220> FEATURE:
<221> NAME/KEY: MOD_RES
<222> LOCATION: (2)..(11)
<223> OTHER INFORMATION: Sarcosine
<220> FEATURE:
<221> NAME/KEY: VARIANT
<222> LOCATION: (13)..(13)
<223> OTHER INFORMATION: /replace="Dap" or "N-AlkDap" or "N-HAlkDap"
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (17)..(17)
<223> OTHER INFORMATION: Fmoc-L-1-Naphthylalanine
<220> FEATURE:
<221> NAME/KEY: MOD_RES
<222> LOCATION: (18)..(18)
<223> OTHER INFORMATION: D-amino acid
<220> FEATURE:
<221> NAME/KEY: VARIANT
<222> LOCATION: (19)..(19)
<223> OTHER INFORMATION: /replace="Dap" or "N-AlkDap" or "N-HAlkDap"
<220> FEATURE:
<221> NAME/KEY: MOD_RES
<222> LOCATION: (25)..(25)
<223> OTHER INFORMATION: Fmoc-alpha-tert-butylglycine
<220> FEATURE:
<221> NAME/KEY: VARIANT
<222> LOCATION: (26)..(26)
<223> OTHER INFORMATION: /replace="Dap" or "N-AlkDap" or "N-HAlkDap"
<220> FEATURE:
```

```
<221> NAME/KEY: MISC_FEATURE
<222> LOCATION: (1)..(26)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 16

Ala Xaa Xaa Xaa Xaa Xaa Xaa Xaa Xaa Xaa Xaa Ala Cys Ala Asn Glu
1               5                   10                  15

Ala Ala Cys Glu Asp Phe Tyr Asp Gly Cys
            20                  25

<210> SEQ ID NO 17
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: VARIANT
<222> LOCATION: (2)..(2)
<223> OTHER INFORMATION: /replace="Dap" or "N-AlkDap" or "N-HAlkDap"
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: Fmoc-L-1-Naphthylalanine
<220> FEATURE:
<221> NAME/KEY: MOD_RES
<222> LOCATION: (7)..(7)
<223> OTHER INFORMATION: D-amino acid
<220> FEATURE:
<221> NAME/KEY: VARIANT
<222> LOCATION: (8)..(8)
<223> OTHER INFORMATION: /replace="Dap" or "N-AlkDap" or "N-HAlkDap"
<220> FEATURE:
<221> NAME/KEY: MOD_RES
<222> LOCATION: (14)..(14)
<223> OTHER INFORMATION: Fmoc-alpha-tert-butylglycine
<220> FEATURE:
<221> NAME/KEY: VARIANT
<222> LOCATION: (15)..(15)
<223> OTHER INFORMATION: /replace="Dap" or "N-AlkDap" or "N-HAlkDap"
<220> FEATURE:
<221> NAME/KEY: MISC_FEATURE
<222> LOCATION: (1)..(15)
<223> OTHER INFORMATION: /note="Variant residues given in the sequence
      have no preference with respect to those in the annotations
      for variant positions"
<220> FEATURE:
<221> NAME/KEY: source
<223> OTHER INFORMATION: /note="See specification as filed for detailed
      description of substitutions and preferred embodiments"

<400> SEQUENCE: 17

Ala Cys Ala Asn Glu Ala Ala Cys Glu Asp Phe Tyr Asp Gly Cys
1               5                   10                  15

<210> SEQ ID NO 18
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                          Synthetic 6xHis tag"

<400> SEQUENCE: 18

His His His His His His
1               5

<210> SEQ ID NO 19
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Dap
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (6)..(6)
<223> OTHER INFORMATION: L-1-Naphthylalanine
<220> FEATURE:
<221> NAME/KEY: MOD_RES
<222> LOCATION: (7)..(7)
<223> OTHER INFORMATION: D-Ala
<220> FEATURE:
<221> NAME/KEY: MOD_RES
<222> LOCATION: (14)..(14)
<223> OTHER INFORMATION: tert-butylglycine
<220> FEATURE:
<221> NAME/KEY: MOD_RES
<222> LOCATION: (15)..(15)
<223> OTHER INFORMATION: Dap
<220> FEATURE:
<221> NAME/KEY: MISC_FEATURE
<222> LOCATION: (1)..(15)
<223> OTHER INFORMATION: /note="Variant residues given in the sequence
      have no preference with respect to those in the annotations
      for variant positions"

<400> SEQUENCE: 19

Ala Xaa Xaa Asn Glu Xaa Xaa Cys Glu Asp Phe Phe Asp Xaa Xaa
1               5                   10                  15

<210> SEQ ID NO 20
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: PYA
<220> FEATURE:
<221> NAME/KEY: MOD_RES
<222> LOCATION: (3)..(3)
<223> OTHER INFORMATION: Dap
<220> FEATURE:
<221> NAME/KEY: MOD_RES
<222> LOCATION: (4)..(4)
<223> OTHER INFORMATION: D-Ala
<220> FEATURE:
<221> NAME/KEY: MOD_RES
<222> LOCATION: (7)..(7)
<223> OTHER INFORMATION: L-1-Naphthylalanine
<220> FEATURE:
<221> NAME/KEY: MOD_RES
```

```
<222> LOCATION: (8)..(8)
<223> OTHER INFORMATION: D-Ala
<220> FEATURE:
<221> NAME/KEY: MOD_RES
<222> LOCATION: (15)..(15)
<223> OTHER INFORMATION: tert-butylglycine
<220> FEATURE:
<221> NAME/KEY: MOD_RES
<222> LOCATION: (16)..(16)
<223> OTHER INFORMATION: Dap

<400> SEQUENCE: 20

Xaa Ala Xaa Xaa Asn Glu Xaa Xaa Cys Glu Asp Phe Tyr Asp Xaa Xaa
1               5                   10                  15

<210> SEQ ID NO 21
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: beta-Ala
<220> FEATURE:
<221> NAME/KEY: MOD_RES
<222> LOCATION: (2)..(11)
<223> OTHER INFORMATION: Sarcosine
<220> FEATURE:
<221> NAME/KEY: MOD_RES
<222> LOCATION: (13)..(13)
<223> OTHER INFORMATION: Dap
<220> FEATURE:
<221> NAME/KEY: MOD_RES
<222> LOCATION: (14)..(14)
<223> OTHER INFORMATION: D-Ala
<220> FEATURE:
<221> NAME/KEY: MOD_RES
<222> LOCATION: (17)..(17)
<223> OTHER INFORMATION: L-1-Naphthylalanine
<220> FEATURE:
<221> NAME/KEY: MOD_RES
<222> LOCATION: (18)..(18)
<223> OTHER INFORMATION: D-Ala
<220> FEATURE:
<221> NAME/KEY: MOD_RES
<222> LOCATION: (25)..(25)
<223> OTHER INFORMATION: tert-butylglycine
<220> FEATURE:
<221> NAME/KEY: MOD_RES
<222> LOCATION: (26)..(26)
<223> OTHER INFORMATION: Dap

<400> SEQUENCE: 21

Xaa Xaa Xaa Xaa Xaa Xaa Xaa Xaa Xaa Xaa Xaa Ala Xaa Xaa Asn Glu
1               5                   10                  15

Xaa Xaa Cys Glu Asp Phe Tyr Asp Xaa Xaa
            20                  25

<210> SEQ ID NO 22
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Dap(Me)
```

```
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (6)..(6)
<223> OTHER INFORMATION: L-1-Naphthylalanine
<220> FEATURE:
<221> NAME/KEY: MOD_RES
<222> LOCATION: (7)..(7)
<223> OTHER INFORMATION: D-Ala
<220> FEATURE:
<221> NAME/KEY: MOD_RES
<222> LOCATION: (8)..(8)
<223> OTHER INFORMATION: Dap(Me)
<220> FEATURE:
<221> NAME/KEY: MOD_RES
<222> LOCATION: (14)..(14)
<223> OTHER INFORMATION: tert-butylglycine

<400> SEQUENCE: 22

Ala Xaa Xaa Asn Glu Xaa Xaa Xaa Glu Asp Phe Tyr Asp Xaa Cys
1               5                   10                  15

<210> SEQ ID NO 23
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: PYA
<220> FEATURE:
<221> NAME/KEY: MOD_RES
<222> LOCATION: (2)..(4)
<223> OTHER INFORMATION: D-Asp
<220> FEATURE:
<221> NAME/KEY: MOD_RES
<222> LOCATION: (5)..(6)
<223> OTHER INFORMATION: Sarcosine
<220> FEATURE:
<221> NAME/KEY: MOD_RES
<222> LOCATION: (8)..(8)
<223> OTHER INFORMATION: Dap(Me)
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (12)..(12)
<223> OTHER INFORMATION: L-1-Naphthylalanine
<220> FEATURE:
<221> NAME/KEY: MOD_RES
<222> LOCATION: (13)..(13)
<223> OTHER INFORMATION: D-amino acid
<220> FEATURE:
<221> NAME/KEY: MOD_RES
<222> LOCATION: (14)..(14)
<223> OTHER INFORMATION: Dap(Me)
<220> FEATURE:
<221> NAME/KEY: MOD_RES
<222> LOCATION: (20)..(20)
<223> OTHER INFORMATION: tert-butylglycine

<400> SEQUENCE: 23

Xaa Xaa Xaa Xaa Xaa Xaa Ala Xaa Xaa Asn Glu Xaa Xaa Xaa Glu Asp
1               5                   10                  15

Phe Tyr Asp Xaa Cys
            20
```

```
<210> SEQ ID NO 24
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: PYA-A
<220> FEATURE:
<221> NAME/KEY: MOD_RES
<222> LOCATION: (2)..(2)
<223> OTHER INFORMATION: Dap(Me)
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (6)..(6)
<223> OTHER INFORMATION: L-1-Naphthylalanine
<220> FEATURE:
<221> NAME/KEY: MOD_RES
<222> LOCATION: (7)..(7)
<223> OTHER INFORMATION: D-Ala
<220> FEATURE:
<221> NAME/KEY: MOD_RES
<222> LOCATION: (14)..(14)
<223> OTHER INFORMATION: tert-butylglycine
<220> FEATURE:
<221> NAME/KEY: MOD_RES
<222> LOCATION: (15)..(15)
<223> OTHER INFORMATION: Dap(Me)

<400> SEQUENCE: 24

Xaa Xaa Xaa Asn Glu Xaa Xaa Cys Glu Asp Phe Tyr Asp Xaa Xaa
1               5                   10                  15

<210> SEQ ID NO 25
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: PYA
<220> FEATURE:
<221> NAME/KEY: MOD_RES
<222> LOCATION: (2)..(4)
<223> OTHER INFORMATION: D-Asp
<220> FEATURE:
<221> NAME/KEY: MOD_RES
<222> LOCATION: (5)..(6)
<223> OTHER INFORMATION: Sarcosine
<220> FEATURE:
<221> NAME/KEY: MOD_RES
<222> LOCATION: (8)..(8)
<223> OTHER INFORMATION: Dap(Me)
<220> FEATURE:
<221> NAME/KEY: MOD_RES
<222> LOCATION: (9)..(9)
<223> OTHER INFORMATION: D-Ala
<220> FEATURE:
<221> NAME/KEY: MOD_RES
<222> LOCATION: (12)..(12)
<223> OTHER INFORMATION: L-1-Naphthylalanine
<220> FEATURE:
<221> NAME/KEY: MOD_RES
```

```
<222> LOCATION: (13)..(13)
<223> OTHER INFORMATION: D-Ala
<220> FEATURE:
<221> NAME/KEY: MOD_RES
<222> LOCATION: (20)..(20)
<223> OTHER INFORMATION: tert-butylglycine
<220> FEATURE:
<221> NAME/KEY: MOD_RES
<222> LOCATION: (21)..(21)
<223> OTHER INFORMATION: Dap(Me)

<400> SEQUENCE: 25

Xaa Xaa Xaa Xaa Xaa Xaa Ala Xaa Xaa Asn Glu Xaa Xaa Cys Glu Asp
1               5                   10                  15

Phe Tyr Asp Xaa Xaa
            20

<210> SEQ ID NO 26
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: PYA
<220> FEATURE:
<221> NAME/KEY: MOD_RES
<222> LOCATION: (2)..(2)
<223> OTHER INFORMATION: B-Ala
<220> FEATURE:
<221> NAME/KEY: MOD_RES
<222> LOCATION: (3)..(7)
<223> OTHER INFORMATION: Sarcosine
<220> FEATURE:
<221> NAME/KEY: MOD_RES
<222> LOCATION: (9)..(9)
<223> OTHER INFORMATION: Dap(Me)
<220> FEATURE:
<221> NAME/KEY: MOD_RES
<222> LOCATION: (10)..(10)
<223> OTHER INFORMATION: D-Ala
<220> FEATURE:
<221> NAME/KEY: MOD_RES
<222> LOCATION: (13)..(13)
<223> OTHER INFORMATION: L-1-Naphthylalanine
<220> FEATURE:
<221> NAME/KEY: MOD_RES
<222> LOCATION: (14)..(14)
<223> OTHER INFORMATION: D-Ala
<220> FEATURE:
<221> NAME/KEY: MOD_RES
<222> LOCATION: (21)..(21)
<223> OTHER INFORMATION: tert-butylglycine
<220> FEATURE:
<221> NAME/KEY: MOD_RES
<222> LOCATION: (22)..(22)
<223> OTHER INFORMATION: Dap(Me)

<400> SEQUENCE: 26

Xaa Xaa Xaa Xaa Xaa Xaa Xaa Ala Xaa Xaa Asn Glu Xaa Xaa Cys Glu
1               5                   10                  15

Asp Phe Tyr Asp Xaa Xaa
            20

<210> SEQ ID NO 27
<211> LENGTH: 26
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: beta-Ala
<220> FEATURE:
<221> NAME/KEY: MOD_RES
<222> LOCATION: (2)..(11)
<223> OTHER INFORMATION: Sarcosine
<220> FEATURE:
<221> NAME/KEY: MOD_RES
<222> LOCATION: (13)..(13)
<223> OTHER INFORMATION: Dap(Me)
<220> FEATURE:
<221> NAME/KEY: MOD_RES
<222> LOCATION: (14)..(14)
<223> OTHER INFORMATION: D-amino acid
<220> FEATURE:
<221> NAME/KEY: MOD_RES
<222> LOCATION: (17)..(17)
<223> OTHER INFORMATION: L-1-Naphthylalanine
<220> FEATURE:
<221> NAME/KEY: MOD_RES
<222> LOCATION: (18)..(18)
<223> OTHER INFORMATION: D-amino acid
<220> FEATURE:
<221> NAME/KEY: MOD_RES
<222> LOCATION: (25)..(25)
<223> OTHER INFORMATION: tert-butylglycine
<220> FEATURE:
<221> NAME/KEY: MOD_RES
<222> LOCATION: (26)..(26)
<223> OTHER INFORMATION: Dap(Me)

<400> SEQUENCE: 27

Xaa Xaa Xaa Xaa Xaa Xaa Xaa Xaa Xaa Xaa Xaa Ala Xaa Xaa Asn Glu
1               5                   10                  15

Xaa Xaa Cys Glu Asp Phe Tyr Asp Xaa Xaa
            20                  25

<210> SEQ ID NO 28
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Dap(Me)
<220> FEATURE:
<221> NAME/KEY: MOD_RES
<222> LOCATION: (3)..(3)
<223> OTHER INFORMATION: D-amino acid
<220> FEATURE:
<221> NAME/KEY: MOD_RES
<222> LOCATION: (6)..(6)
<223> OTHER INFORMATION: L-1-Naphthylalanine
<220> FEATURE:
<221> NAME/KEY: MOD_RES
<222> LOCATION: (7)..(7)
<223> OTHER INFORMATION: D-Ala
<220> FEATURE:
<221> NAME/KEY: MOD_RES
<222> LOCATION: (14)..(14)
<223> OTHER INFORMATION: tert-butylglycine
<220> FEATURE:
<221> NAME/KEY: MOD_RES
<222> LOCATION: (15)..(15)
<223> OTHER INFORMATION: Dap(Me)

<400> SEQUENCE: 28
```

Ala Xaa Xaa Asn Glu Xaa Xaa Cys Glu Asp Phe Tyr Asp Xaa Xaa
1               5                   10                  15

<210> SEQ ID NO 29
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: PYA
<220> FEATURE:
<221> NAME/KEY: MOD_RES
<222> LOCATION: (2)..(2)
<223> OTHER INFORMATION: B-Ala
<220> FEATURE:
<221> NAME/KEY: MOD_RES
<222> LOCATION: (3)..(12)
<223> OTHER INFORMATION: Sarcosine
<220> FEATURE:
<221> NAME/KEY: MOD_RES
<222> LOCATION: (14)..(14)
<223> OTHER INFORMATION: Dap(Me)
<220> FEATURE:
<221> NAME/KEY: MOD_RES
<222> LOCATION: (15)..(15)
<223> OTHER INFORMATION: D-Ala
<220> FEATURE:
<221> NAME/KEY: MOD_RES
<222> LOCATION: (18)..(18)
<223> OTHER INFORMATION: L-1-Naphthylalanine
<220> FEATURE:
<221> NAME/KEY: MOD_RES
<222> LOCATION: (19)..(19)
<223> OTHER INFORMATION: D-Ala
<220> FEATURE:
<221> NAME/KEY: MOD_RES
<222> LOCATION: (26)..(26)
<223> OTHER INFORMATION: tert-butylglycine
<220> FEATURE:
<221> NAME/KEY: MOD_RES
<222> LOCATION: (27)..(27)
<223> OTHER INFORMATION: Dap(Me)

<400> SEQUENCE: 29

Xaa Xaa Xaa Xaa Xaa Xaa Xaa Xaa Xaa Xaa Xaa Xaa Ala Xaa Xaa Asn
1               5                   10                  15

Glu Xaa Xaa Cys Glu Asp Phe Tyr Asp Xaa Xaa
            20                  25

<210> SEQ ID NO 30
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: B-Ala
<220> FEATURE:
<221> NAME/KEY: MOD_RES
<222> LOCATION: (2)..(11)
<223> OTHER INFORMATION: Sarcosine
<220> FEATURE:
<221> NAME/KEY: MOD_RES
<222> LOCATION: (13)..(13)
<223> OTHER INFORMATION: Dap(Me)

```
<220> FEATURE:
<221> NAME/KEY: MOD_RES
<222> LOCATION: (14)..(14)
<223> OTHER INFORMATION: D-Ala
<220> FEATURE:
<221> NAME/KEY: MOD_RES
<222> LOCATION: (17)..(17)
<223> OTHER INFORMATION: L-1-Naphthylalanine
<220> FEATURE:
<221> NAME/KEY: MOD_RES
<222> LOCATION: (18)..(18)
<223> OTHER INFORMATION: D-Ala
<220> FEATURE:
<221> NAME/KEY: MOD_RES
<222> LOCATION: (25)..(25)
<223> OTHER INFORMATION: tert-butylglycine
<220> FEATURE:
<221> NAME/KEY: MOD_RES
<222> LOCATION: (26)..(26)
<223> OTHER INFORMATION: Dap(Me)

<400> SEQUENCE: 30

Xaa Xaa Xaa Xaa Xaa Xaa Xaa Xaa Xaa Xaa Xaa Ala Xaa Xaa Asn Glu
1               5                   10                  15

Xaa Xaa Cys Glu Asp Phe Tyr Asp Xaa Xaa
            20                  25

<210> SEQ ID NO 31
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: Dap(Me)
<220> FEATURE:
<221> NAME/KEY: MOD_RES
<222> LOCATION: (2)..(2)
<223> OTHER INFORMATION: D-Ala
<220> FEATURE:
<221> NAME/KEY: MOD_RES
<222> LOCATION: (5)..(5)
<223> OTHER INFORMATION: L-1-Naphthylalanine
<220> FEATURE:
<221> NAME/KEY: MOD_RES
<222> LOCATION: (6)..(6)
<223> OTHER INFORMATION: D-Ala
<220> FEATURE:
<221> NAME/KEY: MOD_RES
<222> LOCATION: (13)..(13)
<223> OTHER INFORMATION: tert-butylglycine
<220> FEATURE:
<221> NAME/KEY: MOD_RES
<222> LOCATION: (14)..(14)
<223> OTHER INFORMATION: Dap(Me)

<400> SEQUENCE: 31

Xaa Xaa Asn Glu Xaa Xaa Cys Glu Asp Phe Tyr Asp Xaa Xaa
1               5                   10

<210> SEQ ID NO 32
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
```

```
<222> LOCATION: (2)..(2)
<223> OTHER INFORMATION: Dap(Me)
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (6)..(6)
<223> OTHER INFORMATION: L-1-Naphthylalanine
<220> FEATURE:
<221> NAME/KEY: MOD_RES
<222> LOCATION: (7)..(7)
<223> OTHER INFORMATION: D-Ala
<220> FEATURE:
<221> NAME/KEY: MOD_RES
<222> LOCATION: (14)..(14)
<223> OTHER INFORMATION: tert-butylglycine
<220> FEATURE:
<221> NAME/KEY: MOD_RES
<222> LOCATION: (15)..(15)
<223> OTHER INFORMATION: Dap(Me)

<400> SEQUENCE: 32

Ala Xaa Xaa Asn Glu Xaa Xaa Cys Glu Asp Phe Tyr Asp Xaa Xaa
1               5                   10                  15

<210> SEQ ID NO 33
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: Dap(Me)
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (6)..(6)
<223> OTHER INFORMATION: L-1-Naphthylalanine
<220> FEATURE:
<221> NAME/KEY: MOD_RES
<222> LOCATION: (7)..(7)
<223> OTHER INFORMATION: D-Ala
<220> FEATURE:
<221> NAME/KEY: MOD_RES
<222> LOCATION: (8)..(8)
<223> OTHER INFORMATION: Dap(Me)
<220> FEATURE:
<221> NAME/KEY: MOD_RES
<222> LOCATION: (14)..(14)
<223> OTHER INFORMATION: tert-butylglycine
<220> FEATURE:
<221> NAME/KEY: MOD_RES
<222> LOCATION: (15)..(15)
<223> OTHER INFORMATION: Dap(Me)

<400> SEQUENCE: 33

Ala Xaa Xaa Asn Glu Xaa Xaa Xaa Glu Asp Phe Tyr Asp Xaa Xaa
1               5                   10                  15

<210> SEQ ID NO 34
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
```

```
      Synthetic peptide"
<220> FEATURE:
<221> NAME/KEY: MOD_RES
<222> LOCATION: (2)..(2)
<223> OTHER INFORMATION: Dap
<220> FEATURE:
<221> NAME/KEY: MOD_RES
<222> LOCATION: (3)..(3)
<223> OTHER INFORMATION: D-Ala
<220> FEATURE:
<221> NAME/KEY: MOD_RES
<222> LOCATION: (6)..(6)
<223> OTHER INFORMATION: L-1-Naphthylalanine
<220> FEATURE:
<221> NAME/KEY: MOD_RES
<222> LOCATION: (7)..(7)
<223> OTHER INFORMATION: D-Ala
<220> FEATURE:
<221> NAME/KEY: MOD_RES
<222> LOCATION: (14)..(14)
<223> OTHER INFORMATION: tert-butylglycine
<220> FEATURE:
<221> NAME/KEY: MOD_RES
<222> LOCATION: (15)..(15)
<223> OTHER INFORMATION: Dap

<400> SEQUENCE: 34

Ala Xaa Xaa Asn Glu Xaa Xaa Cys Glu Asp Phe Tyr Asp Xaa Xaa
1               5                   10                  15

<210> SEQ ID NO 35
<211> LENGTH: 27
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (1)..(1)
<223> OTHER INFORMATION: PYA
<220> FEATURE:
<221> NAME/KEY: MOD_RES
<222> LOCATION: (2)..(2)
<223> OTHER INFORMATION: beta-Ala
<220> FEATURE:
<221> NAME/KEY: MOD_RES
<222> LOCATION: (3)..(12)
<223> OTHER INFORMATION: Sarcosine
<220> FEATURE:
<221> NAME/KEY: MOD_RES
<222> LOCATION: (14)..(14)
<223> OTHER INFORMATION: Dap
<220> FEATURE:
<221> NAME/KEY: MOD_RES
<222> LOCATION: (15)..(15)
<223> OTHER INFORMATION: D-Ala
<220> FEATURE:
<221> NAME/KEY: MOD_RES
<222> LOCATION: (18)..(18)
<223> OTHER INFORMATION: L-1-Naphthylalanine
<220> FEATURE:
<221> NAME/KEY: MOD_RES
<222> LOCATION: (19)..(19)
<223> OTHER INFORMATION: D-Ala
<220> FEATURE:
<221> NAME/KEY: MOD_RES
<222> LOCATION: (26)..(26)
<223> OTHER INFORMATION: tert-butylglycine
<220> FEATURE:
<221> NAME/KEY: MOD_RES
<222> LOCATION: (27)..(27)
<223> OTHER INFORMATION: Dap

<400> SEQUENCE: 35
```

```
Xaa Xaa Xaa Xaa Xaa Xaa Xaa Xaa Xaa Xaa Xaa Ala Xaa Xaa Asn
1               5                   10                  15

Glu Xaa Xaa Cys Glu Asp Phe Tyr Asp Xaa Xaa
            20              25
```